United States Patent
Narain et al.

(10) Patent No.: US 11,400,058 B2
(45) Date of Patent: *Aug. 2, 2022

(54) INTRAVENOUS FORMULATIONS OF COENZYME Q10 (COQ10) AND METHODS OF USE THEREOF

(75) Inventors: Niven Rajin Narain, Cambridge, MA (US); John Patrick McCook, Frisco, TX (US)

(73) Assignee: Berg LLC, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/046,221

(22) Filed: Mar. 11, 2011

(65) Prior Publication Data

US 2011/0229554 A1    Sep. 22, 2011

Related U.S. Application Data

(60) Provisional application No. 61/313,632, filed on Mar. 12, 2010, provisional application No. 61/385,107, filed on Sep. 21, 2010.

(51) Int. Cl.
| | | |
|---|---|---|
| *A61K 31/122* | (2006.01) | |
| *A61K 47/34* | (2017.01) | |
| *A61K 47/24* | (2006.01) | |
| *A61K 9/00* | (2006.01) | |
| *A61K 9/10* | (2006.01) | |

(52) U.S. Cl.
CPC .......... *A61K 31/122* (2013.01); *A61K 9/0019* (2013.01); *A61K 9/10* (2013.01); *A61K 47/24* (2013.01); *A61K 47/34* (2013.01)

(58) Field of Classification Search
CPC ...... A61K 31/112; A61K 9/0019; A61K 9/10; A61K 47/24; A61K 47/34
See application file for complete search history.

(56) References Cited

U.S. PATENT DOCUMENTS

| | | |
|---|---|---|
| 4,515,736 A | 5/1985 | Oearner |
| 4,525,350 A | 6/1985 | Casey et al. |
| 4,636,381 A | 1/1987 | Takada et al. |
| 4,654,373 A | 3/1987 | Bertelli |
| 4,824,669 A | 4/1989 | Folkers et al. |
| 4,895,727 A | 1/1990 | Allen |
| 5,015,483 A | 5/1991 | Haynes et al. |
| 5,045,559 A | 9/1991 | Scott |
| 5,192,528 A | 3/1993 | Radhakrishnan et al. |
| 5,220,042 A | 6/1993 | Iwaki et al. |
| 5,362,494 A | 11/1994 | Zysman et al. |
| 5,378,461 A | 1/1995 | Neigut |
| 5,539,021 A | 7/1996 | Pate et al. |
| 5,569,464 A | 10/1996 | Endo et al. |
| 5,602,184 A | 2/1997 | Myers et al. |
| 5,603,958 A | 2/1997 | Morein et al. |
| 5,651,991 A | 7/1997 | Sugiyama et al. |
| 5,688,842 A | 11/1997 | Pate, III et al. |
| 5,700,482 A | 12/1997 | Frederiksen et al. |
| 5,700,653 A | 12/1997 | Lu et al. |
| 5,738,868 A | 4/1998 | Shinkarenko |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,900,230 A | 5/1999 | Cutler |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,566 A | 4/2000 | Behnam et al. |
| 6,048,886 A | 4/2000 | Neigut |
| 6,054,261 A | 4/2000 | Masterson |
| 6,071,495 A | 6/2000 | Unger et al. |
| 6,107,276 A | 8/2000 | Carli et al. |

(Continued)

FOREIGN PATENT DOCUMENTS

| | | |
|---|---|---|
| CA | 2553690 A1 | 8/2005 |
| CA | 2680825 A1 | 9/2008 |

(Continued)

OTHER PUBLICATIONS

International Search Report and Written Opinion of the International Searching Authority issued for PCT/US2011/028042, dated Nov. 24, 2011.

(Continued)

*Primary Examiner* — Adam C Milligan
(74) *Attorney, Agent, or Firm* — McCarter & English, LLP; Jill Mello

(57) ABSTRACT

Disclosed herein are formulations suitable for parenteral administration of certain hydrophobic active agents such as Coenzyme Q10. Methods of preparing the same and methods of treatment of oncological disorders using the same are also provided herein. The formulations comprise an aqueous solution; a hydrophobic active agent dispersed to form a colloidal nano-dispersion of particles; and at least one of a dispersion stabilizing agent and an opsonization reducer wherein the colloidal nano-dispersion of the active agent is dispersed into nano-dispersion particles having a mean size of less than 200-nm. Methods of preparing the parenteral formulations comprise dispersing the hydrophobic active agent by high pressure homogenization by (1) adding hydrophobic active agent to a 65° C. bath of water and mixing to form a hydrophobic active agent/water mixture; (2) adding a dispersion stabilizing agent to the hydrophobic active agent/water mixture and mix at 65° C. to form a hydrophobic active agent/water/stabilizer mixture; (3) adding an opsonization reducer to form a hydrophobic active agent/water/stabilizer/reducer mixture; (4) pre-heating a Microfluidizer to 65° C.; and (5) processing by mixing the hydrophobic active agent/water/stabilizer/reducer mixture in the Microfluidizer at 65° C. such that a hydrophobic active agent colloidal nano-dispersion having a mean particle size less than 200-nm is formed. Provided herein are also methods of treating oncological disorders by administering formulations described herein to a subject such that treatment or prevention of the oncological disorder occurs.

30 Claims, 22 Drawing Sheets

(56) References Cited

U.S. PATENT DOCUMENTS

| | | |
|---|---|---|
| 6,184,353 B1 | 2/2001 | Evans et al. |
| 6,197,349 B1 | 3/2001 | Westesen et al. |
| 6,200,550 B1 | 3/2001 | Masterson et al. |
| 6,228,891 B1 | 5/2001 | Enzmann et al. |
| 6,261,575 B1 | 7/2001 | Hoppe et al. |
| 6,300,377 B1 | 10/2001 | Chopra |
| 6,303,582 B1 | 10/2001 | Eljamal et al. |
| 6,334,999 B1 | 1/2002 | Gilbert et al. |
| 6,346,233 B1 | 2/2002 | Knight et al. |
| 6,372,234 B1 | 4/2002 | Deckers et al. |
| 6,403,116 B1 * | 6/2002 | Anderson et al. ............ 424/439 |
| 6,403,117 B1 | 6/2002 | Sprott et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,468,552 B1 | 10/2002 | Stahl et al. |
| 6,479,058 B1 | 11/2002 | McCadden |
| 6,482,943 B1 | 11/2002 | Blokhin et al. |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,652,837 B1 | 11/2003 | Edwards et al. |
| 6,652,891 B2 | 11/2003 | Selzer |
| 6,656,928 B1 | 12/2003 | McCadden |
| 6,663,886 B2 | 12/2003 | Nagy et al. |
| 6,686,485 B2 | 2/2004 | West |
| 6,696,082 B2 | 2/2004 | McCully |
| 6,696,484 B2 | 2/2004 | Liao et al. |
| 6,699,464 B1 | 3/2004 | Popp et al. |
| 6,727,234 B2 | 4/2004 | Wiemer et al. |
| 6,733,790 B1 | 5/2004 | Garces Garces |
| 6,740,338 B1 | 5/2004 | Chopra |
| 6,753,325 B2 | 6/2004 | Rosenbloom |
| 6,756,062 B2 | 6/2004 | Johnston et al. |
| 6,803,193 B1 | 10/2004 | Hopper et al. |
| 6,806,069 B2 | 10/2004 | Chokshi |
| 6,809,176 B2 | 10/2004 | Blokhin et al. |
| 6,811,767 B1 | 11/2004 | Bosch et al. |
| 6,862,890 B2 | 3/2005 | Williams, III et al. |
| 6,867,024 B2 | 3/2005 | Chokshi |
| 6,906,106 B2 | 6/2005 | Chevalier |
| 6,923,988 B2 | 8/2005 | Patel et al. |
| 7,001,888 B2 | 2/2006 | Tidmarsh et al. |
| 7,025,955 B2 | 4/2006 | Siddiqui et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,094,804 B2 | 8/2006 | Behnam |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,198,801 B2 | 4/2007 | Carrara et al. |
| 7,208,298 B2 | 4/2007 | Miyake et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,438,903 B2 | 10/2008 | Parkhideh |
| 7,794,694 B2 | 9/2010 | Giacomoni et al. |
| 8,147,825 B2 | 4/2012 | Hsia et al. |
| 8,337,931 B2 | 12/2012 | Bromley |
| 8,372,395 B2 | 2/2013 | Yu et al. |
| 8,454,945 B2 | 6/2013 | McCook et al. |
| 8,685,446 B2 | 4/2014 | Casana-Giner et al. |
| 8,753,675 B1 | 6/2014 | Chopra |
| 8,785,598 B2 | 7/2014 | Chung et al. |
| 8,815,567 B2 | 8/2014 | Ye |
| 8,961,958 B2 | 2/2015 | Harris et al. |
| 9,168,216 B2 | 10/2015 | Gavin et al. |
| 2001/0021704 A1 | 9/2001 | Ghyczy et al. |
| 2001/0022965 A1 | 9/2001 | Heger et al. |
| 2001/0043909 A1 | 11/2001 | SaNogueira et al. |
| 2002/0039595 A1 | 4/2002 | Keller |
| 2002/0044913 A1 | 4/2002 | Hamilton |
| 2002/0048551 A1 | 4/2002 | Keller et al. |
| 2002/0048559 A1 | 4/2002 | Shinoda et al. |
| 2002/0049422 A1 | 4/2002 | Brewitt |
| 2002/0071852 A1 | 6/2002 | Deckers et al. |
| 2002/0102296 A1 | 8/2002 | Giovanella et al. |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0155151 A1 | 10/2002 | Enzmann et al. |
| 2002/0156302 A1 | 10/2002 | West |
| 2002/0182199 A1 | 12/2002 | Hoppe et al. |
| 2003/0012762 A1 | 1/2003 | Zulli et al. |
| 2003/0031688 A1 | 2/2003 | Ghosh et al. |
| 2003/0044441 A1 | 3/2003 | Schmid et al. |
| 2003/0049323 A1 | 3/2003 | Hitt et al. |
| 2003/0077297 A1 | 4/2003 | Chen et al. |
| 2003/0091518 A1 | 5/2003 | Pauly et al. |
| 2003/0104048 A1 | 6/2003 | Patel et al. |
| 2003/0104080 A1 | 6/2003 | Singh et al. |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0190284 A1 | 10/2003 | Annapragada et al. |
| 2003/0215406 A1 | 11/2003 | Schreiner et al. |
| 2003/0219472 A1 | 11/2003 | Pauletti et al. |
| 2004/0028614 A1 | 2/2004 | Corbella et al. |
| 2004/0034107 A1 | 2/2004 | Enzmann |
| 2004/0043045 A1 | 3/2004 | Seipel et al. |
| 2004/0063648 A1 | 4/2004 | Pandol et al. |
| 2004/0067260 A1 | 4/2004 | Milley et al. |
| 2004/0086538 A1 | 5/2004 | Sauermann et al. |
| 2004/0109880 A1 | 6/2004 | Pauly et al. |
| 2004/0110848 A1 | 6/2004 | Peffley et al. |
| 2004/0122109 A1 | 6/2004 | Fujii et al. |
| 2004/0126367 A1 | 7/2004 | Fujii et al. |
| 2004/0137070 A1 | 7/2004 | Scherzer et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0151711 A1 | 8/2004 | West |
| 2004/0167034 A1 | 8/2004 | Coote et al. |
| 2004/0170560 A1 * | 9/2004 | Fossheim et al. ........... 424/1.29 |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |

(56) References Cited

U.S. PATENT DOCUMENTS

| | | |
|---|---|---|
| 2004/0197279 A1 | 10/2004 | Bleckmann et al. |
| 2004/0197354 A1 | 10/2004 | Doring et al. |
| 2004/0208935 A1 | 10/2004 | Giovanella et al. |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019278 A1 | 1/2005 | Berg-Schultz |
| 2005/0019353 A1 | 1/2005 | Prinz et al. |
| 2005/0036976 A1 | 2/2005 | Rubin et al. |
| 2005/0037036 A1 | 2/2005 | Nielsen et al. |
| 2005/0058610 A1 | 3/2005 | Baschong et al. |
| 2005/0069582 A1 | 3/2005 | Fantuzzi |
| 2005/0070611 A1 | 3/2005 | Fantuzzi |
| 2005/0079164 A1 | 4/2005 | Fantuzzi et al. |
| 2005/0084505 A1 | 4/2005 | Muller et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118209 A1 | 6/2005 | Jentszch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0142665 A1 | 6/2005 | Wachtel et al. |
| 2005/0147598 A1 | 7/2005 | Ueda et al. |
| 2005/0152856 A2 | 7/2005 | Andersson et al. |
| 2005/0214333 A1 | 9/2005 | Lanzendoerfer et al. |
| 2005/0214369 A1 | 9/2005 | Ko et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288378 A1 | 12/2005 | Yan et al. |
| 2006/0002964 A9 | 1/2006 | Schreiber et al. |
| 2006/0002992 A1 | 1/2006 | Schmehl et al. |
| 2006/0008426 A1 | 1/2006 | Doring et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0051462 A1 | 3/2006 | Wang |
| 2006/0057081 A1 | 3/2006 | Boxrud |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0121016 A1 | 6/2006 | Lee |
| 2006/0127384 A1 | 6/2006 | Capaccioli et al. |
| 2006/0140970 A1 | 6/2006 | Telerman et al. |
| 2006/0153783 A1 | 7/2006 | Ehlis et al. |
| 2006/0154993 A1 | 7/2006 | Littarru et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0198830 A1 | 9/2006 | Shastri et al. |
| 2006/0204447 A1 | 9/2006 | Knight et al. |
| 2006/0251690 A1 | 11/2006 | Lipshutz et al. |
| 2006/0251708 A1 | 11/2006 | Chen et al. |
| 2006/0280691 A1 | 12/2006 | Wang et al. |
| 2006/0286046 A1 | 12/2006 | Haber |
| 2006/0292220 A1 | 12/2006 | Giordano et al. |
| 2007/0053985 A1 | 3/2007 | Ueda et al. |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0122349 A1 | 5/2007 | Wachtel et al. |
| 2007/0154498 A1 | 7/2007 | Bortz et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0218042 A1 | 9/2007 | Khaled |
| 2007/0243180 A1 | 10/2007 | Tanaka et al. |
| 2007/0248590 A1 | 10/2007 | Milne et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0259009 A1* | 11/2007 | Linder .................. 424/400 |
| 2007/0275021 A1 | 11/2007 | Lee et al. |
| 2008/0008694 A1 | 1/2008 | Elgebaly et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0299100 A1 | 4/2008 | Hsia et al. |
| 2008/0102313 A1 | 5/2008 | Nilsen et al. |
| 2008/0138326 A1 | 6/2008 | Fujii et al. |
| 2008/0207560 A1 | 8/2008 | Harada et al. |
| 2008/0219963 A1 | 9/2008 | Paolo et al. |
| 2008/0233183 A1* | 9/2008 | McCook et al. .......... 424/450 |
| 2008/0248095 A1 | 10/2008 | Giovanella et al. |
| 2008/0254017 A1 | 10/2008 | Kane et al. |
| 2008/0299049 A1 | 12/2008 | Stangl |
| 2008/0312128 A1 | 12/2008 | Chaum et al. |
| 2009/0060891 A1 | 3/2009 | Harris et al. |
| 2009/0098200 A1 | 4/2009 | Temtsin Krayz et al. |
| 2009/0183554 A1 | 7/2009 | Grant et al. |
| 2009/0202509 A1 | 8/2009 | Leverve |
| 2009/0246186 A1 | 10/2009 | Shinagawa et al. |
| 2009/0280987 A1 | 11/2009 | Strobel |
| 2010/0047297 A1 | 2/2010 | Petersen |
| 2010/0061969 A1 | 3/2010 | Otsubo et al. |
| 2010/0062048 A1 | 3/2010 | Hsia et al. |
| 2010/0080762 A1 | 4/2010 | Goralczyk |
| 2010/0080785 A1 | 4/2010 | Berl |
| 2010/0098752 A1 | 4/2010 | Pinsky |
| 2010/0099775 A1 | 4/2010 | Schwarz et al. |
| 2010/0119589 A1 | 5/2010 | Selischeva et al. |
| 2010/0129431 A1 | 5/2010 | Schwarz et al. |
| 2010/0189596 A1 | 7/2010 | Deng et al. |
| 2010/0215725 A1 | 8/2010 | Schwarz et al. |
| 2011/0027247 A1 | 2/2011 | Narain et al. |
| 2011/0110914 A1 | 5/2011 | Narain et al. |
| 2011/0142914 A1 | 6/2011 | Persaud et al. |
| 2011/0229554 A1 | 9/2011 | Narain et al. |
| 2011/0318405 A1 | 12/2011 | Erwin |
| 2012/0064136 A1 | 3/2012 | Baker, Jr. et al. |
| 2012/0141446 A1 | 6/2012 | Patel |
| 2012/0141448 A1 | 6/2012 | De Ferra et al. |
| 2012/0164215 A1 | 6/2012 | Hsia et al. |
| 2012/0201801 A1 | 8/2012 | Hsia et al. |
| 2012/0244134 A1 | 9/2012 | Chen et al. |
| 2012/0321698 A1 | 12/2012 | Narain et al. |
| 2013/0019860 A1 | 1/2013 | Depla et al. |
| 2013/0202683 A1 | 8/2013 | McCook et al. |
| 2014/0239525 A1 | 8/2014 | McConville et al. |
| 2015/0023940 A1 | 1/2015 | Narain et al. |

(56) References Cited

U.S. PATENT DOCUMENTS

| | | |
|---|---|---|
| 2015/0150801 A1 | 6/2015 | Park et al. |
| 2015/0238429 A1 | 8/2015 | Fang et al. |

FOREIGN PATENT DOCUMENTS

| | | |
|---|---|---|
| EP | 1404291 A1 | 4/2004 |
| EP | 1493437 A1 | 1/2005 |
| EP | 1565163 B1 | 8/2005 |
| EP | 1849481 A1 | 10/2007 |
| EP | 1475083 B1 | 12/2007 |
| EP | 1476032 B1 | 4/2008 |
| EP | 1908459 A1 | 4/2008 |
| EP | 1957037 A1 | 8/2008 |
| EP | 2567705 A2 | 3/2013 |
| KR | 10-2009-0088126 A | 8/2009 |
| WO | 198601714 A1 | 3/1986 |
| WO | 198801862 A1 | 3/1988 |
| WO | 9316704 A1 | 9/1993 |
| WO | 9617626 A2 | 6/1996 |
| WO | 199800111 A1 | 1/1998 |
| WO | 1999065469 A2 | 12/1999 |
| WO | 0044862 A1 | 8/2000 |
| WO | 02078727 A1 | 10/2002 |
| WO | 2002/089771 A1 | 11/2002 |
| WO | 0217879 A1 | 5/2003 |
| WO | 2003075820 A1 | 9/2003 |
| WO | 2003090682 A2 | 11/2003 |
| WO | 2004003564 A2 | 1/2004 |
| WO | 2004035553 A1 | 4/2004 |
| WO | 2004039348 A1 | 5/2004 |
| WO | 2005069916 A2 | 8/2005 |
| WO | 2005112957 A1 | 12/2005 |
| WO | 2006/032675 A1 | 3/2006 |
| WO | 2006073190 A1 | 7/2006 |
| WO | 2005069916 A3 | 10/2006 |
| WO | 2006108556 A2 | 10/2006 |
| WO | 2007131047 A2 | 11/2007 |
| WO | 2008023264 A2 | 2/2008 |
| WO | 2008024020 A1 | 2/2008 |
| WO | 2008063341 A2 | 5/2008 |
| WO | 2009005215 A1 | 1/2009 |
| WO | 2009012718 | 1/2009 |
| WO | 2009012718 A1 | 1/2009 |
| WO | 2009073843 A1 | 6/2009 |
| WO | 2009126764 A1 | 10/2009 |
| WO | 2011112900 A2 | 9/2011 |
| WO | 2012161562 A1 | 11/2012 |
| WO | 2013175266 A1 | 11/2013 |
| WO | 2014138922 A1 | 9/2014 |
| WO | 2015127537 A1 | 9/2015 |
| WO | 2015157455 A1 | 10/2015 |

OTHER PUBLICATIONS

Owens, Donald E. III, et al., Opsonization, biodistribution, and pharmacokinetics of polymeric nanoparticles, International Journal of Pharmaceutics, 307(1):93-102, 2006.

Bliznakov, E., "Effect of Stimulation of the Host Defense System by Coenzyme Q10 on Dibenzpyrene-Induced Tumors and Infection with Friend Leukemia Virus in Mice", Proc. Nat. Acad. Sci. USA, 70(2): 390-394 (Feb. 1973).

Bliznakov et al., "Coenzymes Q: Stimulants of the Phagocytic Activity in Rats and Immune Response in Mice", Experientia, 26(9): 953-954 (Sep. 1970).

Hodges et al., "CoQ10: could it have a role in cancer management?", BioFactors, vol. 9, pp. 365-370 (1999).

International Preliminary Report on Patentability issued in PCT/US2008/085669 dated Jun. 17, 2010.

International Search Report from Application No. PCT/US2007/068052 dated Apr. 15, 2008.

International Search Report from Application No. PCT/US2008/057786 dated Oct. 23, 2008.

International Search Report issued in PCT/US2012/042999 dated Aug. 14, 2012.

International Search Report issued in PCT/US2012/043001 dated Oct. 17, 2012.

International Search Report of International Application No. PCT/US2010/034453 dated Jan. 31, 2011.

Johnson et al., "Aerosolization and Hygroscopic Growth Evaluation of Lyophilized Liposome Aerosols Under Controlled Temperature and Relative Humidity Conditions," Aerosol Science and Technology, 1996, vol. 25, (1): pp. 22-30.

Kokawa et al., "Coenzyme Q10 in cancer chemotherapy-experimental studies on augmentation of the effects of masked compounds, especially in the combined chemotherapy with immunopotentiators", Gan To Kagayu Ryoho. Cancer and Chemotherapy, Mar. 1993, vol. 10, No. 3, pp. 768-774. XP002473825, Abstract. (Article in Japanese).

Lockwood et al., "Apparent partial remission of breast cancer in 'high risk' patients supplemented with nutritional antioxidants, essential fatty acids and coenzyme Q10", Mol-Aspects-Med., vol. 15 Suppl. pp. 231-240 (1994) (Abstract Only).

Lockwood et al., "Partial and complete regression of breast cancer in patients in relation to dosage of coenzyme Q10", Biochem-Biophys-Res-Commun., 199(3), pp. 1504-1508 (1994) (Abstract Only).

Lockwood et al., "Progress on Therapy of Breast Cancer with Vitamin Q10 and the Regression of Metastases", Biochem-Biophys-Res-Commun., 212(1) pp. 172-177 (1995) (Abstract Only).

Mura et al., "Evaluation of transcutol as a clonazepam transdermal permeation enhancer from hydrophillic gel formulations," Eur. J. Pharm. Sci., 2000, 9: 365-372.

Panwar et al., "Preparation, characterization, and in vitro release study of albendazole-encapsulated nanosize liposomes. 2010, International Journal of Nanomedicine, 5: 101-108".

Rastogi, "Analytical control of preservative labelling on skin creams," Contact Dermatitis, 2000, 43: 339-343, Abstract.

Supplemental European Search Report issued in European Patent Application No. 08857192.2 dated Sep. 6, 2013.

Supplementary European Search Report from Application No. EP 05 71 1599 dated Apr. 10, 2008.

Zhang et al., Preparation and Physico-chemical Property of Coenzyme Q10 Submicroemulsion, 2007, China Pharmacy, 18 (19): 1476-1478.

Zucker et al., "Liposome drug's loading efficiency: a working model based on loading conditions and drug's physicochemical properties. 2009, Journal of Controlled Disease, 139: 73-80".

Trosko, J.E., "Mechanism of up-regulated gap junctional intercellular communication during chemoprevention and chemotherapy of cancer", Mutation Research,480-481, pp. 219-229, 2001.

Gura, "Systems for identifying new drugs are often faulty," 1997, Science, 278(5340): 1041-1042.

Frijhoff et al., "Advances in Molecular Carcinogenesis: Current and Future Use of Mouse Models to Screen and Validate Molecularly Targeted Anticancer Drugs," 2004, Molecular Carcinogenesis, 39: 183-194.

Lesperance et al., "Mega-dose vitamins and minerals in the treatment of non-metastatic breast cancer: an historical cohort study," 2002, Breast Cancer Res. Treat., 76:137-143, Abstract.

* cited by examiner

Fig. 1 lyophilization of forms R, A, O and C in order as depicted from left to right.
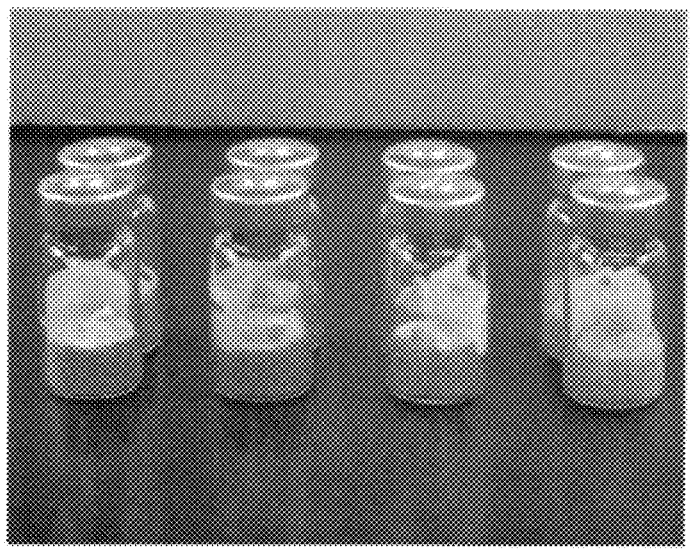
Fig. 2 lyophilization of forms G, Q, S and T in order as depicted from left to right.

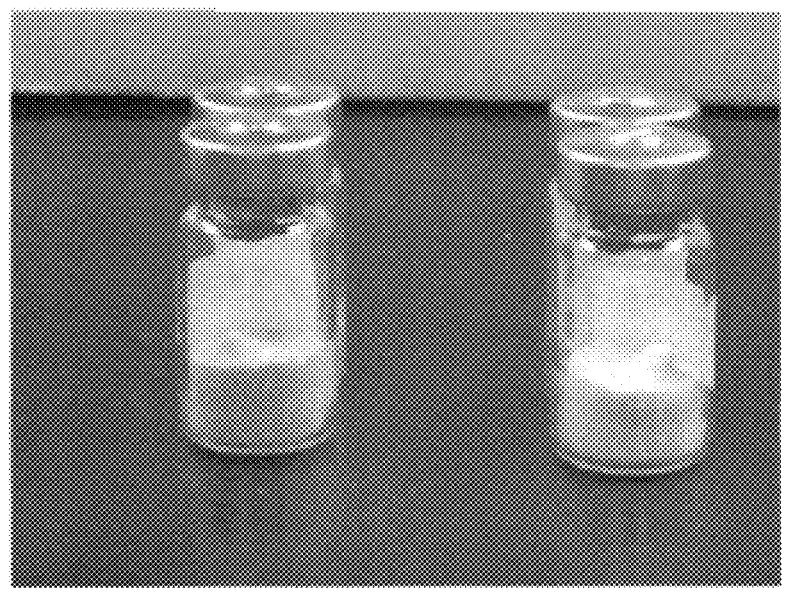
Fig. 3 lyophilization of forms U and V in order as depicted from left to right.
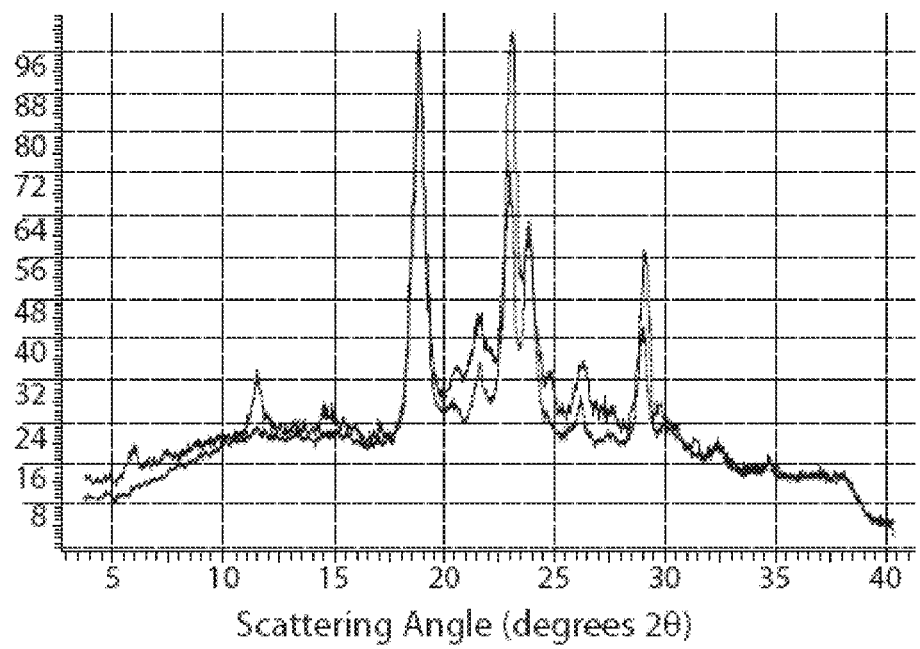
XRPD pattern obtained for "Form A 40 pass" lyophile sample (black trace) and XRPD pattern of CoQ10 bulk drug substance (red trace). The pattern has been normalized so that the intensity of the most intense peak equals 100%.
Fig. 4

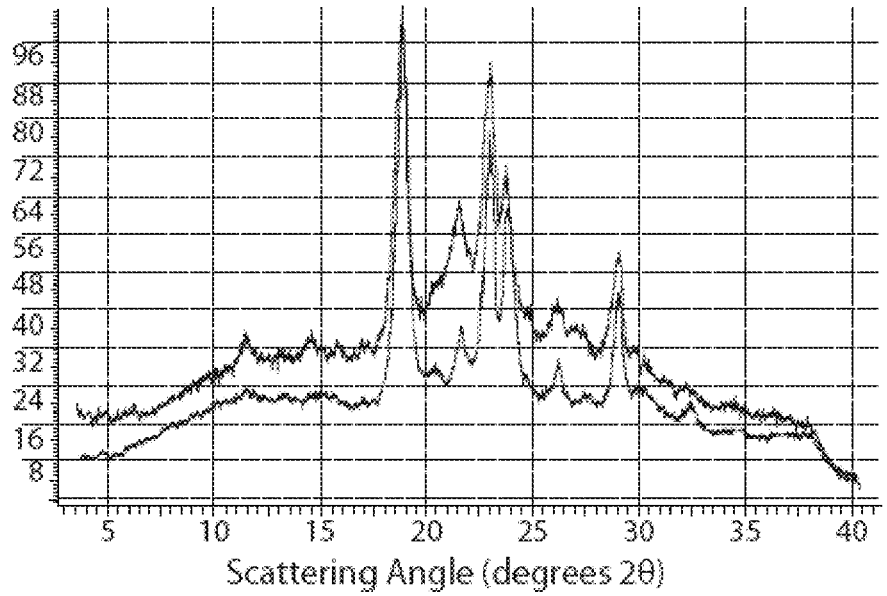

XRPD pattern obtained for "Form C 20 pass" lyophile sample (black trace) and XRPD pattern of CoQ10 bulk drug substance (red trace). The pattern has been normalized so that the intensity of the most intense peak equals 100%.

Fig. 5

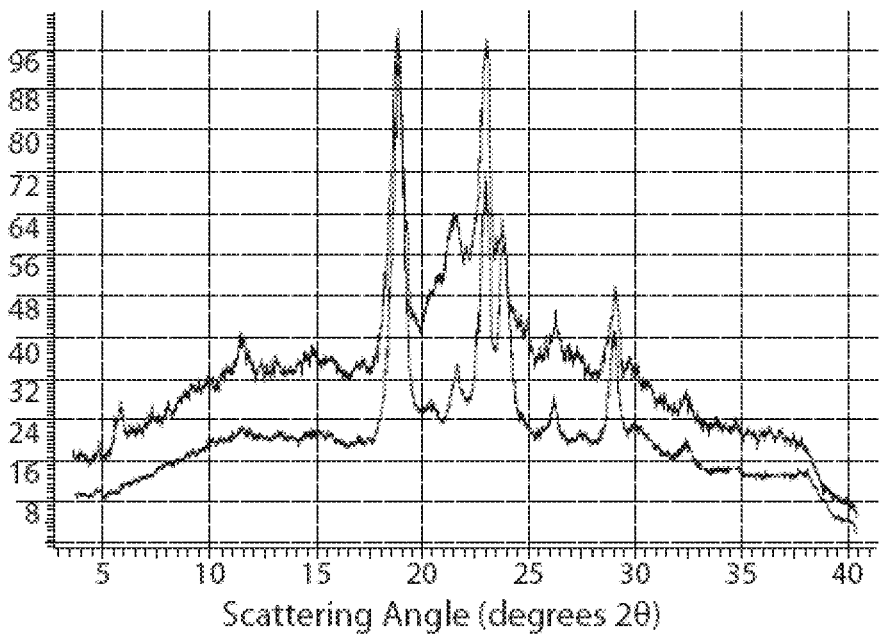

XRPD pattern obtained for "Form G 20 pass" lyophile sample (black trace) and XRPD pattern of CoQ10 bulk drug substance (red trace). The pattern has been normalized so that the intensity of the most intense peak equals 100%.

Fig. 6

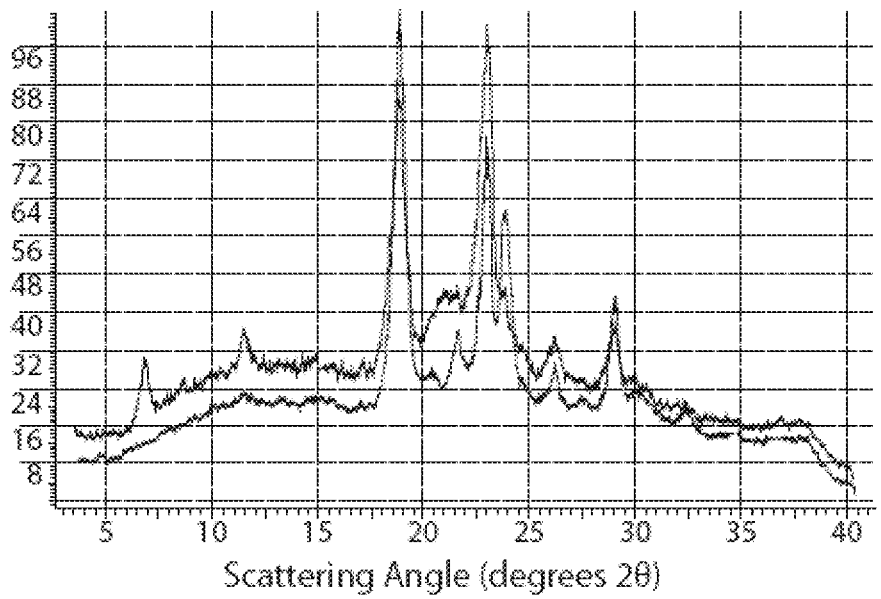

XRPD pattern obtained for "Form O 20 pass" lyophile sample (black trace) and XRPD pattern of CoQ10 bulk drug substance (red trace). The pattern has been normalized so that the intensity of the most intense peak equals 100%.

Fig. 7

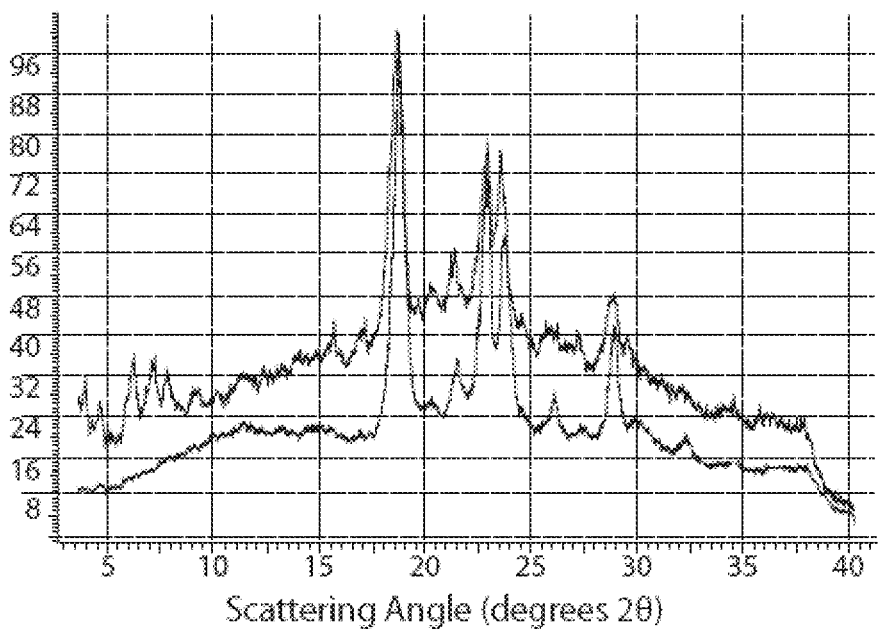

XRPD pattern obtained for "Form Q 20 pass" lyophile sample (black trace) and XRPD pattern of CoQ10 bulk drug substance (red trace). The pattern has been normalized so that the intensity of the most intense peak equals 100%.

Fig. 8

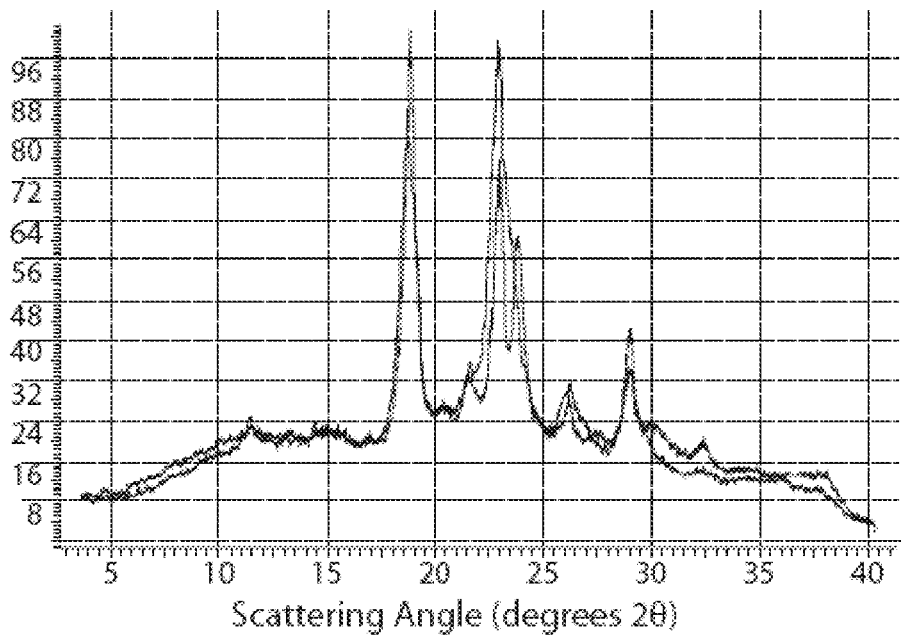

XRPD pattern obtained for "Form R 20 pass" lyophile sample (black trace) and XRPD pattern of CoQ10 bulk drug substance (red trace). The pattern has been normalized so that the intensity of the most intense peak equals 100%.

Fig. 9

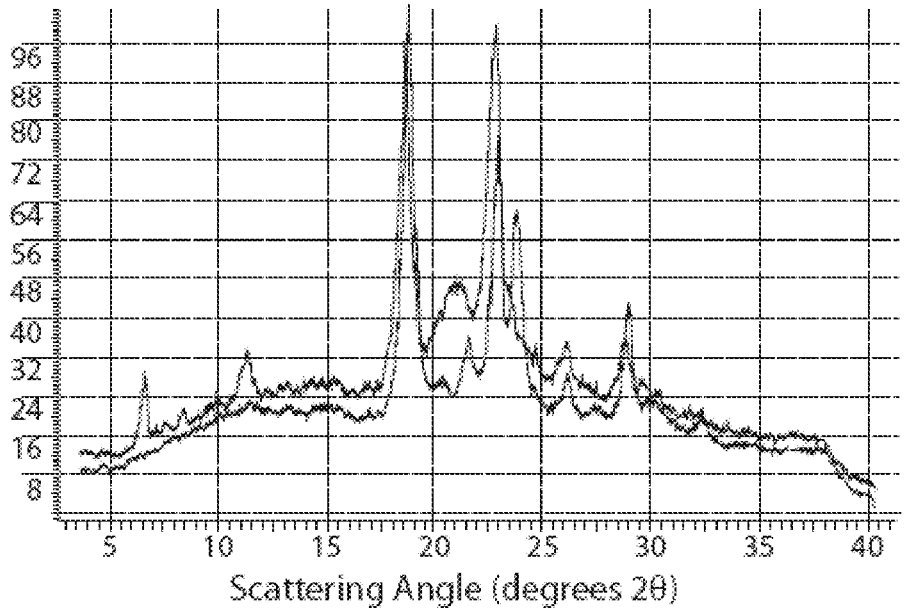

XRPD pattern obtained for "Form S 20 pass" lyophile sample (black trace) and XRPD pattern of CoQ10 bulk drug substance (red trace). The pattern has been normalized so that the intensity of the most intense peak equals 100%.

Fig. 10

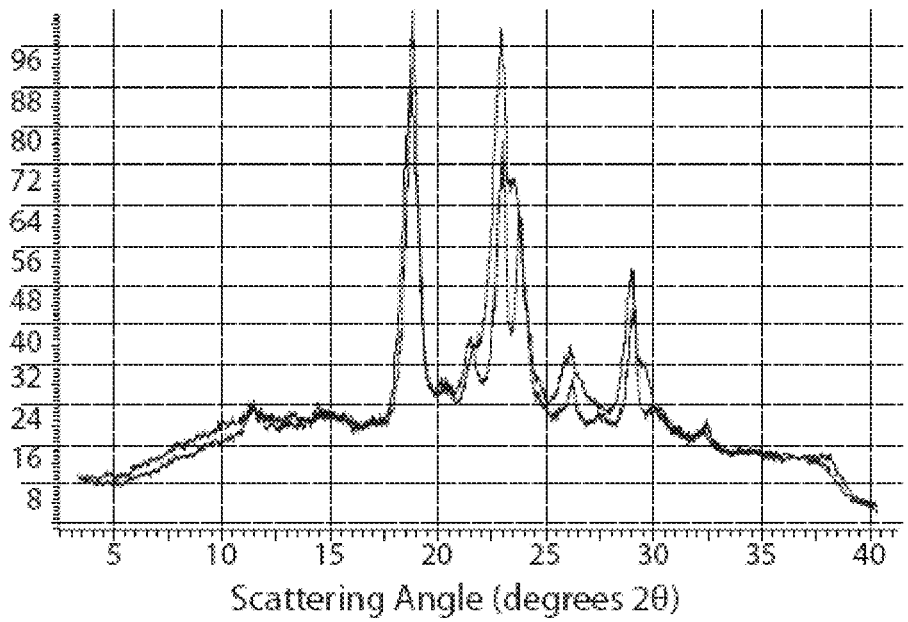

XRPD pattern obtained for "Form T 20 pass" lyophile sample (black trace) and XRPD pattern of CoQ10 bulk drug substance (red trace). The pattern has been normalized so that the intensity of the most intense peak equals 100%.

Fig. 11

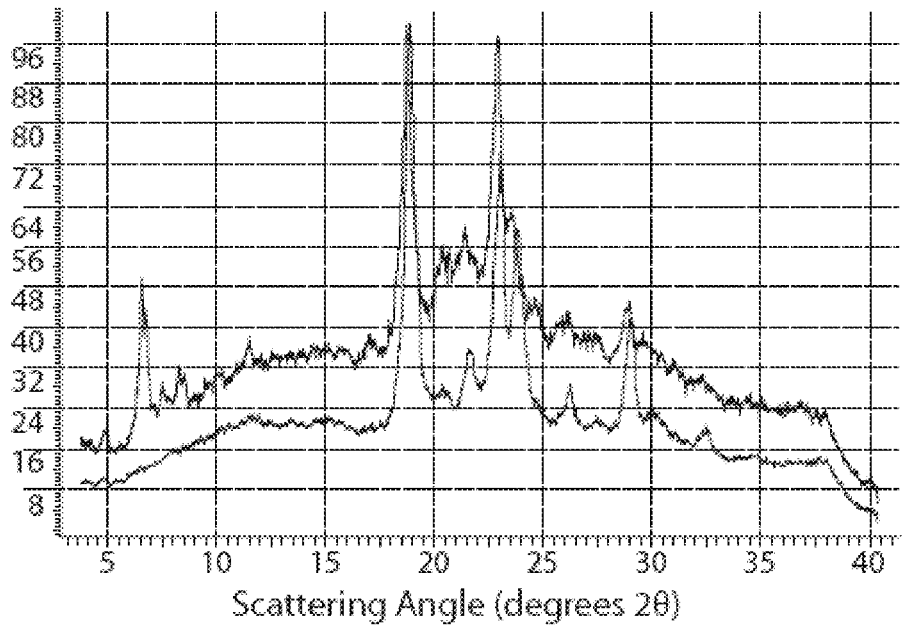

XRPD pattern obtained for "Form U 20 pass" lyophile sample (black trace) and XRPD pattern of CoQ10 bulk drug substance (red trace). The pattern has been normalized so that the intensity of the most intense peak equals 100%.

Fig. 12

XRPD pattern obtained for "Form V 20 pass" lyophile sample (black trace) and XRPD pattern of CoQ10 bulk drug substance (red trace). The pattern has been normalized so that the intensity of the most intense peak equals 100%.

Effect of number of passes on particle size.
5g of Cytotech31510, 3g of DMPC, and 92 ml of water.
The MFz model — M-110P. Processing chamber — F32Y.
Maximum pressure - 25,000 PSI

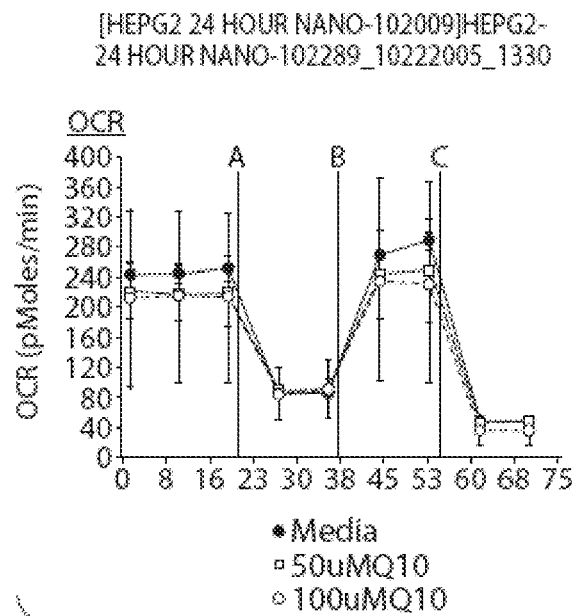
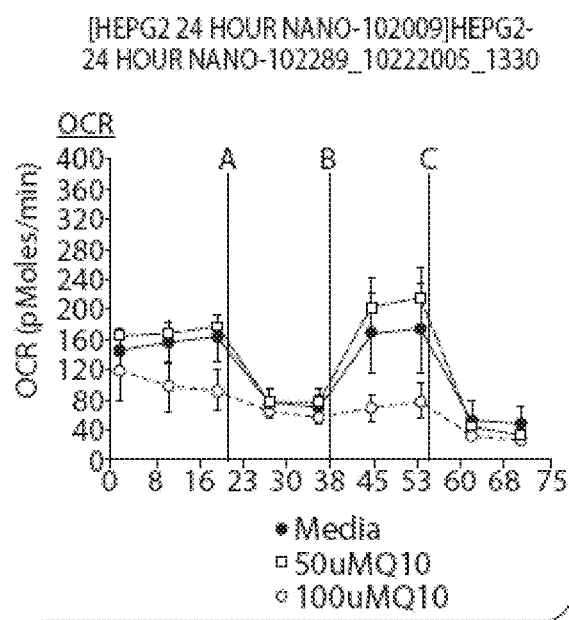
Fig. 26
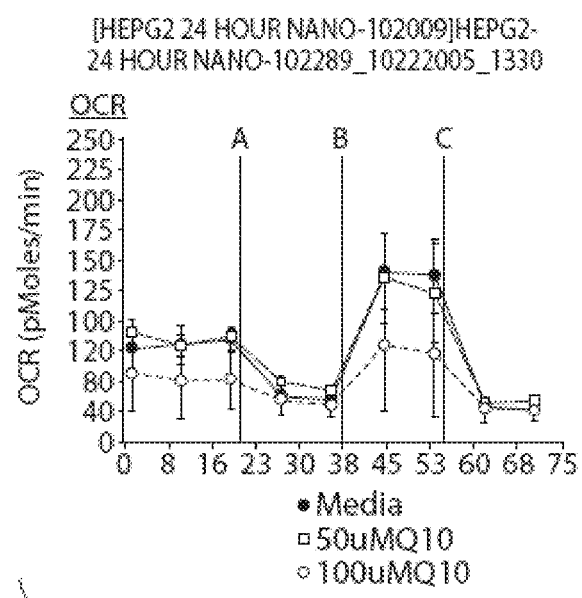
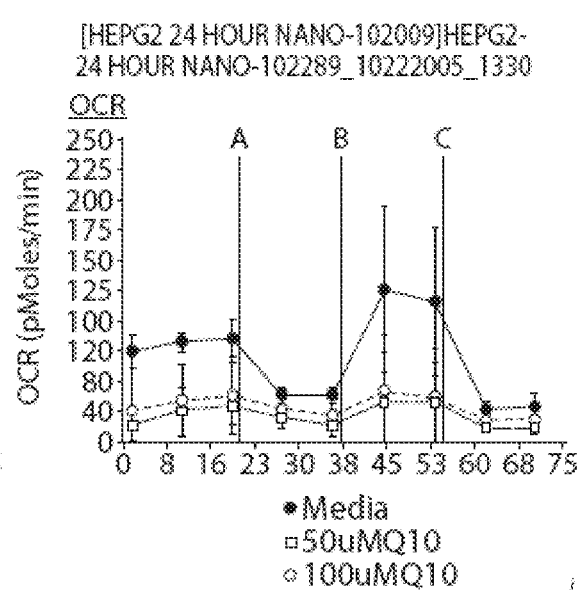
Fig. 27

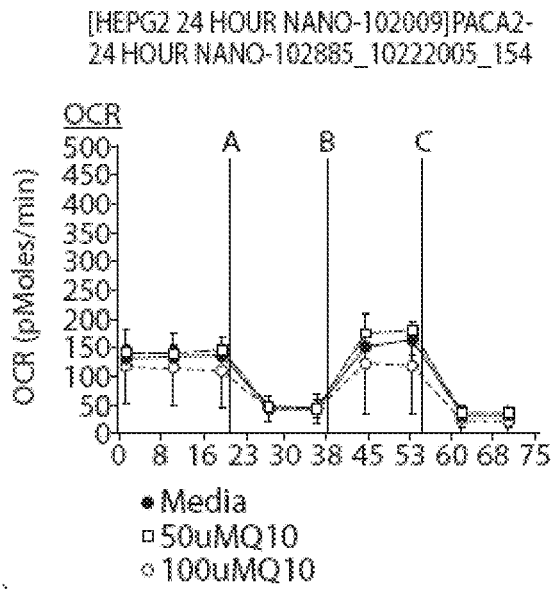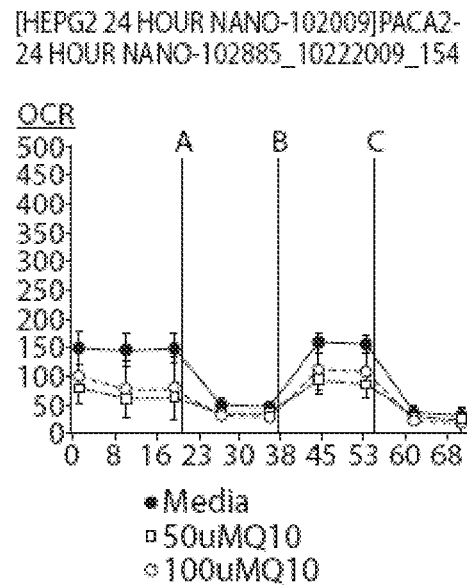
Fig. 28
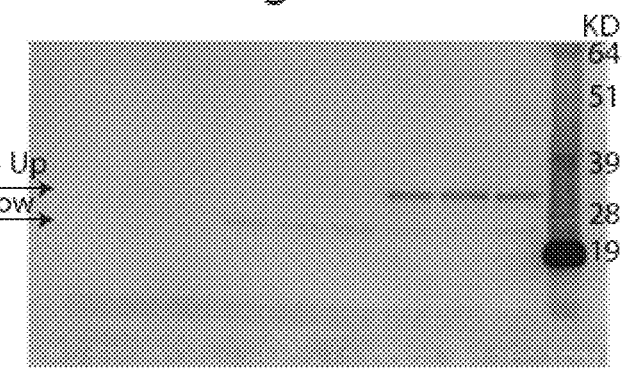
Fig. 29
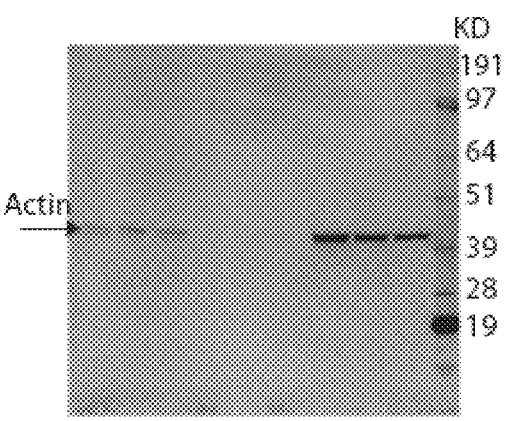
Fig. 30

As can be seen, all animals were dead by approximately day 21.

As can be seen, the same was observed with the group receiving saline, without a change in survival rates.

There was a prolongation of life by approximately 15 days by the excipient control. This does not indicate a therapeutic effect per se, rather, a palliative effect parallel to what is observed in humans with life prolongation.

At 0.5 mg/kg 31510, there was an increase in survival days by 10 days.

In this group there was a statistically significant prolongation of life or approximately 20 days. Animals were found in better health, with less signs of moribundity.

The results with this dosage are truly impressive. Survival was enhanced significantly. The three surviving animals sacrificed on day 60, each had a small tumor.

Thus far, these are the most striking findings. Deaths at day 31 were minimal and prolongation of life was statistically significant. Moreover, at this dose survival rates at day 60 were significantly increased, with approximately 60% of animals alive and only four animals exhibiting visible tumors.

INTRAVENOUS FORMULATIONS OF COENZYME Q10 (COQ10) AND METHODS OF USE THEREOF

RELATED APPLICATIONS

This application claims priority to Provisional Application Ser. No. 61/313,632 entitled "Intravenous Formulations of Coenzyme Q10 (CoQ10) and Methods of Use Thereof", filed on Mar. 12, 2010, and Provisional Application Ser. No. 61/385,107 entitled "Intravenous Formulations of Coenzyme Q10 (CoQ10) and Methods of Use Thereof", filed on Sep. 21, 2010, the entire contents of each of which are expressly incorporated herein by reference.

BACKGROUND

Cancer is presently one of the leading causes of death in developed nations. Although recent research has vastly increased our understanding of many of the molecular mechanisms of tumorigenesis and has provided numerous new avenues for the treatment of cancer, standard treatments for most malignancies remain gross resection, chemotherapy, and radiotherapy. While increasingly successful, each of these treatments may cause numerous undesired side effects. For example, surgery may result in pain, traumatic injury to healthy tissue, and scarring. Radiotherapy and chemotherapy may cause nausea, immune suppression, gastric ulceration and secondary tumorigenesis. Improved methods for the treatment of diseases, including cancer, and compositions capable of delivering bioactive agents to aid in the treatment of diseases and other conditions remain desirable.

Approximately 60% of all drugs administered to patients in hospitals, for conditions including cancer, are given in the form of injections. Intravenous formulations now have a major role as vehicles for drugs. Intravenous formulations are finding a greater use in the administration of drugs, because of dependability, accuracy, convenience, avoidance of the gastric irritation potential of orally administered drugs, and the importance of continuous as well as intermittent drug therapy. Techniques for providing intravenous administrations have improved steadily in the last decade, and the use of such intravenous formulations has been annually increasing.

International Patent Application Publication No. WO/2009/126764 (filed Apr. 9, 2009) discloses the treatment of cancer with CoQ10. This application is herein incorporated by reference in its entirety.

CoQ10 has a long side chain of 10 isoprenoid units which causes the drug to be extremely lipophilic and practically insoluble in water. The bioavailability of perorally administered CoQ10 is generally extremely low and variable and was found to be related to the dissolution rate of the formulation. As a consequence of the low peroral bioavailability, and its intrinsic high variability, intravenous administration systems are of special interest particularly in the care of cancer patients. Due to its lipophilicity, CoQ10 needs to be incorporated into a carrier for intravenous administration so that its pharmacokinetics are influenced by the carrier system.

Coenzyme Q10, also referred to herein as CoQ10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is found throughout most tissues of the human body and the tissues of other mammals and is concentrated in the mitochondria. CoQ10 is very lipophilic and, for the most part, insoluble in water. The insolubility is related to the 50-carbon atom isoprenoid side chain, of hydrocarbon nature as shown in the following structure of CoQ10.

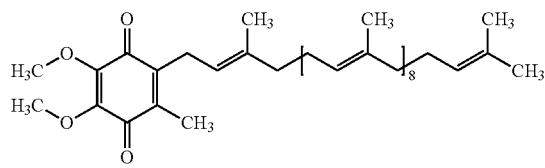

CoQ10, being highly hydrophobic, is essentially insoluble in aqueous solutions. For CoQ10 to be parenterally administered, it must be contained in a stable formulation compatible with, for example, intravenous injection. One approach to prepare an intravenous formulation of CoQ10 in an aqueous medium requires the inclusion of one or more surfactants and other entities which would allow the creation of a dispersion of particles of CoQ10 in an aqueous medium. There are many difficulties associated with this approach. A prominent difficulty is related to the fact that CoQ10 is a solid at temperatures below about 50° C. The dispersion of solid particles of CoQ10 in an aqueous medium involves difficulties in the preparation of a safe formulation with a stability up to about two years for clinical application. Such solid particle dispersions have been explored, but on standing, particles containing CoQ10 fall to the bottom of the container, and redispersion by stirring or shaking does not meet the requirements for medical use. Successful formulations should have a chemical and physical stability of up to about two years and provide accurate dosing for clinical use. The second prominent difficulty is having a formulation which, on intravenous administration, does not lead to particle separation or precipitation within the blood stream. Such a separation would be detrimental to blood flow and potentially be life-threatening.

A number of different formulations with the object to enhance the bioavailability of CoQ10 can be found in the patent literature. Taki and Takahira disclose in EP 23349 (4 Feb. 1981) that the lymphatic absorption of orally administered CoQ10 is increased by coadministration of long-chain fatty acids and monoglycerides. Increase of intestinal absorption by administration of capsules containing oily (surfactant) solutions of CoQ10 is disclosed in different patents such as WO 8604503 A1 (14 Aug. 1986), JP 63188623 A2 (4 Aug. 1988), JP 62067019 A2 (26 Mar. 1987), JP 59148735 A2 (25 Aug. 1984) and JP 56012309 (6 Feb. 1981). Solubilization of CoQ10 in micellar solutions is described in EP 522433 A1 (13 Jan. 1993), WO 8803019 A1 (5 May 1988) and JP 59148718 A2 (25 Aug. 1984). Ueno et al. (Acta Pharm. Nord., 1 (1989) 99-104) report on the increase of peroral bioavailability by inclusion of CoQ10 in a complex with β-cyclodextrins. A similar formulation is disclosed in JP 56109590 A2 (31 Aug. 1981). Moreover, incorporation of CoQ10 in emulsions is reported to enhance intestinal absorption as described, for example, by Yano et al. in EP 494654 A2 (15 Jul. 1992). CoQ10 particles in an amorphous physical state, in particular a super-cooled melt, are described in U.S. Pat. No. 6,197,349 (issued Mar. 6, 2001) and U.S. Pat. No. 6,207,178 (issued Mar. 27, 2001).

For parenteral, in particular intravenous administration CoQ10 has to be incorporated into a carrier vehicle since it is not possible to manufacture an aqueous solution with therapeutic concentrations of CoQ10 due to its lipophilicity. Lecithin stabilized soya oil emulsions for intravenous administration of ubidecarenone are disclosed by Groke and Polzer (DE 3524788 A1, 22 Jan. 1987). Sugio et al. (JP 62123113 A2. 4 Jun. 1987) as well as Mizushima et al. (JP 60199814 A2. 9 Oct. 1985). JP 63319046 A2 (27 Dec. 1988) describes a soya oil emulsion vehicle coated by polysaccharides. The concentrations of CoQ10 which can be incorporated in emulsions are, however, limited due to the relatively poor solubility of CoQ10 in vegetable oils.

Liposome preparations of egg lecithin and cholesterol containing ubidecarenone are disclosed in EP 69399 A2 (12 Jan. 1983). Polysaccharide-modified liposomes are described e.g. in EP 94692 A1 (23 Nov. 1983), JP 60001124 A2 (7 Jan. 1985) and JP 63313727 A2 (21 Dec. 1988).

However, the disadvantage of incorporating a drug into a carrier system might be that an undesired change and/or significant variability in the pharmacokinetics of the substance will be caused because the biodistribution is influenced by the biodistribution of the carrier, its RES activity and drug release from the carrier vehicle. Bogentoft et al. (in Folkers K., Littaru G. P., Yamagami T., (Eds.), Biomedical and Clinical Aspects of Coenzyme Q. Vol. 6. Elsevier 1991, pp. 215-224) observed that ubidecarenone accumulates in the RES organs when administered intravenously in a mixed micellar system or an emulsion vehicle, respectively. Furthermore, the solubility of the bioactive substance in the carrier is often too low to obtain therapeutic doses in acceptable volumes of the formulation. In addition, toxic side effects of the carrier particles by themselves have been discussed in the literature inter alia for parenteral lipid emulsions (Hajri T. et al., Biochim. Biophys. Acta 1047 (1990) 121-130; Connelly P. W. et al.; Biochim. Biophys. Acta 666 (1981) 80-89; Aviram M. et al., Biochem. Biophys. Res. Commun. 155 (1988) 709-713; Singh M. et al.; J. Parenter. Sci. Technol. 40 (1986) 34-40; Cotter R. et al., Am J. Clin. Nutr. 41 (1985) 994-1001; Untracht S., Biochim. Biophys. Acta711 (1982) 176-192).

CoQ10 is a problematic substance with regard to pharmaceutical formulations of this drug. For pharmaceutical IV preparations of CoQ10, where it is necessary to reduce the particle size, traditional methods have been unsuccessful. For example, micronization of the material has not been possible using ball-mill, hammer mill, jet mill, or cryogenic milling etc., due to the non-friable nature and low melting point of Coenzyme Q10.

SUMMARY OF THE INVENTION

The present invention comprises a stable and non-toxic CoQ10 formulation suitable for intravenous administration to a subject to produce clinically effective blood levels of Coenzyme Q10 (also referred to as CoQ10 or Q10 herein).

The present invention also comprises a method for preparing a stable and non-toxic CoQ10 formulation suitable for intravenous administration to a subject to produce clinically effective blood levels of CoQ10.

In certain non-limiting embodiments of the invention claimed herein, a therapeutic formulation suitable for intravenous administration to a subject is presented. In certain embodiments, the therapeutic formulation includes an aqueous solution; a hydrophobic active agent dispersed to form a colloidal nano-dispersion of particles; and at least one of a dispersion stabilizing agent and an opsonization reducer.

The colloidal nano-dispersion of the active agent is dispersed into nano-dispersion particles having sizes of less than 200-nm. In some embodiments the dispersion stabilizing agent is selected from natural or semisynthetic phospholipids. For example, suitable stabilizing agents include Polyethoxylated (a/k/a pegylated) castor oil (Cremophor® EL), Polyethoxylated hydrogenated castor oil (Cremophor® RH 40), Tocopherol polyethylene glycol succinate (Pegylated vitamin E, Vitamin E TPGS), Sorbitan fatty acid esters (Spans®), Bile acids and bile-acid salts or Dimyristoylphosphatidyl choline (DMPC). In some embodiments the stabilizing agent is DMPC.

In certain embodiments, the opsonization reducer is selected from poloxamines and poloxamers. Suitable poloxamers include poloxamer 188. In some embodiments, the opsonization reducer is poloxamer 188.

In some embodiments, the hydrophobic active agent is Coenzyme Q10 (i.e., CoQ10, ubidecarenone, ubiquinone, etc.).

In some embodiments, the hydrophobic active agent is CoQ10, the opsonization reducer is poloxamer 188 and the dispersion stabilizing agent is DMPC.

In certain embodiments, the colloidal nano-dispersion is a suspension.

In certain embodiments, the colloidal nano-dispersion is an emulsion.

In some embodiments, the active agent of the colloidal nano-dispersion is in a crystalline form.

In some embodiments, the active agent of the colloidal nano-dispersion is in a super-cooled melt form.

Embodiments are also provided wherein the formulation has a weight-per-volume of CoQ10, DMPC and poloxamer of 4%, 3% and 1.5%, respectively. In other embodiments, the weight-per-volume of CoQ10, DMPC and poloxamer is 8%, 6% and 3.0%, respectively.

In some embodiments, the mean size of the nano-dispersion particles is between about 10-nm and about 200-nm.

In some embodiments, the mean size of the nano-dispersion particles is between about 10-nm and about 100-nm.

In some embodiments, the mean size of the nano-dispersion particles is between about 30-nm and about 80-nm.

In some embodiments, the mean size of the nano-dispersion particles is between about 35-nm and about 40-nm.

In some embodiments, the mean size of the nano-dispersion particles is less than about 45-nm.

In certain embodiments, the formulation comprises an aqueous solution, a hydrophobic active agent dispersed to form a colloidal nano-dispersion of particles; and at least one of a dispersion stabilizing agent and an opsonization reducer. The colloidal nano-dispersion of the active agent is dispersed into liposomes having sizes of less than 200-nm.

In some embodiments, the dispersion stabilizing agent forms liposomes that are unilamellar. In other embodiments, the liposomes are bi-layered multilamellar liposomes having an aqueous space between the bi-layers and a lipophilic space within the bi-layers. In other embodiments, the hydrophobic active agent is entrapped within the lipophilic space of the bi-layers. In other embodiments, the multilamellar liposome further includes a hydrophilic agent entrapped in the aqueous space between the bi-layers.

In certain embodiments, the formulation comprises an aqueous solution; a hydrophobic active agent dispersed to form a colloidal nano-dispersion of particles; and DMPC and an opsonization reducer. In some embodiments, the opsonization reducer is selected from the group consisting of poloxamer and poloxamines. In some embodiments the opsonization reducer is poloxamer 188. In some embodiments, the hydrophobic active agent is Coenzyme Q10 (CoQ10). In some embodiments, the hydrophobic active agent is Coenzyme Q10 (CoQ10) and the opsonization reducer is poloxamer 188. In some embodiments the formulation has a weight-per-volume of the CoQ10, DMPC and poloxamer 188 of 4%, 3% and 1.5%, respectively. In other embodiments, the formulation has a weight-per-volume of the CoQ10, DMPC and poloxamer 188 of 8%, 6% and 3%, respectively. In some embodiments, the colloidal nano-dispersion is a suspension. In other embodiments, the colloidal nano-dispersion is an emulsion. In some embodiments, the active agent of the colloidal nano-dispersion is in a crystalline form. In other embodiments, the active agent of the colloidal nano-dispersion is in a super-cooled melt form.

In some embodiments, the formulation comprises an aqueous solution; a hydrophobic active agent dispersed to form a colloidal nano-dispersion of particles; and DMPC. The colloidal nano-dispersion of the active agent is dispersed into nano-dispersion particles having a mean size of less than 200-nm. In some embodiments, the hydrophobic active agent is Coenzyme Q10 (CoQ10). In some embodiments the colloidal nano-dispersion is a suspension. In other embodiments, the colloidal nano-dispersion is an emulsion. In some embodiments, the active agent of the colloidal nano-dispersion is in a crystalline form. In other embodiments, the active agent of the colloidal nano-dispersion is in a super-cooled melt form. In some embodiments, the formulation has a weight-per-volume of the CoQ10 and DMPC of 4% and 3%, respectively. In other embodiments the weight-per-volume of the CoQ10 and DMPC is 8% and 6%, respectively. In some embodiments, the mean size of the nano-dispersion particles is between about 10-nm and about 200-nm. In other embodiments, the mean size of the nano-dispersion particles is between about 10-nm and about 100-nm. In other embodiments, the mean size of the nano-dispersion particles is between about 30-nm and about 80-nm. In other embodiments, the mean size of the nano-dispersion particles is between about 35-nm and about 40-nm. In other embodiments, the mean size of the nano-dispersion particles is less than about 45-nm.

In certain embodiments, the formulation comprises an aqueous solution; CoQ10 dispersed to form a colloidal nano-dispersion of particles; a dispersion stabilizing agent selected from the group consisting of pegylated castor oil, Cremophor EL, Cremophol RH40, pegylated vitamin E TPGS and Dimyristoylphosphatidyl choline (DMPC); and an opsonization reducer selected from the group consisting of poloxamer and poloxamines. The colloidal nano-dispersion of CoQ10 is dispersed into nano-dispersion particles having a mean size between about 10-nm and about 100-nm.

In certain embodiments, the formulation comprises an aqueous solution; CoQ10 dispersed to form a colloidal nano-dispersion of particles; DMPC; and poloxamer 188. The colloidal nanodispersion of CoQ10 is dispersed into nano-dispersion particles having a mean size of between 30-nm and 80-nm.

In certain embodiments, methods are provided for the preparation of a CoQ10 nano-dispersion suitable for intravenous administration. In some embodiments, the method comprises dispersing the hydrophobic active agent by high pressure homogenization by (1) adding a hydrophobic active agent to a 65° C. bath of water and mixing to form a hydrophobic active agent/water mixture; (2) adding a dispersion stabilizing agent to the hydrophobic active agent/water mixture and mixing at 65° C. to form a hydrophobic active agent/water/stabilizer mixture; (3) adding an opsonization reducer to form a hydrophobic active agent/water/stabilizer/reducer mixture; (4) pre-heating a Microfluidizer to 65° C.; and (5) processing by mixing the hydrophobic active agent/water/stabilizer/reducer mixture in the Microfluidizer at 65° C. such that a hydrophobic active agent colloidal nano-dispersion having a mean particle size of less than 200-nm is formed.

In some embodiments, the method further comprises the step of lyophilizing the colloidal nano-dispersion to crystallize the CoQ10 colloidal nano-dispersion particles.

In some embodiments, the method further comprises the step of adding a lyoprotectant. In some embodiments, the lyoprotectant is a nutritive sugar. In some embodiments, the nutritive sugar is selected from the group consisting of lactose, mannose, maltose, galactose, fructose, sorbose, raffinose, neuraminic acid, glucosamine, galactosamine, N-methylglucosamine, mannitol, sorbitol, arginine, glycine and sucrose.

In some embodiments, the method includes a dispersion stabilizing agent selected from the group consisting of pegylated castor oil, Cremophor EL, Cremophor RH40, pegylated vitamin E, vitamin E TPGS and Dimyristoylphosphatidyl choline (DMPC). In some embodiments, the dispersion stabilizing agent is DMPC. In some embodiments, the opsonization reducer is selected from the group consisting of poloxamer and poloxamines. In some embodiments, the opsonization reducer is poloxamer 188. In some embodiments the opsonization reducer is poloxamer 188 and the dispersion stabilizing agent is DMPC. In some embodiments, the hydrophobic active agent is CoQ10. In some embodiments the hydrophobic active agent is CoQ10, the opsonization reducer is poloxamer 188 and the dispersion stabilizing agent is DMPC. In some embodiments, the CoQ10 of the colloidal nano-dispersion is in the form of a super-cooled melt. In other embodiments, the CoQ10 of the colloidal nano-dispersion is in a crystalline form.

In some embodiments, the formulation resulting from present methods comprises an aqueous solution; a hydrophobic active agent dispersed to form a colloidal nano-dispersion of particles; and at least one of a dispersion stabilizing agent and an opsonization reducer. The colloidal nano-dispersion of the active agent is dispersed into nano-dispersion particles having a mean particle size of less than 200-nm. In some embodiments, the weight-per-volume of CoQ10, DMPC and poloxamer 188 is 4%, 3% and 1.5%, respectively. In other embodiments, the weight-per-volume of the CoQ10, DMPC and poloxamer 188 is 8%, 6% and 3%, respectively. In some embodiments, the hydrophobic active agent colloidal nano-dispersion has a mean particle size of between about 10-nm and about 100-nm. In other embodiments, the hydrophobic active agent colloidal nano-dispersion has a mean particle size between about 35-nm and 40-nm. In other embodiments, the hydrophobic active agent colloidal nano-dispersion has a mean particle size of less than 45-nm.

In one embodiment, the formulation is diluted prior to use with a standard pharmaceutical parenteral diluent that is iso-osmotic with blood. Non-limiting examples of a suitable parenteral diluent include N saline, 5% dextrose, lactated ringer's solution, and phosphate buffered saline (PBS). The diluted formulation, i.e., infusion, may be administered over a 4 hour or shorter period. The infusion may be administered intermittently or continuously as a slow drip or by metered pumping systems. Such infusion may be filtered in line prior to use with a filter, such as a 1-5 micron filter. In some embodiments, the formulation is made as a sterile product for infusion, where sterilization is achieved by filtration, autoclaving, radiation or the like. Various methods of sterilization are known in the art. In one embodiment, the formulation is prepared such that it is free of endotoxin. In one embodiment, the formulation is prepared such that it is free of organisms that may case transmissible spongiform encephalitis (BSE/TSE).

Methods are also provided herein for the treatment or prevention of oncological disorders in a subject. In some embodiments, the method of treating or preventing an oncological disorder in a subject comprises intravenously administering a therapeutic formulation, as described herein, to a subject such that treatment or prevention of the oncological disorder occurs. In some embodiments, the intravenous administration is via a dose selected for providing efficacy in the subject for the oncological disorder being treated. In some embodiments, the oncological disorder is an aggressive or metastatic oncological disorder. In some embodiments, the aggressive or metastatic oncological disorder is selected from the group consisting of pancreatic carcinoma, hepatocellular carcinoma, Ewing's sarcoma, metastatic breast cancer, metastatic melanoma, brain cancer (astrocytoma glioblastoma), neuroendocrine cancer, colon cancer, lung cancer, osteosarcoma, androgen-independent prostate cancer, ovarian cancer and non-Hodgkin's Lymphoma. In other embodiments, the oncological disorder is a non-aggressive oncological disorder. In some embodiments the non-aggressive oncological disorder is selected from the group consisting of non-metastatic breast cancer, androgen-dependent prostate cancer, small cell lung cancer and acute lymphocytic leukemia.

In some embodiments of the method of treatment, the formulation comprises about 4% of Coenzyme A10, about 3% DMPC and about 1.5% poloxamer 188.

In certain embodiments, methods are provided for inhibiting tumor cell growth in a subject. In some embodiments, the method comprises intravenously administering a therapeutic formulation, as described herein, to a subject such that tumor cell growth is inhibited. In some embodiments, the intravenous administration is via a dose selected for providing efficacy in inhibiting tumor cell growth in the subject. In some embodiments, the formulation comprises about 4% of Coenzyme Q10, about 3% of DMPC and about 1.5% of poloxamer 188.

In some embodiments, the oncological disorder is an oncological condition related to or associated with the disregulation of the Bcl-2 family of proteins.

BRIEF DESCRIPTION OF THE DRAWINGS

Various embodiments of the present disclosure will be described herein below with reference to the figures wherein:

FIG. 1 depicts lyophilized samples of CoQ10 nano-particles labeled as Forms R, A, O and C as depicted from left to right where Forms R, O and C were subjected to 20 passes each through the homogenization process, while Form A was subject to 40 passes through the homogenization process.

FIG. 2 depicts lyophilized samples of CoQ10 nano-particles labeled as Forms G, Q, S and T as depicted from left to right where Forms G, Q, S and T were subjected to 20 passes each through the homogenization process.

FIG. 3 depicts lyophilized samples of CoQ10 nano-particles labeled as Forms U and V as depicted from left to right where Forms U and V were subjected to 20 passes each through the homogenization process.

FIG. 4 depicts XRDP patterns for lyophilized sample Form A and superimposed with the pattern obtained from the CoQ10 bulk substance.

FIG. 5 depicts XRDP patterns for lyophilized sample Form C and superimposed with the pattern obtained from the CoQ10 bulk substance.

FIG. 6 depicts XRDP patterns for lyophilized sample Form G and superimposed with the pattern obtained from the CoQ10 bulk substance.

FIG. 7 depicts XRDP patterns for lyophilized sample Form 0 and superimposed with the pattern obtained from the CoQ10 bulk substance.

FIG. 8 depicts XRDP patterns for lyophilized sample Form Q and superimposed with the pattern obtained from the CoQ10 bulk substance.

FIG. 9 depicts XRDP patterns for lyophilized sample Form R and superimposed with the pattern obtained from the CoQ10 bulk substance.

FIG. 10 depicts XRDP patterns for lyophilized sample Form S and superimposed with the pattern obtained from the CoQ10 bulk substance.

FIG. 11 depicts XRDP patterns for lyophilized sample Form T and superimposed with the pattern obtained from the CoQ10 bulk substance.

FIG. 12 depicts XRDP patterns for lyophilized sample Form U and superimposed with the pattern obtained from the CoQ10 bulk substance.

DMPC:poloxamer 188 in comparison to chemotherapy alone and in combination with chemotherapy.

Figure 25:
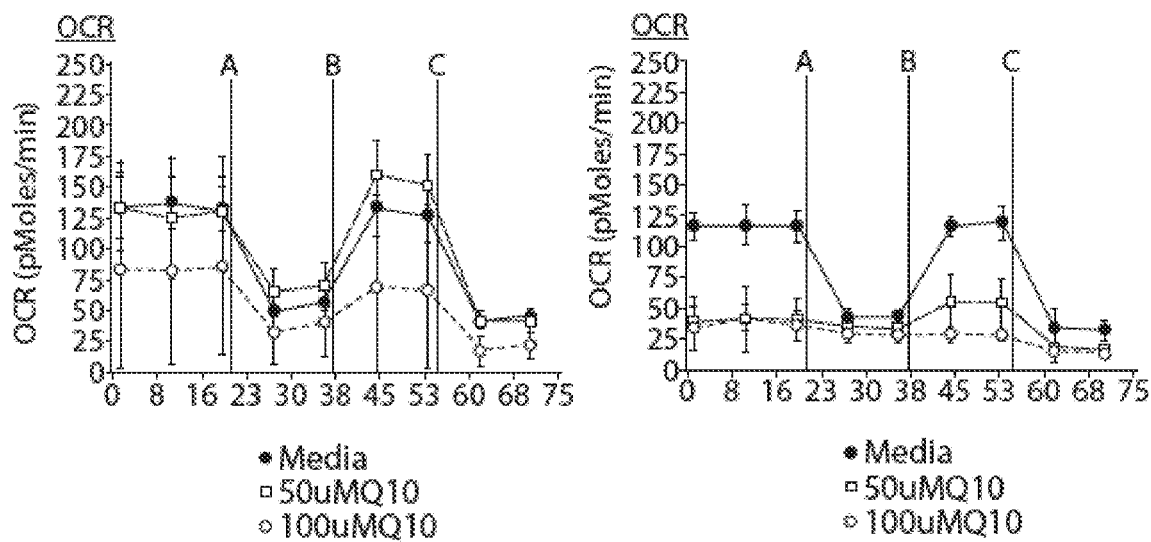

FIG. 25 depicts, in graphical form using OCR as a readout, the effects of two CoQ10 N formulations on HepG2 cells. Formulation I was 4:3:0 CoQ10:DMPC:poloxamer 188 and formulation II was 4:3:1.5 CoQ10:DMPC:poloxamer 188.

FIG. 26 depicts, in graphical form using OCR as a readout, the effects of two CoQ10 N formulations on MCF-7 cells. Formulation I was 4:3:0 CoQ10:DMPC:poloxamer 188 and formulation II was 4:3:1.5 CoQ10:DMPC:poloxamer 188.

FIG. 27 depicts, in graphical form using OCR as a readout, the effects of two CoQ10 N formulations on PC-3 cells. Formulation I was 4:3:0 CoQ10:DMPC:poloxamer 188 and formulation II was 4:3:1.5 CoQ10:DMPC:poloxamer 188.

FIG. 28 depicts, in graphical form using OCR as a readout, the effects of two CoQ10 IV formulations on PaCa2 cells. Formulation I was 4:3:0 CoQ10:DMPC:poloxamer 188 and formulation II was 4:3:1.5 CoQ10:DMPC:poloxamer 188.

FIG. 29 depicts western blots to determine the level of caspase in gel 1, 24 hours after treatment.

FIG. 30 depicts western blots to determine the level of actin in gel 1, 24 hours after treatment.

Figure 31:
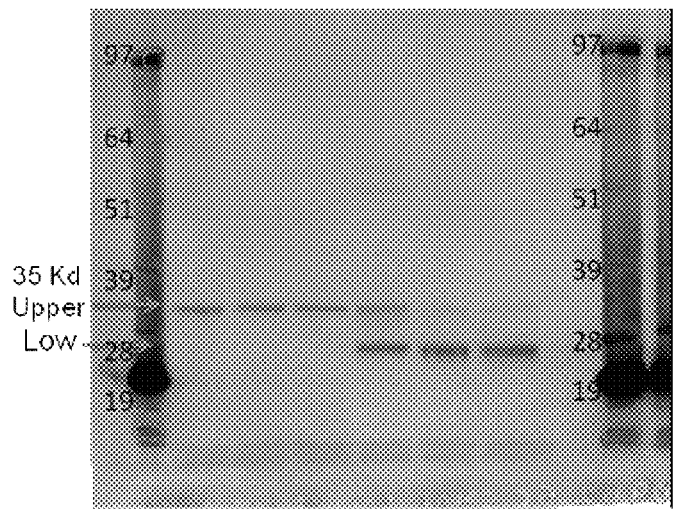

FIG. 31 depicts western blots to determine the level of caspase in gel 2, 24 hours after treatment.

Figure 32:
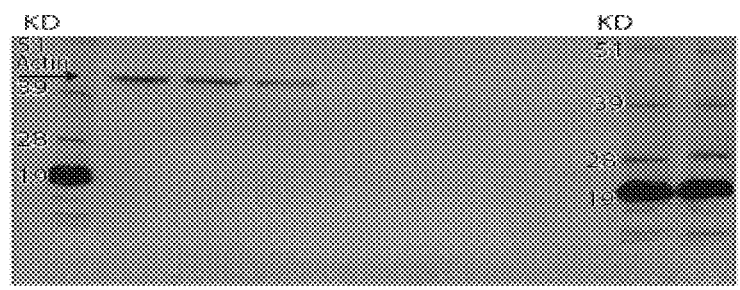

FIG. 32 depicts western blots to determine the level of actin in gel 2, 24 hours after treatment.

Figure 33:
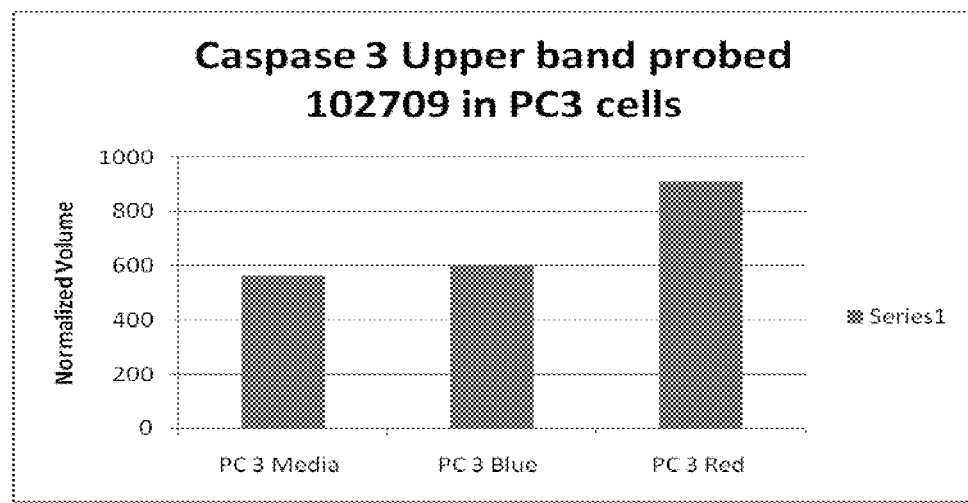

FIG. 33 depicts normalized Caspase 3 protein levels observed in PC3.

Figure 34:
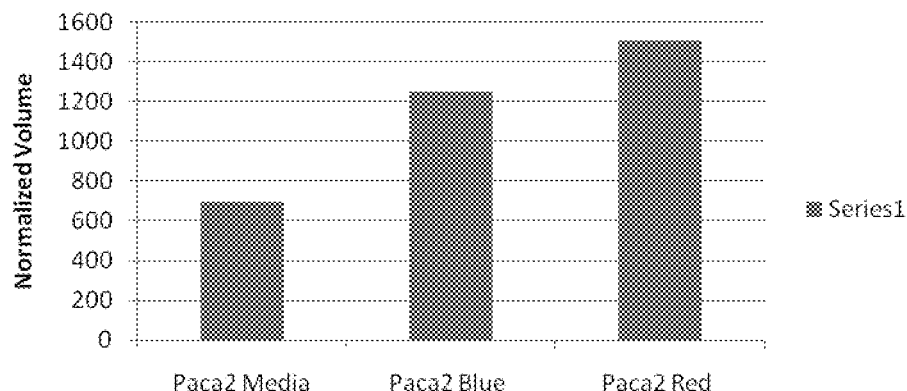

FIG. 34 depicts normalized Caspase 3 protein levels observed in PaCa2.

Figure 35:
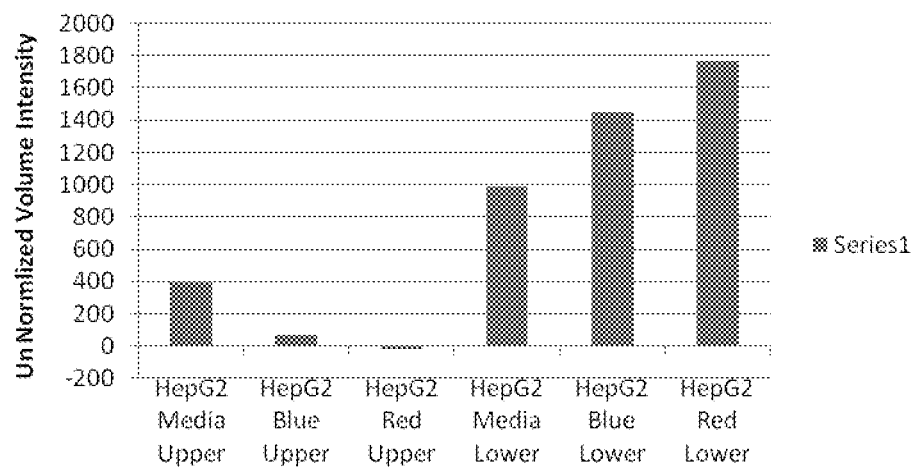

FIG. 35 depicts un-normalized Caspase 3 protein levels observed in HepG2 cells.

Figure 36:
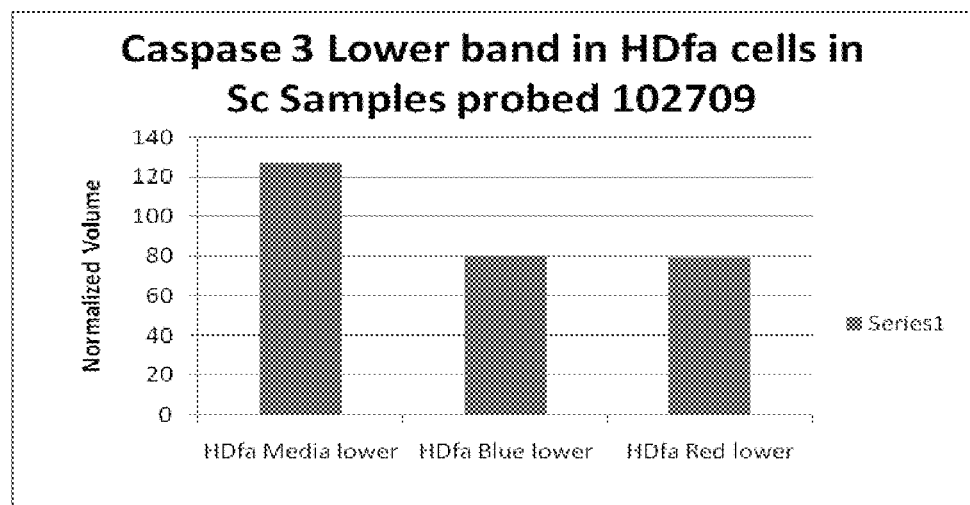

FIG. 36 depicts normalized Caspase 3 protein levels observed in HDfa cells.

Figure 37:
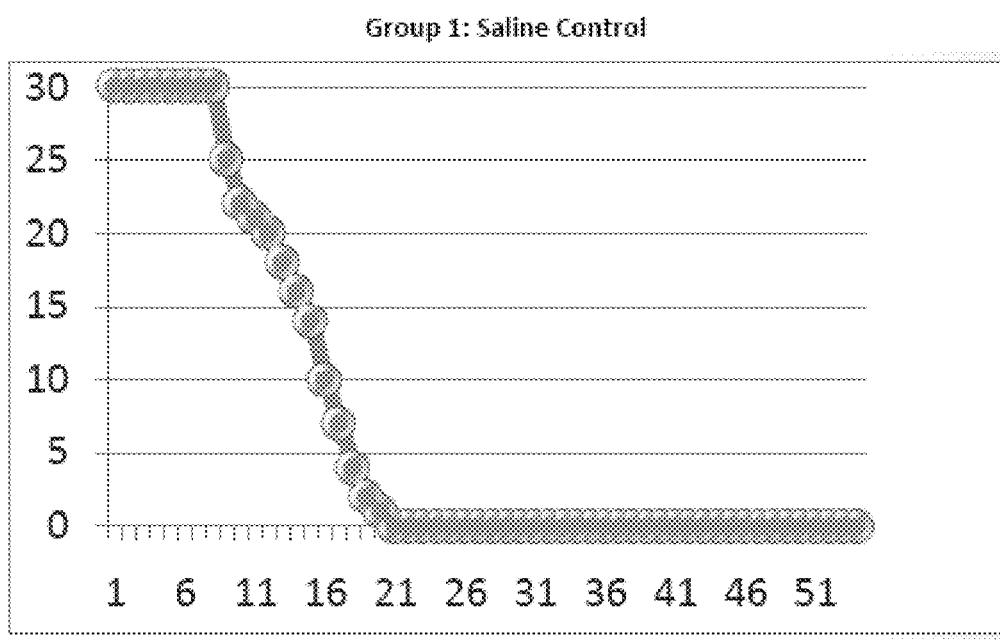

FIG. 37 depicts the results of untreated NSG mice in a MiaPACA2 study.

Figure 38:
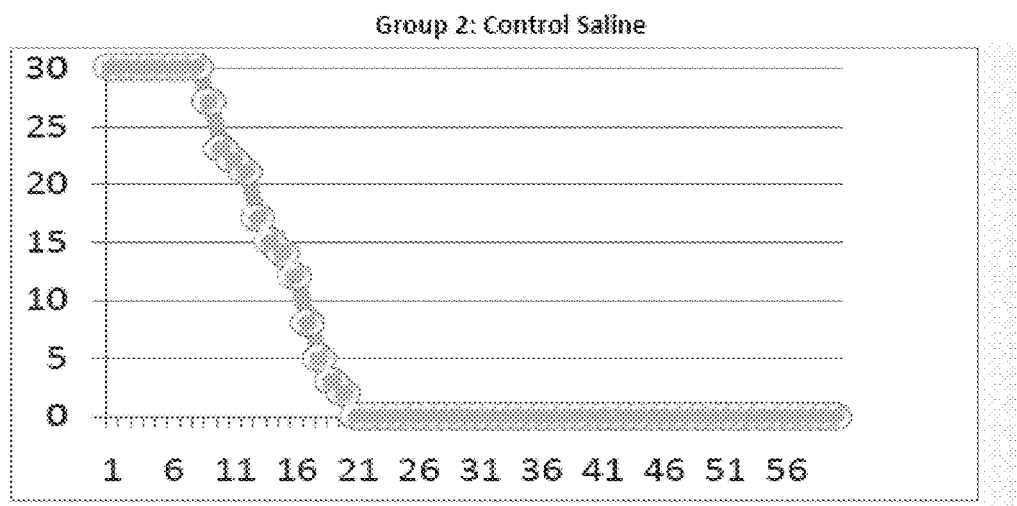

FIG. 38 depicts the results untreated NSG mice in a MiaPACA2 study.

Figure 39:
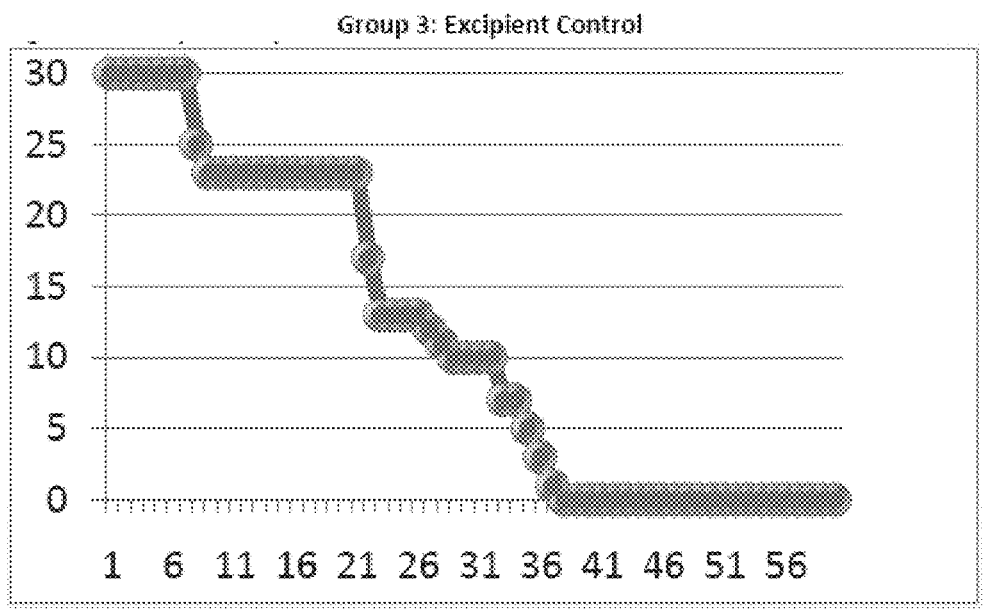

FIG. 39 depicts the results of NSG mice treated with excipient control in a MiaPACA2 study.

Figure 40:
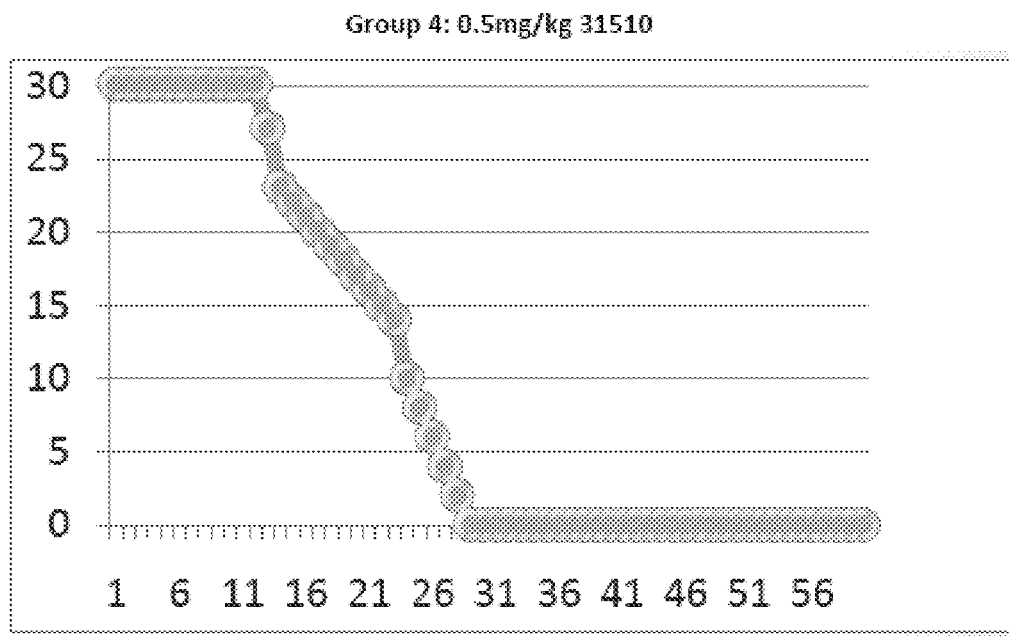

FIG. 40 depicts the results of NSG mice treated in a MiaPACA2 study with 0.5 mg/kg of the 4:3:1.5 CoQ10 IV formulation via intravenous infusion administration over about 4 hours.

Figure 41:
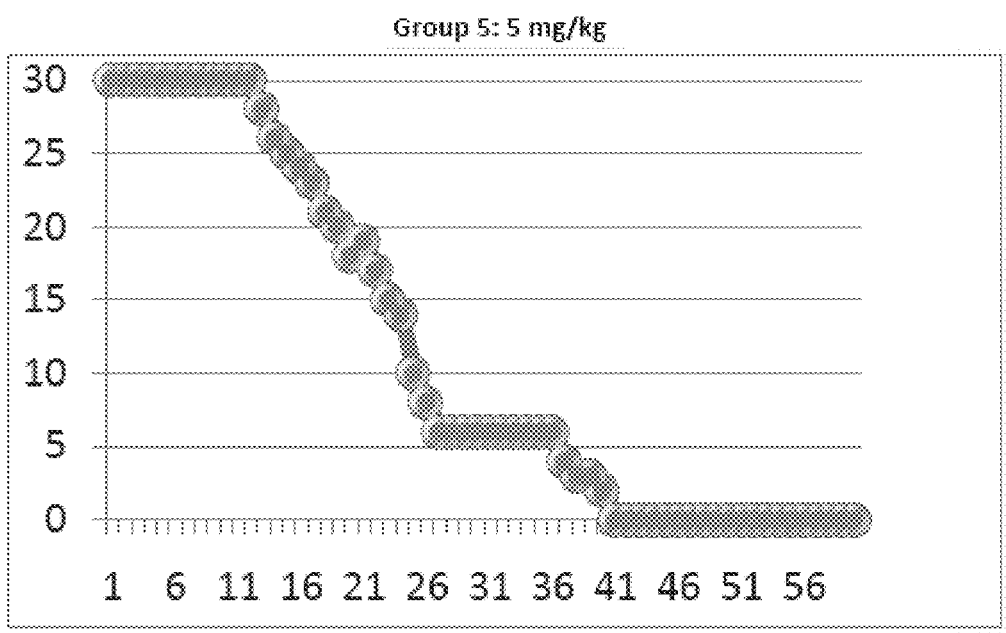

FIG. 41 depicts the results of NSG mice treated in a MiaPACA2 study with 5 mg/kg of the 4:3:1.5 CoQ10 IV formulation via intravenous infusion administration over about 4 hours.

Figure 42:
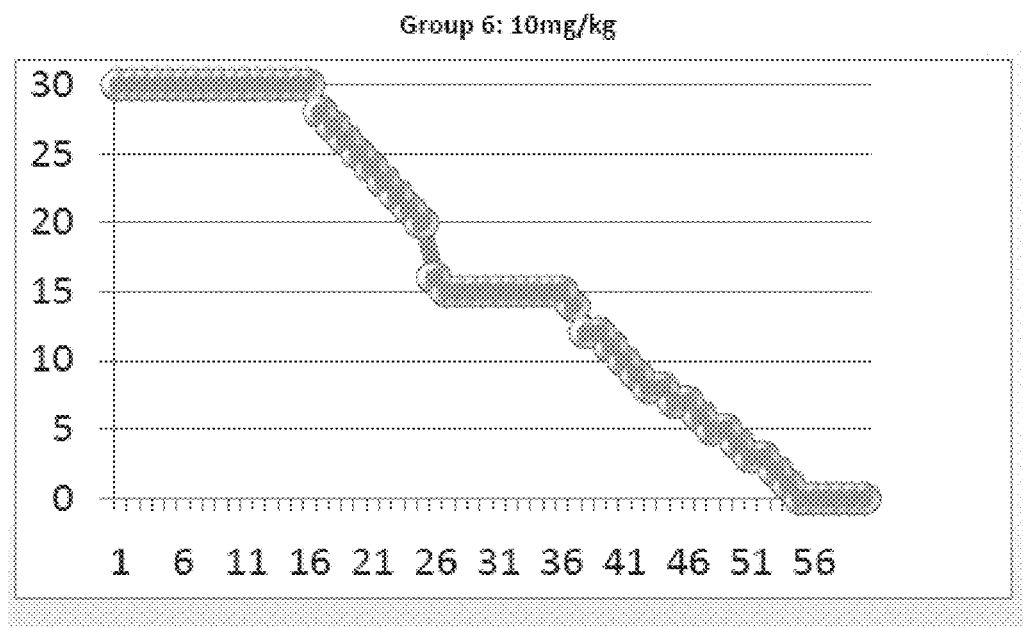

FIG. 42 depicts the results of NSG mice treated in a MiaPACA2 study with 10 mg/kg of the 4:3:1.5 CoQ10 IV formulation via intravenous infusion administration over about 4 hours.

Figure 43:
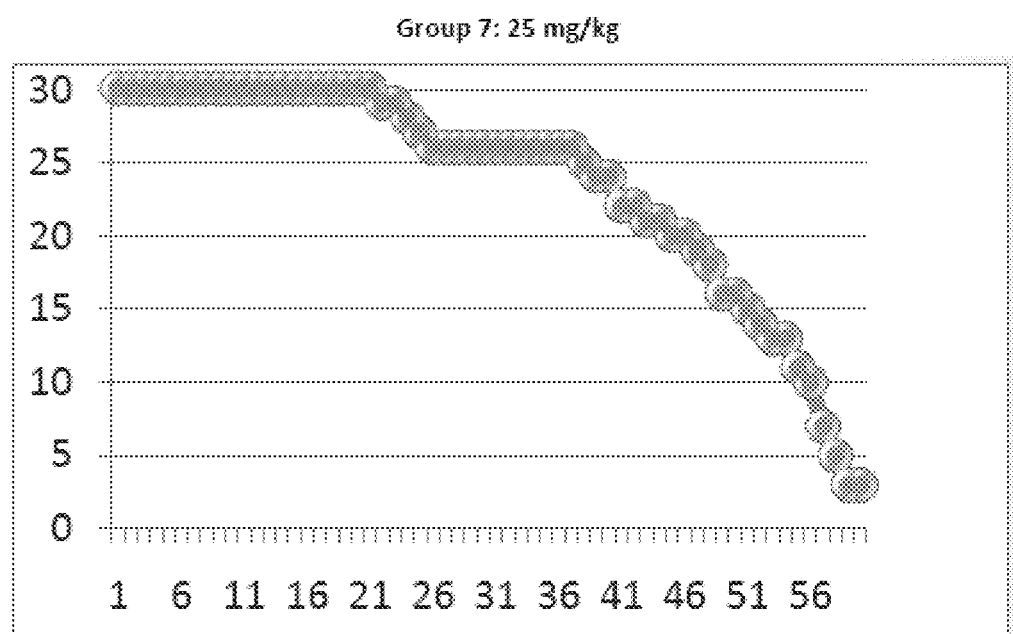

FIG. 43 depicts the results of NSG mice treated in a MiaPACA2 study with 25 mg/kg of the 4:3:1.5 CoQ10 IV formulation via intravenous infusion administration over about 4 hours.

Figure 44:
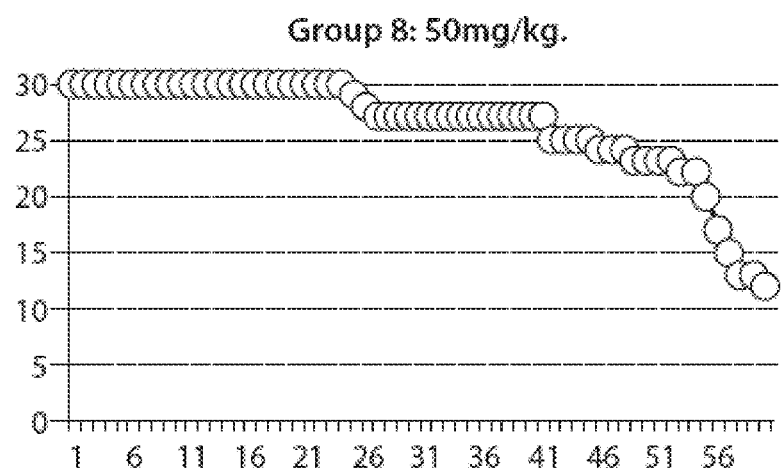

FIG. 44 depicts the results of NSG mice treated in a MiaPACA2 study with 50 mg/kg of the 4:3:1.5 CoQ10 IV formulation via intravenous infusion administration over about 4 hours.

Figure 45:
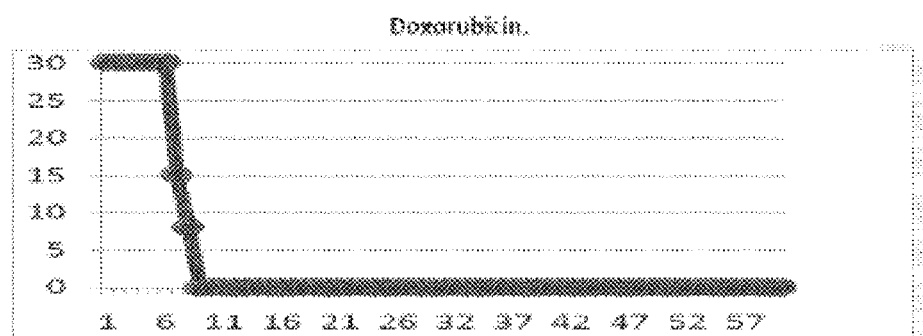

FIG. 45 depicts the survival results of mice treated with solo therapy doxorubicin.

Figure 46:
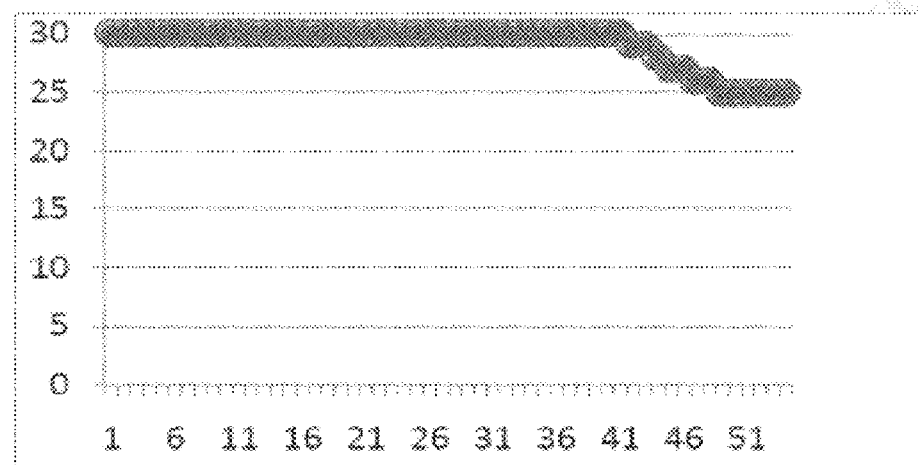

FIG. 46 depicts the survival results of mice treated with the combination therapy of doxorubicin and 4:3:1.5 CoQ10 IV formulation.

Figure 47:
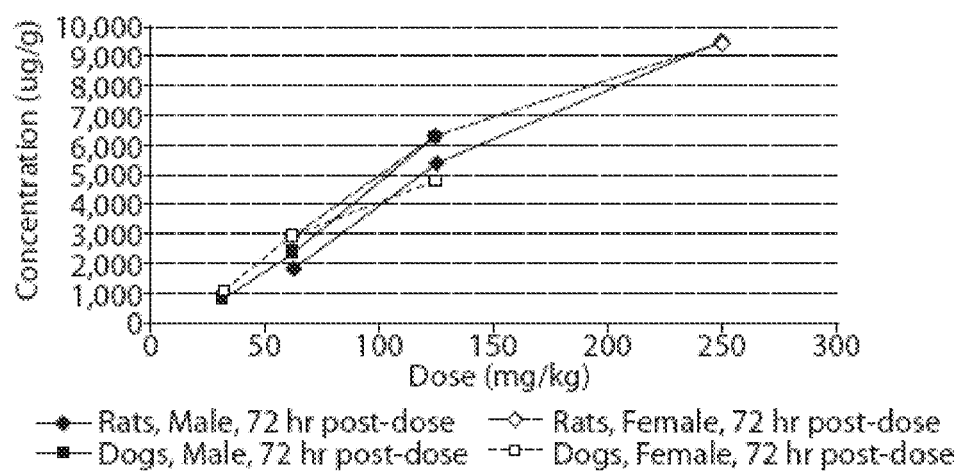

FIG. 47 depicts the mean liver concentrations of CoQ10 versus dose for male and female rats and dogs.

DETAILED DESCRIPTION

The present invention relates to intravenous formulations of poorly water-soluble active pharmaceutical agents, such as CoQ10.

The intravenous formulations of the present invention allow the delivery of precise amounts of an active pharmaceutical agent, such as CoQ10, into the blood stream for transport to organs such as the liver and heart and other tissues including tumors. The present invention provides a clinically and therapeutically effective and usable intravenous formulation of, e.g., CoQ10, that is stable at common ambient temperatures and remain essentially unchanged in dispersion characteristics for periods of at least 12 months.

For purposes of optimizing readability and to facilitate understanding of the invention as described herein, it may be beneficial to consider the following definition of terms and phrases as used herein.

I. DEFINITIONS

In accordance with the present disclosure and as used herein, the following terms are defined with the following meanings, unless explicitly stated otherwise.

As used herein, "a", "an," and "the" include plural references unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure. By "therapeutically effective amount" is meant an amount of a compound of the present disclosure effective to yield the desired therapeutic response. For example, accelerated wound healing, relief of pain and fatigue. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which approaches a normalized value (for example a value obtained in a healthy patient or individual), e.g., is less than 50% different from a normalized value, in embodiments less than about 25% different from a normalized value, in other embodiments is less than 10% different from a normalized value, and in yet other embodiments the presence of a symptom is not significantly different from a normalized value as determined using routine statistical tests.

As used herein, "an ameliorated symptom" or "treated symptom" refers to a symptom which approaches a normalized value, e.g., is less than 50% different from a normalized value, in embodiments less than about 25% different from a normalized value, in other embodiments less than about 10% different from a normalized value, and yet other embodiments the presence of a symptom is not significantly different from a normalized value as determined using routine statistical tests.

As used herein, "opsonization" refers to the process by which a lipophilic bioactive agent as described herein is marked for ingestion and destruction by a phagocyte. Opsonization involves the binding of an opsonin to bioactive agent. After opsonin binds to the membrane, phagocytes are attracted to the active agent. An opsonin is any molecule that acts as a binding enhancer for the process of phagocytosis.

As used herein, the term "opsonization reducer" refers to any agent that works in conjunction with the active agent to reduce the ability of opsonins to act as a binding enhancer for the process of phagocytosis.

In accordance with the present disclosure, a formulation is provided for improved administration of lipophilic bioactive agents, which may also be referred to herein as hydrophobic bioactive agents. As used herein, a "lipophilic bioactive agent" or "hydrophobic bioactive agent" includes an agent that is insoluble or is substantially insoluble in water. Specifically, lipophilic bioactive agents, as used herein, will have a solubility in water that is less than about 1 part of bioactive drug in about 1000 parts of water.

As used herein, the term "colloidal" refers to a state of subdivision, implying that the molecules or polymolecular particles dispersed in a medium have at least in one direction a dimension roughly between 1-nm and 1-μm.

As used herein, a "dispersion" or "colloidal dispersion" refers to a system in which particles of colloidal size of any nature (e.g., solid, liquid or gas) are dispersed in a continuous phase of a different composition or state. In intravenous drug delivery the continuous phase is substantially water and the dispersed particles can be solid (a suspension) or an immiscible liquid (emulsion).

As used herein, a "super-cooled melt" refers to the state of the active agent after homogenization wherein at a temperature below the melting point of the bulk material of the active agent, the colloidal particles are not in a solid or crystalline form but rather in an amorphous state.

As used herein, a "lyoprotectant" refers to pharmaceutically acceptable excipients, which protect the dispersed active agent against destabilizing conditions during the lyophilisation process, subsequent storage and reconstitution.

The terms "colloidal particles," "dispersion particles," "nano-dispersion particles," and "colloidal dispersion particles" are all used interchangeably herein and refer to the dispersed form of the active agent into nano-particles either in the bulk state or in a melted state.

The term "formulation" as used herein to refer to CoQ10 includes poloxamer unless otherwise specified.

A "patient" or "subject" to be treated by the method of the invention can mean either a human or non-human animal, preferably a mammal. It should be noted that clinical observations described herein were made with human subjects and, in at least some embodiments, the subjects are human.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein.

II. COMPOSITIONS

The present disclosure provides CoQ10 compositions for the treatment and prevention of cancer. The composition of the present disclosure can be administered to a patient either by themselves, or in pharmaceutical compositions where it is mixed with suitable carriers or excipient(s). In treating a patient exhibiting a disorder of interest, a therapeutically effective amount of an agent or agents such as these is administered. A therapeutically effective dose refers to that amount of the compound that results in amelioration of symptoms or a prolongation of survival in a patient.

Subjects from many different species can be treated with the compositions of the present disclosure. A non-exhaustive exemplary list of such animals includes mammals such as mice, rats, rabbits, goats, sheep, pigs, horses, cattle, dogs, cats, and primates such as monkeys, apes, and human beings. Those animal subjects known to suffer muscle fatigue, pain, wounds, and the like may be suitable for use of the present disclosure. In particular, human patients suffering from injuries, surgery, arthritis, muscle fatigue, cancer and the like are suitable animal subjects for use of the invention disclosed herein. By adapting the methods taught herein to other methods known in medicine or veterinary science (e.g., adjusting doses of administered substances according to the weight of the subject animal), the compositions utilized in the present disclosure can be readily optimized for use in other animals.

Suitable routes of administration of the present compositions of the invention may include parenteral delivery, including, intravenous intramuscular, subcutaneous, intramedullary injections, as well as intrathecal, direct intraventricular, intravenous, intraperitoneal, intranasal, or intraocular injections, just to name a few. In one embodiment, the compositions provided herein may be administered by injecting directly to a tumor. In some embodiments, the formulations of the invention may be administered by intravenous injection or intravenous infusion. In one embodiment, the compositions of the invention are administered by intravenous injection. In one embodiment, the compositions of the invention are administered by intravenous infusion. Where the route of administration is, for example intravenous infusion, embodiments are provided herein where the IV infusion comprises the active agent, e.g., Coenzyme Q10, at approximately a 40 mg/mL concentration. Where the composition is administered by IV infusion, it is diluted in phosphate buffered saline. In some embodiments, one or more routes of administration may be combined, such as, for example, intravenous and intratumoral, or intravenous and peroral, or intravenous and oral, or intravenous and transdermal or transmucosal.

The compositions described herein may be administered to a subject in any suitable formulation. For example, CoQ10 might be formulated for parenteral delivery, e.g., for subcutaneous, intravenous, intramuscular, or intratumoral injection. The compositions may be administered in a single bolus, multiple injections, or by continuous infusion (for example, intravenously or by peritoneal dialysis). For parenteral administration, the compositions may be formulated in a sterilized pyrogen-free form. Compositions of the present disclosure can also be administered in vitro to a cell (for example, to Bcl-2 production in a cell or in an in vitro culture) by simply adding the composition to the fluid in which the cell is contained.

Use of pharmaceutically acceptable carriers to formulate the compounds herein disclosed, for the practice of the present invention, into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices may be desirable. The data obtained from these cell culture assays and animal studies can be used in formulating a range of dosage for use in human. The dosage of such compounds may be within a range of circulating concentrations that include the ED50 with little or no toxicity. The dosage may vary within this range depending upon the dosage form employed and the route of administration utilized.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for intravenous administration may be in the form of solutions of colloidal dispersion.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

III. FORMULATIONS

The present invention provides therapeutic formulations comprising a hydrophobic active agent, such as Coenzyme Q10 (CoQ10), that are suitable for intravenous administration to a subject as described herein. Through high pressure homogenization, active agent (e.g., CoQ10) particles are reduced to produce particles that are small enough to pass through a 200-nm sterilizing filter. Particles that are small enough to pass through a 200-nm sterilizing filter can be injected intravenously. These particles are much smaller than blood cells and therefore will not embolize capillaries. Red blood cells for example are 6-mm×2-mm disks. The particles are dispersed to and are encased or surrounded by a stabilizing agent. While not wishing to be bound by any theory, it is believed that the stabilizing agents are attracted to the hydrophobic active agent such that the dispersed particles of the hydrophobic active agent are surrounded by the stabilizing agent forming a suspension or an emulsion. The dispersed particles in the suspension or emulsion comprises a stabilizing agent surface and a core consisting of the hydrophobic active agent in a solid particulate form (suspension) or in an immiscible liquid form (emulsion). In certain aspects, the dispersed particles are entrenched in the lipophilic regions of a liposome.

The dispersed colloidal system provided herein provides certain performance advantages over the prior art. For example, the present invention permits a high drug load in the formulation without the use of co-solvents. Additionally, high and relatively reproducible plasma levels are achieved without the dependence on endogenous low-density lipoprotein carriers. More importantly, the present invention allows sustained high drug levels in solid tumors due to the passive accumulation of the colloidal particles of the hydrophobic active agent.

The present intravenous formulation substantially comprises a continuous phase of water and dispersed solids (suspension) or dispersed immiscible liquid (emulsion). Dispersed colloidal systems, in which the particles are composed largely of the active agent (drug) itself, can often deliver more drug per unit volume than continuous solubilizing systems, if the system can be made adequately stable. The present invention provides colloidal dispersions of poorly water-soluble active agents, such as CoQ10.

By utilizing mechanical devices, such as a Microfluidizer, the particle size is reduced by high pressure continuous homogenization, forming colloidal-sized droplets in a spray system, or by shearing the particles in a liquid flowing at high velocity in a restricted and tortuous passage. Significant energy is required to cleave the bulk particle itself. The smaller particles increases the interfacial area of the active agent. Surfactants are used to reduce the interfacial energy thereby stabilizing the dispersion. The particle size determines the total interfacial area and the interfacial energy that must be accommodated to achieve a stable system. As the particle size goes down, more energy is required to produce the particle and since the total surface area goes up, the surfactant must accommodate a greater interfacial energy.

Through high pressure homogenization as exemplified herein, the particle size of the active agent, e.g., CoQ10, was reduced to less than 200-nm. In some embodiments the particle size was reduced to between 10-nm and 200-nm or between 10-nm and 100-nm or more preferably between 30-nm and 80-nm. In some embodiments, the resulting colloidal active agent, e.g., CoQ10, particles are in an amorphous super-cooled state as defined herein.

Figure 13:
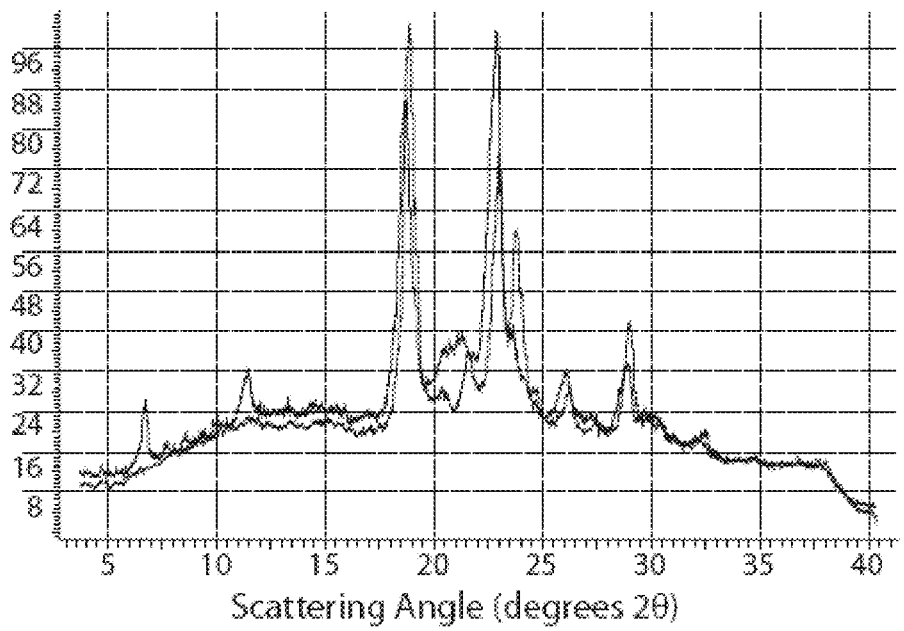
FIG. 13 depicts XRDP patterns for lyophilized sample Form V and superimposed with the pattern obtained from the CoQ10 bulk substance.

In certain embodiments, the dispersed CoQ10 particles are crystallized by a lyophilization process to produce nano-dispersion particles wherein the active agent core was in crystalline form (see FIGS. 1-3). Polarizing light microscopy (PLM) or X-ray powder diffraction (XRDP) was used to confirm the crystallinity of the CoQ10 colloidal dispersion and compared to the XRDP of bulk CoQ10 (see FIGS. 4-13). In form R, as depicted in FIG. 1, a formulation comprising 5.0 wt % CoQ10, 3.3 wt % poloxamer and 91 wt % of water, was cycled 20 times in a microfluidizer and then lyophilized to produce the particles depicted in the first vial from the left in FIG. 1. The XRDP, as depicted in FIG. 9 demonstrates that the CoQ10 particles were crystalline. In form A, as depicted in the FIG. 1 vial, second from the left, a formulation comprising 3 wt % CoQ10, 1.8 wt % Lipoid SPC-3 and 95.2 wt % water, was cycled 20 times in a microfluidizer to reduce the particle size. The particles were then lyophilized to produce the particles depicted in the second from left vial of FIG. 1. The XRDP, as depicted in FIG. 4 below, demonstrates that the CoQ10 particles were crystalline. In form 0, as depicted in FIG. 1, a formulation comprising 5.0 wt % CoQ10, 3.0 wt % DMPC and 92 wt % of water, was cycled 20 times in a microfluidizer and then lyophilized to produce the particles depicted in the third vial from the left in FIG. 1. The XRDP, as depicted in FIG. 7 below, demonstrates that the CoQ10 particles were crystalline. In form C, as depicted in FIG. 1, a formulation comprising 5.0 wt % CoQ10, 3.3 wt % poloxamer and 91 wt % of water, was cycled 20 times in a microfluidizer and then lyophilized to produce the particles depicted in the fourth vial from the left in FIG. 1. The XRDP, as depicted in FIG. 5 demonstrates that the CoQ10 particles were crystalline. In form G, as depicted in FIG. 2, a formulation comprising 5.0 wt % CoQ10, 3.0 wt % Lipoid SPC-3 and 92 wt % of water, was cycled 20 times in a microfluidizer and then lyophilized to produce the particles depicted in the first vial from the left in FIG. 2. The XRDP, as depicted in FIG. 6 demonstrates that the CoQ10 particles were crystalline. In form Q, as depicted in FIG. 2, a formulation comprising 5.0 wt % CoQ10, 2.5 wt % DMPC, 0.5 wt % sodium deoxycholate and 92 wt % of water, was cycled 20 times in a microfluidizer and then lyophilized to produce the particles depicted in the second vial from the left in FIG. 2. The XRDP, as depicted in FIG. 8 demonstrates that the CoQ10 particles were crystalline. In form S, as depicted in FIG. 2, a formulation comprising 7.5 wt % CoQ10, 4.5 wt % DMPC and 88 wt % of water, was cycled 20 times in a microfluidizer and then lyophilized to produce the particles depicted in the third vial from the left in FIG. 2. The XRDP, as depicted in FIG. 10 demonstrates that the CoQ10 particles were crystalline. In form T, as depicted in FIG. 2, a formulation comprising 7.5 wt % CoQ10, 5.0 wt % poloxamer and 87.5 wt % of water, was cycled 20 times in a microfluidizer and then lyophilized to produce the particles depicted in the fourth vial from the left in FIG. 2. The XRDP, as depicted in FIG. 11 demonstrates that the CoQ10 particles were crystalline. In form U, as depicted in FIG. 3, a formulation comprising 7.5 wt % CoQ10, 4.0 wt % DMPC, 1.0 wt % poloxamer 188 and 87.5 wt % of water, was cycled 20 times in a microfluidizer and then lyophilized to produce the particles depicted in the first vial from the left in FIG. 3. The XRDP, as depicted in FIG. 12 demonstrates that the CoQ10 particles were crystalline. In form V, as depicted in FIG. 3, a formulation comprising 3.0 wt % CoQ10, 1.5 wt % DMPC and 95.5 wt % of water, was cycled 20 times in a microfluidizer and then lyophilized to produce the particles depicted in the second vial from the left in FIG. 3. The XRDP, as depicted in FIG. 13 demonstrates that the CoQ10 particles were crystalline.

In lyophilizing the particles, the dryer was cooled to −35° C. Three milliliters of each of the above formulation was added to the 5 mL serum vial, in duplicate. Serum stopper was placed on top but allowed room for water vapor to escape. Formulations were placed in −78° C. freezer for 1-hour to rapid freeze. After this period, all were transferred in toto to the middle shelf of dryer. Vacuum was immediately initiated. After 16 hours the temperature was adjusted from −35° C. to −30° C. After 24 hours the temperature was adjusted from −30° C. to −28° C. After 2 hours, the temperature was adjusted from −28° C. to −26° C. After 4 hours the temperature was further adjusted to between −26° C. and −25° C. After reaching −25° C., the vials were stoppered and the vacuum released to ambient air. Vials were banded and photos taken of the dried products as depicted in FIGS. 1-3.

Figure 14:
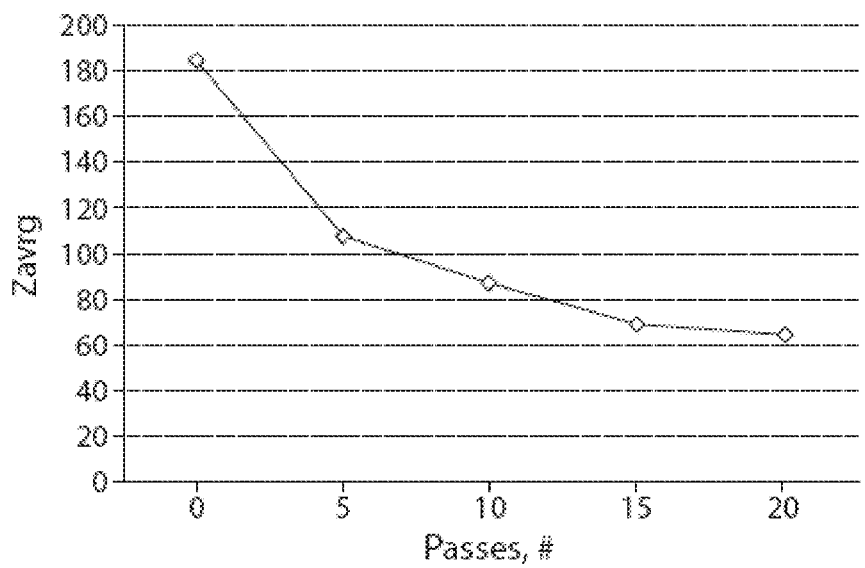
FIG. 14 depicts the effect of processing time on the colloidal nano-particles where the CoQ10 is 2.5 g, the DMPC is 1.5 g are homogenized in 46 mL of water.

In reducing the dispersion particle size, it may be desirable for the CoQ10 mixture to go through several passes through a Microfluidizer to obtain the desired particle size. After a single pass through M110P Microfluidizer with F12Y interaction chamber with 75-µm passages, particles of less than 200-nm mean diameter were produced. After 20 passes the mean diameter of the particles were less than 50-nm (see FIG. 14). The formulation contained 5 g of CoQ10, 3 g of DMPC and 92 mL of water. One of ordinary skill in the art will understand that the amounts of the CoQ10, DMPC and water may be adjusted depending on the desired therapeutic use. The Microfluidizer operated at a maximum pressure of 25,000 PSI. In certain embodiments, it is preferable to add at least one of a dispersion stabilizing agent and an opsonization reducer. In certain embodiments, the colloidal particles are prepared using both the dispersion stabilizer agent and the opsonization reducer. Preferred dispersion stabilizing agents include Polyethoxylated (a/k/a pegylated) castor oil (Cremophor® EL), Polyethoxylated hydrogenated castor oil (Cremophor® RH 40), Tocopherol polyethylene glycol succinate (Pegylated vitamin E, Vitamin E TPGS), Polysorbates (Tweens®), Sorbitan fatty acid esters (Spans®), Bile acids and bile-acid salts and DMPC while preferred opsonization reducers include Polyethylene glycol of various chain lengths, polysaccharides, other PEG-containing copolymers, poloxamines or poloxamers such as poloxamer 188. In certain embodiments, heparin also constitutes a suitable opsonization reducer. The poloxamer provides a hydrophilic surface so as to reduce particle opsonization after administration. The poloxamer also functions as a particle surface modifier, to add bulky chains to reduce opsonization by steric interaction. Poloxamer 188 (Pluronic® F68, Lutrol® F68) has approximately 28 PPG units in the center block and 79 PEG units in the end blocks. The hydrophobic center block anchors the molecule to the particle, and the PEG end blocks are extended from the particle. Opsonization is reduced by both the hydrophilicity of the PEG chains and by the steric (space-filling) effects of the chains (i.e., proteins can't get to the surface).

Through the methods, further described herein, the present invention provides a therapeutic formulation that is suitable for intravenous administration to a subject. The therapeutic formulation includes an aqueous solution. In certain embodiments of the present invention, the aqueous solution is water. The aqueous solution may function as either or both the dispersion medium for the colloidal system or as the formulation medium for parenteral administration and delivery of the colloidal particles. As the dispersion medium, the aqueous solution may contain other water soluble or dispersible stabilizers, isotonicity agents such as glycerol or xylitol, lyoprotectants such as sucrose, glucose, trehalose, etc., electrolytes, buffers, antilloculants such as sodium citrate, sodium pyrophosphate or sodium dodecylsulfate or preservatives.

Lyoprotectants comprise but are not limited to the group consisting of sugars, polyols (such as e.g. sugar alcohols) and amino acids. Preferred lyoprotectants include sugars such as sucrose, trehalose, and glucose. Other suitable sugars include, lactose, mannose, maltose, galactose, fructose, sorbose, raffinose, neuraminic acid, amino sugars such as glucosamine, galactosamine, N-methylglucosamine ("Meglumine"), polyols such as mannitol and sorbitol, and amino acids such as arginine and glycine.

As the formulation medium, the aqueous solution may include Hank's solution, ringer's solution, phosphate buffered saline (PBS), physiological saline buffer or other suitable salts or combinations to achieve the appropriate pH and osmolarity for parenterally delivered formulations. The aqueous solution may contain substances which increase the viscosity of the solution, such as sodium carboxymethyl cellulose, sorbitol, or dextran.

The therapeutic formulations of the invention include a hydrophobic, or otherwise poorly water-soluble, active agent. The hydrophobic active agent is dispersed in the aqueous solution such that a colloidal dispersion is formed wherein the nano-dispersion particles of the hydrophobic active agent are covered or encased or encircled by the dispersion stabilizing agents to form nano-dispersions of the active agent (e.g., CoQ10) particles. The nano-dispersed active agent (e.g., CoQ10) particles have a core formed of the hydrophobic active agent that is surrounded by the stabilizing agent. Similarly, in certain aspects, the stabilizing agent is a phospholipid having both a hydrophilic and lipophilic portion. The phospholipids form liposomes or other nanoparticles upon homogenization. In certain aspects these liposomes are bi-layered unilamellar liposomes while in other aspects the liposomes are bi-layered multi-lamellar liposomes. The dispersed active agent (e.g., CoQ10) particles are dispersed in the lipophilic portion of the bi-layered structure of the liposome formed from the phospholipids. In certain other aspects the core of the liposome, like the core of the nano-dispersion of active agent (e.g., CoQ10) particles is formed of the hydrophobic active agent and the outer layer is formed of the bi-layered structure of the phospholipid. In certain embodiments the colloidal dispersions are treated by a lyophilization process whereby the nanoparticle dispersion is converted to a dry powder.

In certain embodiments of the present invention, the hydrophobic agent is Coenzyme Q10 (CoQ10). Coenzyme Q10, also referred to herein as CoQ10, is also known as ubiquinone, or ubidecarenone. CoQ10 is art-recognized and further described in International Publication No. WO 2005/069916, the entire disclosure of which is incorporated by reference herein. CoQ10 is one of a series of polyprenyl 2,3-dimethoxy-5-methylbenzoquinone (ubiquinone) present in the mitochondrial electron transport systems of eukaryotic cells. Human cells produce CoQ10 exclusively and it is found in cell and mitochondrial membranes of all human cells, with the highest levels in organs with high energy requirements, such as the liver and the heart. The body pool of CoQ10 has been estimated to be about 2 grams, of which more than 50% is endogenous. Approximately 0.5 grams of CoQ10 is required from the diet or biosynthesis each day. CoQ10 is produced in ton quantities from the worldwide supplement market and can be obtained from Kaneka, with plants in Pasadena, Tex. and Takasagoshi, Japan.

The tissue distribution and redox state of CoQ10 in humans has been characterized. Typically, tissues with high-energy requirements or metabolic activity such as the heart, kidney, liver and muscle have relatively high concentrations of CoQ10. Most of the CoQ10 in plasma is present as the reduced ubiquinol. A substantial portion of CoQ10 in tissues is in the reduced form as the hydroquinone or uniquinol. The exception is brain and lung. The oxidized state is presumed to be a reflection of the increased oxidative stress in the tissues. More specifically, in heart, kidney, liver, muscle, intestine and blood (plasma), about 61%, 75%, 95%, 65%, 95% and 96%, respectively, of CoQ10 is in the reduced form.

CoQ10 is very lipophilic and, for the most part, insoluble in water. Due to its insolubility in water, limited solubility in lipids, and relatively large molecular weight, the efficiency of absorption of orally administered CoQ10 is poor. Bhagavan, et al. (*Free Rad. Res.* 40:445-453 (2006)) reported that that in rats only about 2-3% of orally-administered CoQ10 was absorbed and that CoQ10 is reduced to ubiquinol either during or following absorption in the intestine. In a study by Matthews et al., (*Proc. Natl. Acad. Sci. USA* 95:8892-8897 (1998)), CoQ10 uptake was found to be age dependent in some tissues. For example, in young rats, plasma, liver, and spleen concentrations increased after four days of dosing, but no increase was observed in heart or kidney. Similarly, oral administration did not increase concentration of CoQ10 in brain in 1-2 month old animals. However, administration of CoQ10 to 12 month old and 24 month old rats resulted in accumulation of CoQ10 in cerebral tissues in both the oxidized and reduced forms. Interestingly, CoQ10 production is stimulated in young rats, but not old rats, after ischemic-reperfusion injury.

In one embodiment of the invention, the hydrophobic active agent is CoQ10, a metabolite of CoQ10, a building block of CoQ10, an analog of CoQ10, or a derivative of CoQ10. An analog of CoQ10 includes analogs having no or at least one isoprenyl repeats. CoQ10 has the following structure:

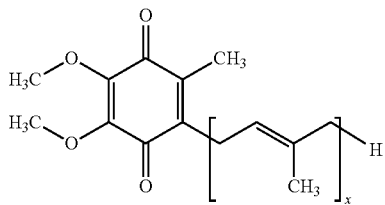

wherein x is 10. In the instant invention, CoQ10 can include derivatives of CoQ10 in which x is any number of isoprenyl units from 4-10, or any number of isoprenyl units from 6-10, or any number of isoprenyl units from 8-10, or 9-10 isoprenyl units. CoQ10 includes the fully oxidized version, also known as ubiquinone, the partially oxidized version, also known as semiquinone or ubisemiquinone, or the fully reduced version, also known as ubiquinol; or any mixtures or combinations thereof.

Building blocks of CoQ10 include any components or synthetic precursors, preferably biologically relevant precursors, of CoQ10. Thus, building blocks of CoQ10 include, but are not limited to, phenylalanine, tyrosine, 4-hydroxyphenylpyruvate, phenylacetate, 3-methoxy-4-hydroxymandelate, vanillic acid, 4-hydroxybenzoate, mevalonic acid, farnesyl, 2,3-dimethoxy-5-methyl-p-benzoquinone, as well as the corresponding acids or ions thereof. Experimental data indicate that building blocks of CoQ10 biosynthesis, such as the precursors for the biosynthesis of the benzoquinone ring, and those for the biosynthesis of the isoprenoid repeats and their attachment to the benzoquinone ring, can be individually administered or administered in combination to target cells to modulate expression of the apoptosis inhibitor Bcl-2 and/or expression of the apoptosis promoter Caspase-3. See, e.g., U.S. patent application Ser. No. 12/778,094 and the examples provided herein.

A metabolite of CoQ10 includes any known metabolite of CoQ10. See e.g., Turunen, M. et al. *Biochemica et Biophysica Acta* 1660: 171-199 (2004), the entire contents of which are incorporated by reference herein. The main metabolite has been identified has an aromatic ring with a side chain shortened to 5-7 atoms. Such a metabolite is shown below. The metabolite may optionally be phosphorylated at carbon 4 or carbon 1.

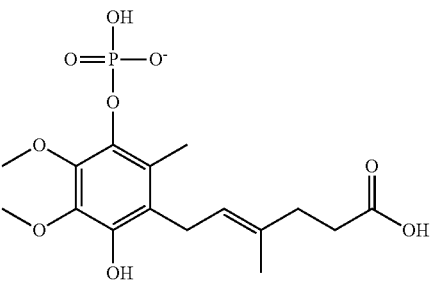 [SMILES: COc1c(O)c(C/C=C(\C)CCC(=O)O)c(C)c(OP(=O)([O-])O)c1OC]

A derivative of CoQ10 includes any compound that is structurally identical to CoQ10, except that one atom is replaced with another atom or group of atoms.

Other hydrophobic active agents that are suitable for incorporation into this colloidal system include anesthetics such as butanilicain, fomocain, lidocain, prilocaln, tetracain and etomidate; antibiotics such as fosfomycin, fosmidomycin and rifapentin; antihypertensives such as minoxidil, dihydroergotoxine and endralazine; antihypotensives such as dihydroergotamine; systemic antimycotics such as ketoconazole, miconazole and griseofulvin; antiphiogistics such as indomethacin, diclofenac, ibuprofen, ketoprofen and pirprofen; antiviral agents such as aciclovir, vidarabin and immunoglobulines; ACE inhibitors such as captopril and enalapril; betablockers such as propranolol, atenolol, metoprolol, pindolol, oxprenolol and labetalol; bronchodilators such as ipratropiumbromide and sobrerol; calcium antagonists such as diltiazem, flunarizin, verapamil, nifedipin, nimodipin and nitrendipin; cardiac glycosides such as digitoxin, digoxin, methyldigoxin and acetyldigoxin; cephalosporins such as ceftizoxim, cefalexin, cefalotin and cefotaxim; cytostatics such as chlormethin, cyclophosphamid, chlorambucil, cytarabin, vincristin, mitomycin C, doxorubicin, bleomycin, cisplatin, taxol, penclomedine and estramustin; hypnotics such as flurazepam, nitrazepam and lorazepam; psychotropic drugs such as oxazepam, diazepam and bromazepam; steroid hormones such as cortisone, hydrocortisone, prednisone, prednisolone, dexamethasone, progesterone, pregnanolone, testosterone and testosterone undecanoate; vasodilators such as molsidomin, hydralazin and dihydralazin; cerebral vasodilators such as dihydroergotoxin, ciclonicat and vincamin; ubiquinones and their analogues such as ubidecarenone and atovaquon; lipophilic vitamins such as vitamin A, E, D, K and their derivates; insecticides, herbicides and pesticides such as acephate, cyfluthrin, azinphosphomethyl, cypermethrin, fenclofos, permelthrin, piperonal, tetramethrin and trifluralin. In certain other embodiments, the colloidal system includes mTor inhibitors, EGFr, and FGF analogues.

The active agent can be located in the core of the colloidal particles where they are dissolved, solubilized or dispersed in the matrix, and/or in the stabilizer layer(s) surrounding the particle core, and/or can be adsorbed to the surface of the colloidal particles. The bioactive substances can be dissolved or crystalline or amorphous or a mixture of any of these states. The therapeutic formulation also includes at least one of a dispersion stabilizing agent and an opsonization reducer. The colloidal particles may be liposomes as described herein and may also contain other active agents or other inactive agents, or other hydrophobic or hydrophilic agents.

Figure 15:
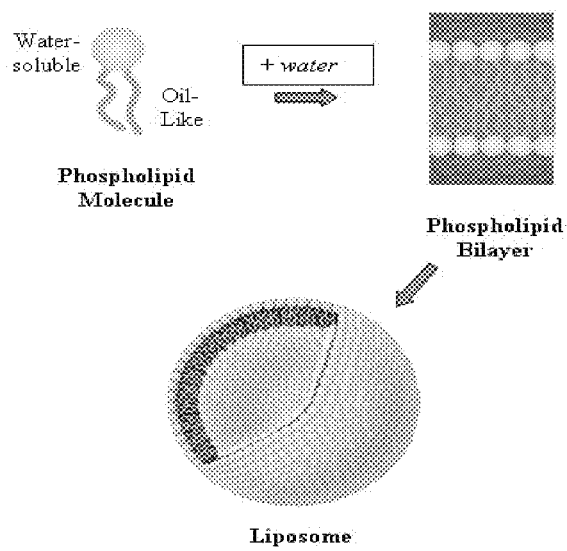
FIG. 15 depicts a liposome formed by the methods disclosed herein where the liposome is bi-layered unilamellar liposome.
Figure 16:
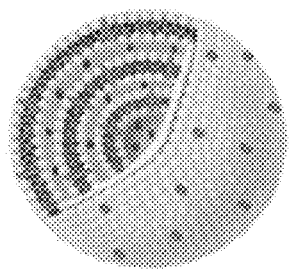
FIG. 16 depicts a liposome formed by the methods disclosed herein where the liposome is a bi-layered multi-lamellar liposome.

Dispersion of the active agent, e.g., CoQ10, bulk material into nano-particles increases the interfacial energy as the size of the particles is reduced over passes through the homogenization process. The affinity of a dispersion stabilizing agent such as, for example, DMPC, to the active agent, e.g., CoQ10, nano-particles, causes the dispersion stabilizing agent (e.g., DMPC) to encase the nano-particles and form an active agent, e.g., CoQ10, nano-dispersion. The dispersion stabilizing agent stabilizes the active agent, e.g., CoQ10, nano-dispersion by accommodating the high interfacial energy and thereby preventing or reducing coalescence of the dispersed active agent, e.g., CoQ10, particles. In certain embodiments of the invention, liposomes are formed by the colloidal dispersions wherein the phospholipid stabilizer forms a bi-layered system about the dispersed particles of the hydrophobic bioactive agent or substance. In certain embodiments the liposomes are bi-layered unilamellar liposomes as depicted in FIG. 15. In other embodiments the liposomes are bi-layered multilamellar liposomes as depicted in FIG. 15. In certain embodiments, the dispersed particles of the hydrophobic active agent are within lipophilic portion of the bi-layers. In certain other embodiments, where the liposome are multi-lamellar, the hydrophobic active agent is within the lipophilic portion of the bi-layers. In certain other embodiments where the liposomes are multi-lamellar, the dispersed hydrophobic active agent is within the lipophilic portion of the bi-layer of the liposome and a second agent is in the hydrophilic portion that is between the bi-layered portions of the multi-lamellar liposome.

Proper selection of a surfactant, or a mixture of surfactants, can produce a formulation in which the shelf product is a concentrated solution of drug in liquid surfactants, and upon addition of infusion fluid, the interfacial energy reduction achieved by the surfactants is sufficient to emulsify the system to a colloidal system. The dispersion stabilizing agent may be selected from Polyethoxylated (a/k/a pegylated) castor oil (Cremophor® EL), Polyethoxylated hydrogenated castor oil (Cremophor® RH 40), Tocopherol polyethylene glycol succinate (Pegylated vitamin E, Vitamin E TPGS), Polysorbates (Tweens®), Sorbitan fatty acid esters (Spans®), Bile acids and bile-acid salts and dimyristoylphosphatidyl choline (DMPC). The dispersion stabilizing agent organizes at the interface of the reduced size particles and reduce the interfacial energy, making the dispersion more stable.

Phospholipids have a high affinity for CoQ10, as is demonstrated by the close association of the two in biological membranes. The dispersion stabilizing agent is included in the formulation to, at least, reduce the interfacial tension as the particle size is reduced. In the colloidal dispersion, the nano-dispersion particles include an active agent core surrounded by the stabilizing agent. The dispersion stabilizing agent is typically an amphiphilic substance, i.e. those with a hydrophilic and hydrophobic part of the molecules. At the particle surface, the amphiphilic substances are predominantly arranged in such a way that the hydrophobic part of the molecule protrudes into the core and the hydrophilic part into the surrounding dispersion medium. The surfaces are therefore hydrophilic.

Other suitable phospholipids include lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof and therewith.

In one embodiment, the dispersion stabilizing agent is not an agent selected from the group of lecithin, polysorbate 80 and olacta. In one embodiment, the dispersion stabilizing agent is not lecithin. In one embodiment, the dispersion stabilizing agent is not polysorbate 80. In one embodiment, the dispersion stabilizing agent is not olacta.

The formulations of the invention may further include an opsonization reducer. The opsonization reducer may be selected from Polyethylene glycol of various chain lengths, polysaccharides, other PEG-containing copolymers, poloxamines or poloxamers such as poloxamer 188. As defined herein, an opsonization reducer refers to any inactive agent that works in conjunction with the active agent to reduce the ability of opsonins to act as a binding enhancer for the process of phagocytosis. The inactive agent must be included in the FDA's Inactive Ingredient List, which is hereby incorporated by reference in its entirety. The inactive agents must not include pegylated nonionic surfactants (e.g., polysorbate 80, polyethoxylated castor oil, and PEG ethers and esters of fatty alcohols and acids, respectively), since these materials can cause extreme hypersensitivity reactions. Accordingly, in one embodiment, the opsonization reducer is not polysorbate 80. In one embodiment, the opsonization reducer is not polyethoxylated castor oil. In one embodiment, the opsonization reducer is not PEG ethers of fatty alcohols. In one embodiment, the opsonization reducer is not PEG esters of fatty acids.

Colloidal-sized particles larger than 10-nm, for example, are not filtered by the kidneys and will circulate until they are cleared by active processes or they extravasate by diffusing through gaps between vascular endothelial cells. Phagocytic cells of the reticuloendothelial system (RES) or mononuclear phagocytic system (MPS) will capture colloidal particles by endocytosis. These cells include macrophages related to liver (Kupffer cells), spleen, lymph nodes (perivascular macrophages), nervous system (microglia), and bones (osteoclasts). Nonspecific attachment of opsonins (e.g., immunoglobulins, complement components, other serum proteins) marks the particles as foreign. Enzymes and an oxidative-reactive environment in the endosome will destroy the captured particles.

Opsonization of colloidal particles can be reduced, resulting in longer circulation, by a number of factors, including particle size below 100-nm, a neutral or negative surface charge, and adsorption or bonding of bulky hydrophilic chains. An important element of the utility of colloidal drug delivery to solid tumors results from unique anatomical and physiological characteristics of tumors. The capillary network of tumors is tortuous with wide interendothelial junctions (100 to 780-nm) and the tumor has no lymphatic drainage. These characteristics result in passive targeting of colloidal particles to tumors. Particles extravasate through the leaky junctions and remain in the tumor interstitium.

The opsonization reducer is included in the formulation to modify the biological response to the particles. The present invention provides a method wherein the ability to clear the colloidal drug particles by opsonization is reduced by the inclusion of an opsonization reducer in the formulation presented herein. The inclusion of an opsonization reducer results in higher drug levels in tumors than in the plasma.

In one embodiment, the formulation of the invention does not comprise polysorbate 80. In one embodiment, the formulation of the invention does not comprise polyethoxylated castor oil. In one embodiment, the formulation of the invention does not comprise PEG ethers of fatty alcohols. In one embodiment, the formulation of the invention does not comprise PEG esters of fatty acids. In one embodiment, the formulation of the invention does not comprise an agent selected from the group of lecithin, polysorbate 80 and olacta. In one embodiment, the formulation of the invention does not comprise lecithin. In one embodiment, the formulation of the invention does not comprise polysorbate 80. In one embodiment, the formulation of the invention does not comprise olacta.

It has been found, and herein disclosed, that the ratio of the active agent and the inactive agents are important to the control of the particles size. In order to obtain the benefits of the dispersion stabilizing agent and the opsonization reducer without negatively impacting the benefits of either, or that of the particle size, the ratio of active agent (e.g., CoQ10), dispersion stabilizing agent (e.g., DMPC) and opsonization reducer (e.g., poloxamer) may be adjusted to accommodate a desired particle size and a desired biological response to the colloidal dispersion upon intravenous administration. In certain embodiments, the formulation is prepared such that the weight-per-volume of active agent (e.g., CoQ10), dispersion stabilizing agent (e.g., DMPC) and opsonization reducer (e.g., poloxamer) are each 4%, 3%, and 1.5%, respectively. In certain other embodiments the weight-per-volume of active agent (e.g., CoQ10), dispersion stabilizing agent (e.g., DMPC) and opsonization reducer (e.g., poloxamer) are 8%, 6% and 3.0%, respectively. In certain embodiments, the formulation is prepared such that the weight-per-volume of CoQ10, DMPC and poloxamer are each 4%, 3%, and 1.5%, respectively. In certain other embodiments the weight-per-volume of CoQ10, DMPC and poloxamer are 8%, 6% and 3.0%, respectively.

The hydrophobic active agent is dispersed at a temperature above its melting point to facilitate dispersion. CoQ10 has a melting point of approximately 48° C. It is herein contemplated that the melting point may vary and may, for example include any value ranging from 47.5° C. to 49.5° C., e.g., 47.5° C., 48.0° C., 48.5° C., 49.0° C. or 49.5° C. In certain embodiments, CoQ10 is mixed in a water bath of 65° C. to form a CoQ10/water mixture, thereby improving the ability to disperse and reduce the particle size of CoQ10.

In preferred embodiments, the active agent, for example CoQ10, is processed through a high-pressure homogenizer (Microfluidizer), such as those available from Microfluidics, Inc. A process stream containing CoQ10 is pumped into an interaction chamber at high velocity and the particles are sheared by wall collisions and cavitations. These shear effects reduce the particle size over repeated passes through the Microfluidizer. The particles of the present invention have size distributions in the nanometer size range with mean particle diameters less than about 200-nm as determined by photon correlation spectroscopy. In one embodiment, the mean size of the nano-dispersion particle is less than about 150-nm. In one embodiment, the mean size of the nano-dispersion particle is less than about 125-nm. In one embodiment, the mean size of the nano-dispersion particle is less than about 100-nm. In one embodiment, the mean size of the nano-dispersion particle is less than about 95-nm, less than about 90-nm, less than about 85-nm, less than about 80-nm, less than about 75-nm, less than about 70-nm, less than about 65-nm, less than about 60-nm, less than about 55-nm, less than about 50-nm, less than about 45-nm, less than about 40-nm, less than about 35-nm, less than about 30-nm, or less than about 25-nm. In one embodiment, the mean size of the nano-dispersion particle is less than about 49-nm, less than about 48-nm, less than about 47-nm, less than about 46-nm, less than about 45-nm, less than about 44-nm, less than about 43-nm, less than about 42-nm, or less than about 41-nm. In one embodiment, the mean size of the nano-dispersion particle is less than about 45-nm. It should be understood that ranges having any one of these values as the upper or lower limits are also intended to be part of this invention, e.g. between about 40-nm and 49-nm, between about 25-nm and 48-nm, or between 25-nm and 47-nm.

In certain other embodiments, through several passes through the Microfluidizer, the mean particle size is reduced to between 10-nm and 200-nm. In one embodiment, the mean particle size is reduced to between 10-nm and 150-nm. In one embodiment, the mean particle size is reduced to between 10-nm and 125-nm. In other embodiments the mean particle size is reduced to between 10-nm and 100-nm. In certain other embodiments the mean particle size is reduced to between 10-nm and 90-nm, between 10-nm and 80-nm, between 10-nm and 70-nm, between 10-nm and 60-nm, between 10-nm and 50-nm, between 10-nm and 45-nm, between 10-nm and 40-nm, or between 10-nm and 30-nm. In certain preferred embodiments the mean particle size is reduced to between 20-nm and 80-nm. In one embodiment, the mean particle size is reduced to between 20-nm and 70-nm. In one embodiment, the mean particle size is reduced to between 20-nm and 60-nm. In one embodiment, the mean particle size is reduced to between 20-nm and 50-nm. In one embodiment, the mean particle size is reduced to between 25-nm and 45-nm. In one embodiment, the mean particle size is reduced to between 30-nm and 45-nm. In certain other preferred embodiments the mean particle size is reduced to between 35-nm and 40-nm. It should be understood that additional ranges having any one of the foregoing values as the upper or lower limits are also intended to be part of this invention, e.g., between 30-nm and 80-nm, or between 30-nm and 40-nm.

It may be preferable to have the colloidal dispersion in the form of a suspension or, alternatively, in the form of an emulsion. As defined elsewhere herein, a suspension, or nanosuspension, comprises a continuous phase and dispersed solids while an emulsion includes a dispersed immiscible liquid. In certain aspects the emulsion includes a dispersed hydrophobic agent that has been melted and dispersed in a continuous phase to form nano-particles. Where the hydrophobic active agent is CoQ10, the melted and dispersed particles may be further dispersed and the size of the particles reduced further by subsequent passes through the homogenization process. As with the solid particles, the smaller the particles of the melted hydrophobic active agent the higher the interfacial energy. A stabilizing agent, such as DMPC, is used to stabilize the dispersed particles by forming a surface layer around the dispersed particles thereby creating nano-dispersed CoQ10 particles. The particles formed are less than 200 nm. The suspension includes particles of the bulk hydrophobic active agent that are dispersed by high energy homogenization. In the suspension are nano-dispersions of the hydrophobic active agent, such as CoQ10. The nano-dispersion of CoQ10, for example, includes dispersed particles of the bulk CoQ10 that are surrounded by a stabilizing agent, such as DMPC. The stabilizing agent forms a surface layer around the dispersed bulk hydrophobic agent and the dispersed particle of the CoQ10 forms the core of the nano-dispersed particles. In some embodiments the nano-dispersed particles are in an amorphous state. In certain other embodiments, the particles are lyophilized and the CoQ10 core of the nano-dispersion particles of CoQ10 is crystallized.

The formulations described herein may be administered to a subject in an effective amount. An effective amount is an amount which is capable of producing a desirable result in a treated subject or cell. As is well known in the medical and veterinary arts, dosage of any one animal depends on may factors, including the particular animal's size, body type, age, the particular composition to be administered, time and route of administration, general health, and the effects of pre-, co- or post-administered drugs. It is expected that an appropriate dosage for parenteral administration of the formulation would be from about 10 to about 500 mg of CoQ10 for subjects ranging from about 110 to about 300-lbs. An effective amount for use with a cell culture will also vary, but can be readily determined empirically (i.e., by adding varying concentrations to the cell and selecting the concentration that best produces the desired result). It is expected that an appropriate concentration would be from about 1 to about 250-µM.

IV. METHODS OF PREPARING THE FORMULATION

CoQ10 is a solid and primarily crystalline substance at room temperature in the bulk phase (i.e., bulk material). The solid bulk material which is used as a starting material for preparing colloidal particles according to the present invention can be non-particulate, or particulate, e.g., a powder, precipitate, agglomerates, crystals or any other solid raw material commonly used.

In preparing the formulations of the present invention, poorly water soluble hydrophobic active agent, such as bulk phase CoQ10 or a mixture of poorly water-soluble substances, are heated in a bath above the melting point of the hydrophobic active agent. For example, the melting point of CoQ10 is approximately 48° C. It is herein contemplated that the melting point may vary and may, for example include any value ranging from 47.5° C. to 49.5° C. The bath, consisting of water is at 65° C. CoQ10 in bulk form at room temperature is added to the 65° C. water and mixed to form a CoQ10/water mixture. In certain embodiments, the CoQ10/water mixture is mixed for 45 minutes. In certain other embodiments it is mixed for 20-30 minutes. Powder DMPC is then added to the CoQ10/water mixture (M1) and mixed to form a CoQ10/water/stabilizer mixture. In certain embodiments the CoQ10/water/stabilizer mixture (M2) is mixed for between 25 and 45 minutes at 65° C. In certain other embodiments, the CoQ10/water/stabilizer mixture is mixed for 30 minutes at 65° C. An opsonization reducer is then added to form a CoQ10/water/stabilizer/reducer mixture. The Microfluidizer chamber is pre-heated to 60-65° C. The CoQ10/water/stabilizer/reducer (M3) is then processed in the Microfluidizer in repeated passes to reduce the particle size below 200-nm.

Suitable Microfluidizers include the M110P and is available through Microfluidics, Inc. (MFI). The M110P has a 75-µm passages and a F12Y interaction chamber. In processing M3, the Microfluidizer has an inlet pressure of 30,000 psi.

After 20 passes in the Microfluidizer, the particle size was reduced to between 30-nm and 80-nm or preferably between 30-nm and 75-nm.

Colloidal dispersions of CoQ10 were prepared by emulsification of the molten CoQ10 stock material in water employing various types and amounts of stabilizing agents and opsonization reducers. Emulsification was accomplished by probe sonication and/or high pressure homogenization. Preferably, the emulsification is accomplished by high pressure homogenization. High pressure homogenization systems display a smaller mean particle size and a more narrow particle size distribution. The mean particle diameter of the colloidal dispersions of CoQ10 can be varied within a considerable range by varying the process parameters such as homogenization equipment, homogenization parameters (time, cycles, pressures, etc.) and the composition of the dispersions (type and amount of stabilizer and opsonization reducer, phase ratio, etc.). Siekmann and Westesen describes sub-micron sized formulations of CoQ10 made by emulsification wherein the colloidal particles are in an amorphous state (Siekmann, B., and K. Westesen. "Preparation and physicochemical characterization of aqueous dispersions of coenzyme Q10 nanoparticles." Pharmaceutical Research 12, no. 2 (1995): 201-208) which is incorporated herein by reference in its entirety.

The present invention provides colloidal dispersions of hydrophobic active agents, such as CoQ10, prepared by methods unlike those disclosed by Siekmann and Westesen. The present invention provides methods wherein the CoQ10 is emulsified to produce colloidal particles of CoQ10. While the particles in some embodiments are in an amorphous state, in other embodiments, the particles are lyophilized such that the colloidal CoQ10 particles are in a crystalline form. In certain embodiments of the present invention, a lyoprotectant is used to stabilize the particle size upon lyophilization. Further notable distinctions in the present invention include the inactive agents employed in the homogenization of the colloidal particles of the present invention. The presently disclosed methods include at least one of a stabilizing agent and an opsonization reducer as described further herein.

The present invention further includes novel ratios for the hydrophobic agent, the stabilizing agent and the opsonization reducer. The homogenization process for CoQ10 produces an amorphous CoQ10 colloidal dispersions which include poloxamer (as an opsonization reducer) and DMPC (as a dispersion stabilizing agent) in ratios that produce colloidal CoQ10 particles having sizes below 200-nm and preferably about 40-nm. Suitable DMPC can be purchased from Genzyme Corporation, Lipoid, Avanti, or NOF while suitable poloxamer 188 may be purchased from Spectrum Corporation or BASF Corporation.

In preparing the colloidal dispersion, the weight-per-volume of CoQ10, DMPC and poloxamer 188 were selected as 4%, 3% and 1.5%, respectively (i.e., the 4:3:1.5 ratio). In certain other suitable embodiments, the weight-per-volume of CoQ10, DMPC and poloxamer were 8%, 6% and 3%, respectively (i.e. the 8:6:3 ratio). In certain embodiments, the concentration of CoQ10 is between 30 mg/mL and 90 mg/mL. In certain other embodiments, the concentration of CoQ10 is about 40 mg/mL for the 4:3:1.5 ratio, about 80 mg/mL for the 8:6:3 ratio and about 60 mg/mL for the 6:3:1 ratio.

The colloidal dispersions of CoQ10 are stable at room temperature over several weeks. Over two to three weeks, the particles size remained unchanged as shown in Table 1 and Table 2. A comparison of the columns labeled "Filtered"

and "Repeat" indicates that up to two weeks storage of filtered suspension did not significantly affect the particle size. Table 1 further demonstrates that increase in DMPC/CoQ10 ratio and addition of poloxamer 188 results in decreased particle size. A CoQ10/DMPC/P188 4:3:0 formulation was stored in a stability chamber at 25° C. and 60% humidity. $Z_{avg}$ (particle size) was assessed over time.

TABLE 1

| | Particle Size (Z-avrg) | | | | | |
|---|---|---|---|---|---|---|
| | Processed | | Filtered | | Repeat | |
| Formula/SOP | Date | Nm | Date | Mm | Date | Nm |
| 4/1/0 (SOP4.4) | Sep. 8, 2009 | 77.2 | Sep. 8, 2009 | 74.3 | Sep. 17, 2009 | 74.2 |
| 4/2/0 (SOP4.2) | Sep. 1, 2009 | 61.7 | Sep. 2, 2009 | | | |
| | | | Sep. 3, 2009 | 63.5 | Sep. 17, 2009 | 62.2 |
| 4/3/0 (SOP1.1) | Aug. 28, 2009 | 51.1 | Sep. 2, 2009 | | | |
| | | | Sep. 3, 2009 | 57.4 | Sep. 17, 2009 | 53.8 |
| 4/1/1 (SOP4.4) | Sep. 9, 2009 | 85 | Sep. 9, 2009 | 83.2 | Sep. 17, 2009 | 86.8 |
| 4/2/1 (SOP4.4) | Sep. 3, 2009 | 47.2 | Sep. 3, 2009 | 54.7 | Sep. 17, 2009 | 48.2 |
| 4/3/1 (SOP4.4) | Sep. 4, 2009 | 43.6 | Sep. 4, 2009 | 39 | Sep. 17, 2009 | 42.8 |
| 4/3/0.5 (SOP4.4) | May 10, 2009 | 44.3 | Sep. 10, 2009 | 41.0 | Sep. 17, 2009 | 40.0 |
| 4/3/1.5 (SOP4.4) | Sep. 11, 2009 | 40.5 | Sep. 11, 2009 | 38.3 | Sep. 17, 2009 | 37.5 |
| 4/2/0.5 (SOP4.4) | Sep. 16, 2009 | 53.1 | Sep. 16, 2009 | 54.3 | Sep. 17, 2009 | 55.7 |
| 4/2/1.5 (SOP4.4) | Sep. 14, 2009 | 50.00 | Sep. 14, 2009 | 52.7 | Sep. 17, 2009 | 50.9 |

TABLE 2

| | Zavrg Processed | | Zavrg Repeat 1 | | Zavrg Repeat 2 | | Zavrg Repeat 3 | |
|---|---|---|---|---|---|---|---|---|
| Formula/SOP | Date | Nm | Date | Nm | Date | Nm | Date | Nm |
| 0494-01-41 | Sep. 25, 2009 | 43.6 | Oct. 15, 2009 | 44.8 | Oct. 19, 2009 | 52.7 | Oct. 28, 2009 | |
| 0494-01-44 | Sep. 28, 2009 | 37.2 | Oct. 15, 2009 | 42.1 | Oct. 19, 2009 | 53.2 | Oct. 28, 2009 | 52.3 |

The 4:3:1.5 and 4:3:0 formulations were diluted with saline solution (dilution factor 1.6). 200 μL of suspension plus 120 μl, of saline. Diluted and undiluted samples were stored in stability chamber at 25° C. and 60% humidity. Particle sizes were assessed at 24, 48, and 96 hours later. Table 3 presents the stability results. Time dependent particle size increase was observed in both saline diluted and undiluted samples. From "0 hrs" to "48 hrs" the particle size increased by 5-8-nm for the 4:3:0 formulation and by 10-11-nm for the 4:3:1.5 formulation.

TABLE 3

| Lot # | Zavrg1 | Oct. 15, 2009 0 hrs Zavrg | Oct. 16, 2009 24 hrs Zavrg | Oct. 17, 2009 48 hrs Zavrg | Oct. 19, 2009 96 hrs Zavrg |
|---|---|---|---|---|---|
| 0494-01-41 |Sep. 25, 2009| | 42.1 | 44.8 | 46.7 | 46.7 | 52.7 |
| 0494-01-41 + Salne | | 45.3 | 47.0 | 46.0 | 50.5 |
| 0494-01-44 |Sep. 28, 2009| | 38.3 | 42.1 | 41.5 | 48.0 | 53.2 |
| 0494-01-44 + Salne | | 42.1 | 43.5 | 48.1 | 52.9 |

In some embodiments, a formulation of the invention may include from about 0.001% to about 20% (w/w) of Coenzyme Q10, more preferably between about 0.01% and about 15% and even more preferably between about 0.1% to about 10% (w/w) of Coenzyme Q10. In one embodiment a formulation includes about 4% (w/w) of Coenzyme Q10. In one embodiment a formulation includes about 8% (w/w) of Coenzyme Q10. In various embodiments, the formulation includes about 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of Coenzyme Q10. CoQ10 can be obtained from Kaneka Q10 as Kaneka Q10 (USP UBIDECARENONE) in powdered form (Pasadena, Tex., USA).

CoQ10 used in the methods exemplified herein have the following characteristics: residual solvents meet USP 467 requirement; water content is less than 0.0%, less than 0.05% or less than 0.2%; residue on ignition is 0.0%, less than 0.05%, or less than 0.2% less than; heavy metal content is less than 0.002%, or less than 0.001%; purity of between 98-100% or 99.9%, or 99.5%.

In some embodiments, the IV formulation presented herein, is a 4% sterile aqueous colloidal dispersion containing CoQ10 in a nanosuspension as prepared above. In certain embodiments the formulation is suitable for parenteral administration, including intravenous, intraperitoneal, orthotopical, intracranial, intramuscular, subcutaneous, intramedullary injections, as well as intrathecal, direct intraventricular, intranasal, or intraocular injections. In certain embodiments, the formulation contains CoQ10, dimyristoylphophatidylcholine, and poloxamer 188 in a ratio of 4:3:1.5 respectively that is designed to stabilize the nanosuspension of the particles. In some embodiments, the formulation includes a phosphate buffer saline solution which contains sodium phosphate dibasic, potassium phosphate monobasic, potassium chloride, sodium chloride and water for injection.

In certain embodiments, the concentration of CoQ10 in the formulation is between 1 mg/mL and 150 mg/mL. In one embodiment, the concentration of CoQ10 in the formulation is between 5 mg/mL and 125 mg/mL. In one embodiment, the concentration of CoQ10 in the formulation is between 10 mg/mL and 100 mg/mL. In one embodiment, the concentration of CoQ10 in the formulation is between 20 mg/mL and 90 mg/mL. In one embodiment, the concentration of CoQ10 is between 30 mg/mL and 80 mg/mL. In one embodiment, the concentration of CoQ10 is between 30 mg/mL and 70 mg/mL. In one embodiment, the concentration of CoQ10 is between 30 mg/mL and 60 mg/mL. In one embodiment, the concentration of CoQ10 is between 30 mg/mL and 50 mg/mL. In one embodiment, the concentration of CoQ10 is between 35 mg/mL and 45 mg/mL. It should be understood that additional ranges having any one of the foregoing values as the upper or lower limits are also intended to be part of this invention, e.g., between 10 mg/mL and 50 mg/mL, or between 20 mg/mL and 60 mg/mL.

In certain embodiments, the concentration of CoQ10 in the formulation is about 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90 or 95 mg/mL. In one embodiment, the concentration of CoQ10 in the formulation is about 50 mg/mL. In one embodiment, the concentration of CoQ10 in the formulation is about 60 mg/mL. In one embodiment, the concentration of CoQ10 in the formulation is about 30 mg/mL. In a preferred embodiment, the concentration of CoQ10 in the formulation is about 40 mg/mL. It should be understood that ranges having any one of these values as the upper or lower limits are also intended to be part of this invention, e.g. between 37 mg/mL and 47 mg/mL, or between 31 mg/mL and 49 mg/mL.

In some embodiments, the formulation's mean particle size is approximately between 10-nm and 200-nm. In other embodiments, the particle size ranges from approximately 10-nm to 100-nm, from approximately 30-nm to 80-nm or from approximately 35-nm to 40-nm. In some embodiments, the formulation's mean particle size ranges from approximately 10-nm to 150-nm. In one embodiment, the mean particle size ranges from approximately 10-nm to 125-nm. In other embodiments the mean particle size ranges from approximately 10-nm to 100-nm. In certain other embodiments the mean particle size ranges from approximately 10-nm to 90-nm, 10-nm to 80-nm, 10-nm to 70-nm, 10-nm to 60-nm, 10-nm of 50-nm, 10-nm to 45-nm, 10-nm to 40-nm, or 10-nm to 30-nm. In certain preferred embodiments the mean particle size ranges from approximately 20-nm to 80-nm. In one embodiment, the mean particle size ranges from approximately 20-nm to 70-nm. In one embodiment, the mean particle size ranges from approximately 20-nm to 60-nm. In one embodiment, the mean particle size ranges from approximately 20-nm to 50-nm. In one embodiment, the mean particle size ranges from approximately 25-nm to 45-nm. In one embodiment, the mean particle size ranges from approximately 30-nm to 45-nm. In certain other preferred embodiments the mean particle size ranges from approximately 35-nm to 45-nm. It should be understood that additional ranges having any one of the foregoing values as the upper or lower limits are also intended to be part of this invention, e.g., from 30-nm to 80-nm, or from 10-nm to 40-nm.

In certain embodiments, a kit is provided for the storage and handling of the nanosuspension colloidal formulation provided herein, whereby the nano-suspension is packaged in a vial and sealed with a chlorobutyl rubber stopper and an aluminum over cap.

V. TREATMENT OF ONCOLOGICAL DISORDERS

Formulations of the present disclosure may be utilized for the treatment of oncological disorders. Accordingly, the present invention provides methods of treating or preventing an oncological disorder in a subject, comprising intravenously administering the formulations of the invention to the subject in an amount sufficient to treat or prevent the oncological disorder, thereby treating or preventing the oncological disorder. The formulations of the invention may also be utilized for inhibiting tumor cell growth. Accordingly, the invention further provides methods of inhibiting tumor cell growth in a subject, comprising intravenously administering the formulations of the invention to the subject, such that tumor cell growth is inhibited. In certain embodiments, the subject is a human subject.

Such formulations may include the hydrophobic active agent, e.g., CoQ10 or its metabolites, in a pharmaceutically acceptable carrier. In some embodiments, such a formulation may include from about 0.001% to about 20% (w/w) of Coenzyme Q10, more preferably between about 0.01% and about 15% and even more preferably between about 0.1% to about 10% (w/w) of Coenzyme Q10. In one embodiment a formulation includes about 4% (w/w) of Coenzyme Q10. In one embodiment a formulation includes about 8% (w/w) of Coenzyme Q10. In various embodiments, the formulation includes about 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of Coenzyme Q10. As also noted herein, compositions of the present disclosure may be in a liquid form, capable of introduction into a subject by any means or route of administration within the purview of those skilled in the art. For example, compositions may be administered by routes of administration including, but not limited to, intravenous, intratumoral, combinations thereof, and the like.

In certain embodiments of the invention, methods are provided for treating or preventing an oncological disorder in a human by intravenously administering a Coenzyme Q10 formulation of the invention to the human such that treatment or prevention occurs, wherein the human is administered a dose of Coenzyme Q10 in the range of about 0.5 mg/kg to about 10,000 mg/kg, about 5 mg/kg to about 5,000 mg/kg, about 10 mg/kg to about 3,000 mg/kg. In one embodiment, Coenzyme Q10 is administered in the range of about 10 mg/kg to about 1,400 mg/kg. In one embodiment, Coenzyme Q10 is administered in the range of about 10 mg/kg to about 650 mg/kg. In one embodiment, Coenzyme Q10 is administered in the range of about 10 mg/kg to about 200 mg/kg. In various embodiments, Coenzyme Q10 is administered at a dose of about 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg. It should be understood that ranges having any one of these values as the upper or lower limits are also intended to be part of this invention, e.g., about 50 mg/kg a about 200 mg/kg, or about 650 mg/kg to about 1400 mg/kg. In one embodiment the administered dose is at least about 1 mg/kg, at least about 5 mg/kg, at least about 10 mg/kg, at least about 12.5 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 75 mg/kg, at least about 100 mg/kg, at least about 125 mg/kg, at least about 150 mg/kg, at least about 175 mg/kg, at least about 200 mg/kg, at least about 300 mg/kg, or at least about 400 mg/kg.

In one embodiment, the Coenzyme Q10 formulation is administered one time per week. In one embodiment, the Coenzyme Q10 formulation is administered 3 times per week. In another embodiment, the Coenzyme Q10 formulation is administered 5 times per week. In one embodiment, the Coenzyme Q10 formulation is administered once per day. In some embodiments, where the IV formulation is administered by infusion, the dosage is administered by infusion over about 1 hour, 2 hours, 3 hours, 4 hours or longer. In one embodiment, the IV formulation is administered by infusion over about 4 hours.

In another embodiment, the Coenzyme Q10 is administered in the form of a CoQ10 IV formulation at a dosage of between about 10 mg/kg and about 10,000 mg/kg of CoQ10, about 20 mg/kg to about 5000 mg/kg, about 50 mg/kg to about 3000 mg/kg, about 100 mg/kg to about 2000 mg/kg, about 200 mg/kg to about 1000 mg/kg, or about 300 mg/kg to about 500 mg/kg, wherein the CoQ10 formulation comprises between about 1% and 10% of Coenzyme Q10. In one embodiment, the CoQ10 formulation comprises about 4% of Coenzyme Q10. In one embodiment, the CoQ10 IV formulation comprises about 8% of Coenzyme Q10. In other embodiments, the CoQ10 IV formulation comprises about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of Coenzyme Q10. It should be understood that ranges having any one of these values as the upper or lower limits are also intended to be part of this invention.

As used herein, "oncological disorder" refers to all types of cancer or neoplasm or malignant tumors found in humans, including, but not limited to: leukemias, lymphomas, melanomas, carcinomas and sarcomas. As used herein, the terms or language "oncological disorder", "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

The term "sarcoma" generally refers to a tumor which is made up of a substance like the embryonic connective tissue and is generally composed of closely packed cells embedded in a fibrillar or homogeneous substance. Examples of sarcomas which can be treated with a colloidal dispersion of CoQ10 in an IV formulation include, for example, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the colloidal dispersions of CoQ10 in IV formulation include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the colloidal dispersions of CoQ10 in IV formulation, as described herein, include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous Carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, merkel cell carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Where utilized to treat cancer, the formulations may be in a pharmaceutically acceptable carrier that may be administered in a therapeutically effective amount to an area of oncogenesis as either a mono-therapy, in combination with at least one other chemotherapeutic agent for a given indication, in combination with radiotherapy, following surgical intervention to radically remove a tumor, in combination with other alternative and/or complementary acceptable treatments for cancer, and the like. In certain embodiments, the present disclosure also provides a method for reactivating a mutated/inactivated p53 protein by administering to an area of oncogenesis in a patient a composition of the present disclosure.

The present disclosure also provides methods for modulating proteins implicated in oncogenesis by administering to an area of oncogenesis in a patient a composition of the present disclosure. Such proteins which may be modulated by compositions of the present disclosure include, but are not limited to: Bcl-2 protein; Bax protein; Bid protein; Bim protein; Bad protein; Bak protein; mcl-1 protein; Bcl-xl protein; Bcl-xs protein; Bcl-w protein; Bik protein; Bok protein; BimL protein; A1 protein; Hrk protein; Bik protein; BNIP3 protein; Bik protein; Noxa protein; Puma protein; VEGF protein; FGF-1/FGF-2 protein; Hif-α protein; angiostatin protein; TGF-β protein; smad proteins; cdk (cyclin-dependent kinases); the PI3K/akt complex. In other embodiments, compositions of the present disclosure may be utilized to regulate and/or restore a healthy apoptosis state in cancer cells. Mitochondrial dysfunction and dysregulation of apoptosis are implicated in many diseases such as cancer and neurodegeneration. Respiratory chain (RC) dysfunction may have a role in apoptosis, as demonstrated using mitochondrial DNA mutations as genetic models. Although some mutations eliminate the entire RC, others target specific complexes, resulting in either decreased or complete loss of electron flux, which leads to impaired respiration and adenosine triphosphate (ATP) synthesis. Despite these similarities, significant differences in responses to apoptotic stimuli emerge. Cells lacking RC are protected against both mitochondrial- and endoplasmic reticulum (ER) stress-induced apoptosis. Cells with RC, but unable to generate electron flux, are protected against mitochondrial apoptosis, although they have increased sensitivity to ER stress. Finally, cells with a partial reduction in electron flux have increased apoptosis under both conditions. RC modulates apoptosis in a context-dependent manner independent of ATP production and that apoptotic responses are the result of the interplay between mitochondrial functional state and environmental cues.

The execution of apoptosis and communication between oncogenic factors may also be mediated by released factors such as cytochrome C, Endo G, or AIF through mitochondrial membrane pores which open upon membrane depolarization. Cancer cells also generate excessive lactate in the presence of oxygen (aerobic glycolysis). It now appears that this phenomenon is the product of two factors: a return to the more glycolytic metabolism of the embryo and alterations in oxidative phosphorylation (OXPHOS) to increase mitochondrial reactive oxygen species (ROS) production. Alterations in the Ras-PI3K-Akt signal transduction pathway can result in induction of hexokinase II and its attachment to mitochondrial porin redirecting mitochondrial ATP to phosphorylate glucose and drive glycolysis. Furthermore, partial inhibition of OXPHOS by mitochondrial gene mutations (germ-line or somatic) can reduce electron flux through the electron transport chain, increasing mitochondrial ROS production. The increased ROS mutagenizes nuclear proto-oncogenes (initiation) and drives nuclear replication (promotion), resulting in cancer. Therefore, hexokinase II and mitochondrial ROS may be useful alternate targets for cancer therapeutics. Metabolic flux as it relates to cancer is compromised in an oncogenic state and shifts towards a glycolytic state. A cancer cell's survival is vitally dependent on glucose metabolism and low oxygen levels. More perplexing is that mitochondrial activity is significantly attenuated to the point of dormancy. Oxidative phosphorylation usually associated with Complex 1-IV that accepts electrons from the Citric Acid Cycle (TCA) is essentially shut down. There is a marked increase in the amount of free radicals and lactate dehydrogenase activity. Hence, the cancer cell is in a state of: (1) Decreased oxygen (Hypoxia); (2) Increase free-radical formation; (3) Dysregulated apoptosis (cell death); (4) Dependence of glucose metabolism; (5) Increased blood vessel formation; and (6) Altered immune recognition (auto-regulatory state commences).

In general, the CoQ10 N formulation described herein may be used to prophylactically or therapeutically treat any neoplasm. In a particular embodiment, the formulation is used to treat solid tumors. In various embodiments of the invention, CoQ10 is used for treatment or prevention of cancer of the brain, central nervous system, head and neck, prostate, breast, testicular, pancreas, liver, colon, bladder, urethra, gall bladder, kidney, lung, non-small cell lung, melanoma, mesothelioma, uterus, cervix, ovary, sarcoma, bone, stomach and Medulloblastoma. In one embodiment, the CoQ10 N formulations described herein may be used to treat a chloroleukemia, e.g., a primary chloroleukemia or a secondary or metastatic chloroleukemia, e.g., that presents, migrates or metastasizes to a particular organ such as, e.g., the lung, the liver or the central nervous system.

However, treatment using CoQ10 N formulations of the invention is not limited to the foregoing types of cancers. Examples of cancers amenable to treatment with CoQ10 formulations of the invention include, but are not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. In one embodiment, a CoQ10 N formulation described herein may be used to treat or prevent various types of skin cancer (e.g., Squamous cell Carcinoma or Basal Cell Carcinoma), pancreatic cancer, breast cancer, prostate cancer, liver cancer, or bone cancer. In one embodiment, CoQ10 is used for treatment of a skin oncological disorder including, but not limited to, squamous cell carcinomas (including SCCIS (in situ) and more aggressive squamous cell carcinomas), basal cell carcinomas (including superficial, nodular and infiltrating basal cell carcinomas), melanomas, and actinic keratosis. In one embodiment, the oncological disorder or cancer which can be treated with CoQ10 is not melanoma. In one embodiment, the oncological disorder is merkel cell carcinoma (MCC).

In certain embodiments, the effect CoQ10 may have on cancer cells may depend, in part, on the various states of metabolic and oxidative flux exhibited by the cancer cells. CoQ10 may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the development of a cancer cell. In some embodiments, the interaction of CoQ10 with glycolytic and oxidative flux factors may enhance the ability of CoQ10 to exert its restorative apoptotic effect in cancer while establishing viable drug targets for drug discovery and development. While the present disclosure has focused on CoQ10 and its metabolites, other compounds related to CoQ10 which may be administered instead of, or in combination with, CoQ10 include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxyphenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like.

In one embodiment, IV administration of the colloidal dispersion of CoQ10 as described herein, reduces tumor size, inhibits tumor growth and/or prolongs the survival time of a tumor-bearing subject. Accordingly, this invention also relates to a method of treating tumors in a human or other animal by intravenously administering to such human or animal an effective, non-toxic amount of CoQ10. One skilled in the art would be able, by routine experimentation, to determine what an effective, non-toxic amount of CoQ10 would be for the purpose of treating malignancies. For example, a therapeutically active amount of CoQ10 may vary according to factors such as the disease stage (e.g., stage I versus stage 1V), age, sex, medical complications (e.g., immunosuppressed conditions or diseases) and weight of the subject, and the ability of the CoQ10 to elicit a desired response in the subject. The dosage regimen may be adjusted to provide the optimum therapeutic response. For example, several divided doses may be administered daily, or the dose may be proportionally reduced as indicated by the exigencies of the therapeutic situation.

The invention also provides, in another aspect, methods for treating or preventing aggressive oncological disorders in humans. These methods include intravenously administering Coenzyme Q10 to the human at a therapeutically effective dose, so that treatment or prevention of the aggressive oncological disorder occurs. In one embodiment, these methods include intravenously administering Coenzyme Q10 to the human at a selected lower dosage than a dosage regimen used or selected for less aggressive or non-aggressive oncological disorder, so that treatment or prevention of the aggressive oncological disorder occurs. In certain embodiments the aggressive oncological disorder includes pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, liver cancer, lung cancer, osteosarcoma, androgen-independent prostate cancer, ovarian cancer and non-Hodgkin's Lymphoma.

In a related aspect, the invention provides a method for treating or preventing a non-aggressive oncological disorder in a human. These methods include intravenously administering Coenzyme Q10 to the human at a therapeutically effective dose, so that treatment or prevention of the non-aggressive oncological disorder occurs. In one embodiment, these methods include administering Coenzyme Q10 to the human at a selected higher dosage over a dosage regimen used or selected for aggressive oncological disorders so that treatment or prevention of the non-aggressive oncological disorder occurs. In certain embodiments, the non-aggressive oncological disorder includes non-metastatic breast cancer, androgen-dependent prostate cancer, small cell lung cancer and acute lymphocytic leukemia.

In some embodiments of the invention, the treatment or prevention of the oncological disorder occurs via an interaction of CoQ10 with a protein selected from the group consisting of HNF4-alpha, Bcl-xl, Bcl-xS, BNIP-2, Bcl-2, Birc6, Bcl-2-L11 (Bim), XIAP, BRAF, Bax, c-Jun, Bmf, PUMA, cMyc, transaldolase 1, COQ1, COQ3, COQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II. In some embodiments the oncological disorder is selected from the group consisting of leukemia, a lymphoma, a melanoma, a carcinoma or a sarcoma.

In certain embodiments of the invention, the oncological disorder is selected from the group consisting of a leukemia, a lymphoma, a melanoma, a carcinoma and a sarcoma.

In certain embodiments of the invention, the methods further include a treatment regimen which includes any one of or a combination of surgery, radiation, hormone therapy, antibody therapy, therapy with growth factors, cytokines, and chemotherapy.

The resulting CoQ10 nanoparticles can also serve as a carrier systems for other lipophilic drugs. Vitamins A and K3 can be incorporated therein, for example.

VI. COMBINATION THERAPIES

In certain embodiments, the formulations of the invention, e.g., the CoQ10 I.V. formulations, can be used in combination therapy with at least one other therapeutic agent. CoQ10 and/or pharmaceutical formulations thereof and the other therapeutic agent can act additively or, more preferably, synergistically. In one embodiment, CoQ10 and/or a formulation thereof is administered concurrently with the administration of another therapeutic agent. In another embodiment, a compound and/or pharmaceutical formulation thereof is administered prior or subsequent to administration of another therapeutic agent. In one embodiment, the CoQ10 and additional therapeutic agent active synergistically. In one embodiment, the CoQ10 and additional therapeutic agent act additively.

In one embodiment, the therapeutic methods of the invention further comprise administration of one or more additional agents, e.g., one or more therapeutic agents. For example, in one embodiment, an additional agent for use in the therapeutic methods of the invention is a chemotherapeutic agent.

Chemotherapeutic agents generally belong to various classes including, for example: 1. Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fiuropyrimidines, purine or pyrimidine analogues such as 5-fluorouracil, capecitabine, gemcitabine, methotrexate and edatrexate; 5. Topoisomerase I inhibitors, such as topotecan, irinotecan, and 9-nitrocamptothecin, and camptothecin derivatives; and 6. Platinum compounds/complexes, such as cisplatin, oxaliplatin, and carboplatin; Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I 1, 1O-hydroxy-7-ethyl-camptothecin (SN38), dacarbazine, S-I capecitabine, ftorafur, 5' deoxyfluorouridine, UFT, eniluracil, deoxycytidine, 5-azacytosine, 5-azadeoxycytosine, allopurinol, 2-chloro adenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10, 11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof which are readily apparent to one of skill in the art based on the appropriate standard of care for a particular tumor or cancer.

In another embodiment, an additional agent for use in the combination therapies of the invention is a biologic agent.

Biological agents (also called biologies) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and 2. Enzymes, proteins, peptides, polyclonal and/or monoclonal antibodies, such as interleukins, interferons, colony stimulating factor, etc.

In one embodiment, the biologic is an interferon. Interferons (IFN) are a type biologic agent that naturally occurs in the body. Interferons are also produced in the laboratory and given to cancer patients in biological therapy. They have been shown to improve the way a cancer patient's immune system acts against cancer cells.

Interferons may work directly on cancer cells to slow their growth, or they may cause cancer cells to change into cells with more normal behavior. Some interferons may also stimulate natural killer cells (NK) cells, T cells, and macrophages which are types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory.

Some interleukins stimulate the growth and activity of immune cells, such as lymphocytes, which work to destroy cancer cells.

In another embodiment, the biologic is a colony-stimulating factor.

Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells.

With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells.

When cancer-destroying agents are introduced into the body, they seek out the antibodies and kill the cancer cells. Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with an environmental influencer for the treatment of cancer. In one embodiment, the anti-HER2 antibody is Trastuzumab (Herceptin). Other examples of antibodies which may be used in combination with an environmental influencer for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with an environmental influencer for the treatment of cancer. In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab. Numerous other anti-tumor antibodies are known in the art and would be understood by the skilled artisan to be encompassed by the present invention.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. For example, recombinant human Apo2/TRAIL (Genentech) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is an antisense nucleic acid molecule.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a biologic agent is an siRNA molecule, e.g., of a molecule that enhances angiogenesis, e.g., bFGF, VEGF and EGFR. In one embodiment, a biologic agent that inhibits angiogenesis mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. MoI Therapy. 7:9-10; McManus M T and Sharp P A. 2002. Nat Rev Genet. 3.737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more chemistries for use in antisense RNA can be employed in molecules that mediate RNAi.

The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J J. (1995) Br. Med. Bull. 51.217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences of a molecule that enhances angiogenesis, antisense nucleic acids of the invention can be designed according to the rules of Watson and Crick base pairing. The antisense nucleic acid molecule can be complementary to the entire coding region of the mRNA, but more preferably is an oligonucleotide which is antisense to only a portion of the coding or noncoding region of the mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an a-anomeric nucleic acid molecule. An a-anomeric nucleic acid molecule forms specific double-stranded hybrids with complementary RNA in which, contrary to the usual a-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In another embodiment, an antisense nucleic acid of the invention is a compound that mediates RNAi. RNA interfering agents include, but are not limited to, nucleic acid molecules including RNA molecules which are homologous to the target gene or genomic sequence, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

Nucleic acid molecules encoding molecules that, e.g., inhibit angiogenesis, may be introduced into the subject in a form suitable for expression of the encoded protein in the cells of the subject may also be used in the methods of the invention. Exemplary molecules that inhibit angiogenesis include, but are not limited to, TSP-I, TSP-2, IFN-g, IFN-a, angiostatin, endostatin, tumastatin, canstatin, VEGI, PEDF, vasohibin, and the 16 kDa fragment of prolactin 2-Methoxyestradiol (see, Kerbel (2004) J. Clin Invest 114: 884, for review).

For example, a full length or partial cDNA sequence is cloned into a recombinant expression vector and the vector is transfected into a cell using standard molecular biology techniques. The cDNA can be obtained, for example, by amplification using the polymerase chain reaction (PCR) or by screening an appropriate cDNA library. The nucleotide sequences of the cDNA can be used for the design of PCR primers that allow for amplification of a cDNA by standard PCR methods or for the design of a hybridization probe that can be used to screen a cDNA library using standard hybridization methods. Following isolation or amplification of the cDNA, the DNA fragment is introduced into a suitable expression vector.

Exemplary biologic agents for use in the methods of the invention include, but are not limited to, gefitinib (Iressa), anastrazole, diethylstilbesterol, estradiol, premarin, raloxifene, progesterone, norethynodrel, esthisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-IBBL, anti-CD40, anti-CD154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional agent, e.g., 1, 2, 3, 4, 5, may be administered in combination with the CoQ10 formulations of the invention. For example, in one embodiment two chemotherapeutic agents may be administered in combination with CoQ10. In another embodiment, a chemotherapeutic agent, a biologic agent, and CoQ10 may be administered.

Various forms of the biologic agents may be used. These include, without limitation, such forms as proform molecule, uncharged molecules, molecular complexes, salts, ethers, esters, amides, and the like, which are biologically activated when implanted, injected or otherwise inserted into the tumor.

The invention will be further understood by the following example(s). However, those skilled in the art will readily appreciate that the specific experimental details are only illustrative and are not meant to limit the invention as described herein, which is defined by the claims which follow thereafter. The contents of any patents, patent applications, patent application publications and references cited throughout this specification are hereby incorporated by reference in their entireties.

EXAMPLES

The following examples provide exemplary formulations for the preparation of the colloidal dispersions of CoQ10.

Example 1

Formulation CoQ10/DMPC/P188 (4:3:0-SOP4.1): (a) 4 g CoQ10 is added to 93 mL of 65° C. water and mixed for 10 minutes to form a CoQ10/water mixture (M1); (b) 3 g of DMPC (powder) was added to the M1 and mixed for 10 more minutes at 65° C. to form CoQ10/water/DMPC mixture (M2); (c) high shear mixer, 7000 rpm at 65° C. is applied to M2 for 2 minutes; (d) a Microfluidizer chamber is pre-heated to 65° C.; (e) M2 is processed in the Microfluidizer at 65° C. and 28,000 PSI.

Example 2

Formulation CoQ10/DMPC/P188 (4:2:0-SOP4.2): (a) 4 g of CoQ10 is added to 94 mL of 65° C. water and mixed for 10 minutes to form mixture M1; (b) 3 g of DMPC (powder) is added to M1 and mixed for 10 more minutes at 65° C. to form mixture M2; (c) high shear mixer at 8,000 rpm is applied to M2 for 2 minutes at 65° C.; (d) a Microfluidizer processing chamber is pre-heated to 65° C.; (e) M2 is processed in the pre-heated Microfluidizer at 65° C. and 30,000 PSI.

Example 3

Formulation CoQ10/DMPC/P188 (4:3:1-SOP4.3): (a) 4 g of CoQ10 is added to 92 mL of 65° C. water and mixed for 10 minutes to form mixture M1; (b) 3 g DMPC (powder) is added to M1 and mixed for 10 more minutes at 65° C. to form mixture M2; (c) high shear mixer at 8,000 rpm is applied to M2 for 2 minutes at 65° C.; (d) 1 g of P188 (powder) is added to M2 and mixed for 10 more minutes at 65° C. to form mixture M3; (e) high shear mixer at 8,000 rpm is then applied to M3; (f) a Microfluidizer chamber is then pre-heated to 65° C.; (g) M3 is then processed in a Microfluidizer at 65° C. and 30,000 PSI.

Example 4

Formulation CoQ10/DMPC/P188 (4:2:1-SOP4.4): (a) 4 g of CoQ10 is added to 93 mL of 65° C. water and mixed for 10 minutes to form mixture M1; (b) 2 g of DMPC (powder) is added to M1 and mixed for 10 more minutes at 65° C.; (c) high shear mixer at 8,000 rpm is applied to M2 for 2 minutes at 65° C.; (d) 1 g P188 (powder) is then added to the sheared M2 mixture and mixed for 10 more minutes at 65 C to form mixture M3; (e) a Microfluidizer is pre-heated to 65° C.; (f) M3 is then processed in the Microfluidizer at 65° C. and 30,000 PSI.

Example 5

Formulation CoQ10/DMPC/P188 (4:3:1-SOP4.4): (a) 4 g of CoQ10 is added to 92 mL of 65° C. water and mixed for 10 minutes to form mixture M1; (b) 3 g of DMPC (powder) is then added to M1 and mixed for 10 more minutes at 65° C. to form mixture M2; (c) high shear mixer at 8,000 rpm is then applied to M2 at 65° C. for 2 minutes; (d) 1 g P188 (powder) is added to the sheared M2 mixture and mixed for 10 more minutes at 65° C. to form mixture M3; a Microfluidizer processing chamber is then pre-heated to 65° C.; mixture M3 is then processed in the Microfluidizer at 65° C. and 30,000 PSI.

Example 6

Formulation CoQ10/DMPC/P188 (4:1:0-SOP4.4): (a) 4 g of CoQ10 is added to 95 mL of 65° C. water and mixed for 10 minutes to form mixture M1; (b) 1 g of DMPC (powder) is added to M1 and mixed for 10 minutes to form mixture M2; (c) high shear mixer at 8,000 rpm is applied to M2 for 2 minutes at 65° C.; (c) a Microfluidizer processing chamber is pre-heated to 65° C.; (d) the sheared M2 mixture is processed in the Microfluidizer at 65° C. and 30,000 PSI.

Example 7

Formulation CoQ10/DMPC/P188 (4:1:1-SOP4.4): (a) 4 g of CoQ10 is added to 94 mL of 65° C. water and mixed for 10 minutes to form mixture M1; (b) 1 g of DMPC (powder) is added to M1 and mixed for 10 minutes to form mixture M2; (c) high shear mixer at 8,000 rpm is applied to M2 for 2 minutes at 65° C.; (d) 1 g of P188 (powder) is added to the sheared M2 mixture and mixed for 10 more minutes at 65° C. to form mixture M3; (e) a Microfluidizer processing chamber is pre-heated to 65° C.; (0 the M3 mixture is processed in the Microfluidizer at 65° C. and 30,000 PSI.

Example 8

Formulation CoQ10/DMPC/P188 (4:3:0.5-SOP4.4): (a) 4 g of CoQ10 is added to 92 mL of 65° C. water and mixed for 10 minutes to form mixture M1; (b) 3 g of DMPC (powder) is added to M1 and mixed for 10 minutes to form mixture M2; (c) high shear mixer at 8,000 rpm is applied to M2 for 2 minutes at 65° C.; (d) 0.5 g of P188 (powder) is added to the sheared M2 mixture and mixed for 10 more minutes at 65° C. to form mixture M3; (e) a Microfluidizer processing chamber is pre-heated to 65° C.; (0 the M3 mixture is processed in the Microfluidizer at 65° C. and 30,000 PSI.

Example 9

Formulation CoQ10/DMPC/P188 (4:3:1.5-SOP4.4): (a) 4 g of CoQ10 is added to 91.5 mL of 65° C. water and mixed for 10 minutes to form mixture M1; (b) 3 g of DMPC (powder) is added to M1 and mixed for 10 minutes to form mixture M2; (c) high shear mixer at 8,000 rpm is applied to M2 for 2 minutes at 65° C.; (d) 1.5 g of P188 (powder) is added to the sheared M2 mixture and mixed for 10 more minutes at 65 C to form mixture M3; (e) a Microfluidizer processing chamber is pre-heated to 65° C.; (f) the M3 mixture is processed in the Microfluidizer at 65° C. and 30,000 PSI.

Example 10

Formulation CoQ10/DMPC/P188 (4:2:1.5-SOP4.4): (a) 4 g of CoQ10 is added to 92 mL of 65° C. water and mixed for 10 minutes to form mixture M1; (b) 2 g of DMPC (powder) is added to M1 and mixed for 10 minutes to form mixture M2; (c) high shear mixer at 8,000 rpm is applied to M2 for 2 minutes at 65° C.; (d) 1.5 g of P188 (powder) is added to the sheared M2 mixture and mixed for 10 more minutes at 65° C. to form mixture M3; (e) a Microfluidizer processing chamber is pre-heated to 65° C.; (0 the M3 mixture is processed in the Microfluidizer at 65° C. and 30,000 PSI.

Figure 17:
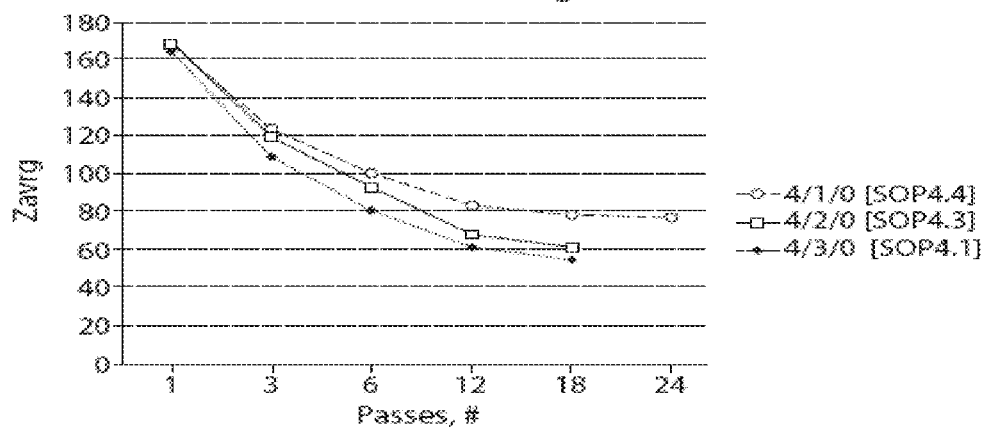
FIG. 17 depicts the effect of number of passes on the size of the colloidal nano-particles where the formulation ratio of CoQ10:DMPC:Poloxamer is 4:1:0, 4:2:0 and 4:3:0.

As can be seen from FIG. 17, the processing of formulation 4:3:0-SOP4.1 mixture results in particle sizes of about 50-nm after 18 passes; formulation 4:2:0-SOP4.2 led to particle sizes of about 60-nm after 18 passes; formulation 4:1:0-SOP4.4 led to particle sizes of about 80-nm after 18 passes.

Figure 18:
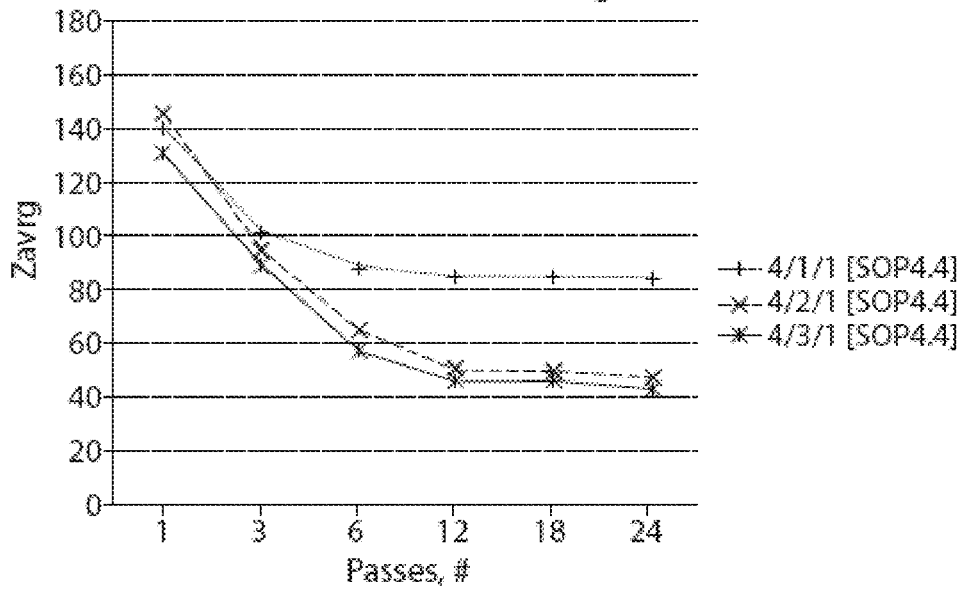
FIG. 18 depicts the effect of number of passes on the size of the colloidal nano-particles where the formulation ratio of CoQ10:DMPC:Poloxamer is 4:1:1, 4:2:1 and 4:3:1.

The addition of poloxamer 188 (P188) to the mixture, as depicted in FIG. 18 shows that formulation 4:1:1-SOP4.4 results in particle sizes of about 80-nm after 12 passes; formulation 4:2:1-SOP4.4 results in particle sizes of about 50-nm after 12 passes; and 4:3:1-SOP4.4 results in particle sizes of about 40-nm after 12 passes. The DMPC/CoQ10 and DMPC/P188 ratios are therefore critical factors in determining the particle sizes. While not wishing to be bound by any specific theory, it is believed that the P188 softens the DMPC layer and facilitates initial formation of the smaller size particles.

Figure 19:
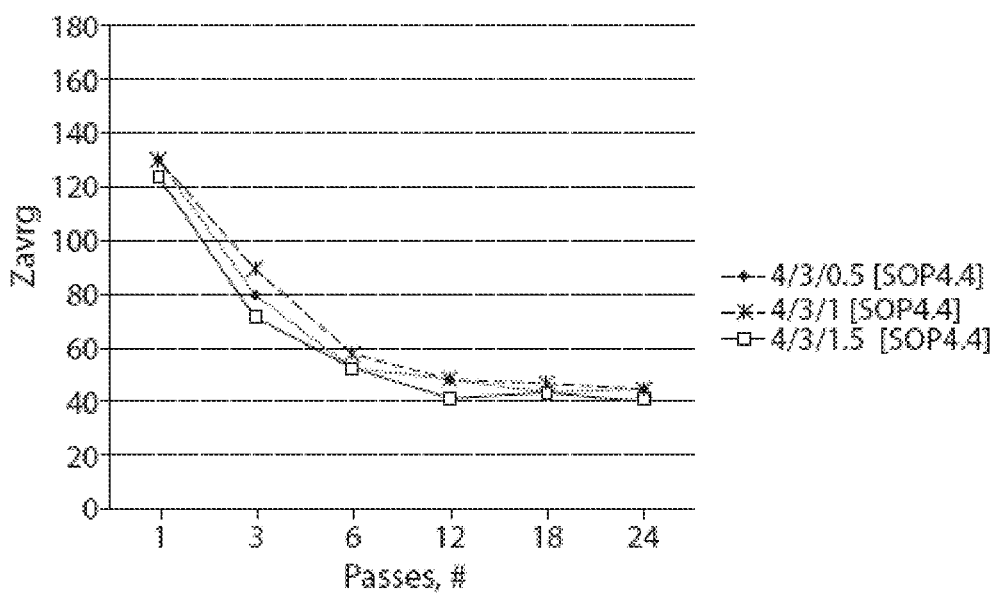
FIG. 19 depicts the effect of number of passes on the size of the colloidal nano-particles where the formulation ratio of CoQ10:DMPC:Poloxamer is 4:3:0.5, 4:3:1 and 4:3:1.5.

In certain embodiments, the CoQ10/DMPC ratios of 4:3 and 4:2 were adjusted with varying amounts of P188. As depicted in FIG. 19, there was no significant effect of P188 concentration on the final particle size when the CoQ10/DMPC ration was 4:3.

Figure 20:
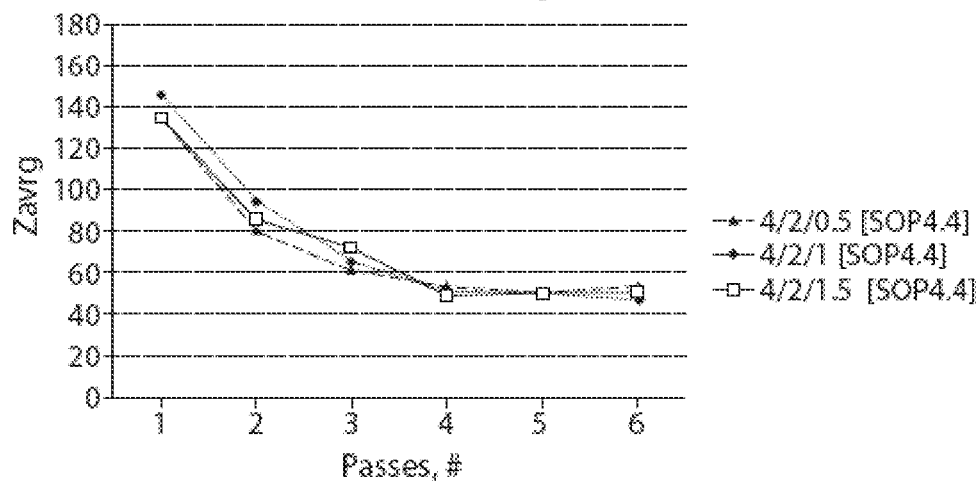
FIG. 20 depicts the effect of number of passes on the size of the colloidal nano-particles where the formulation ratio of CoQ10:DMPC:Poloxamer is 4:2:0.5, 4:2:1 and 4:2:1.5.
Figure 21:
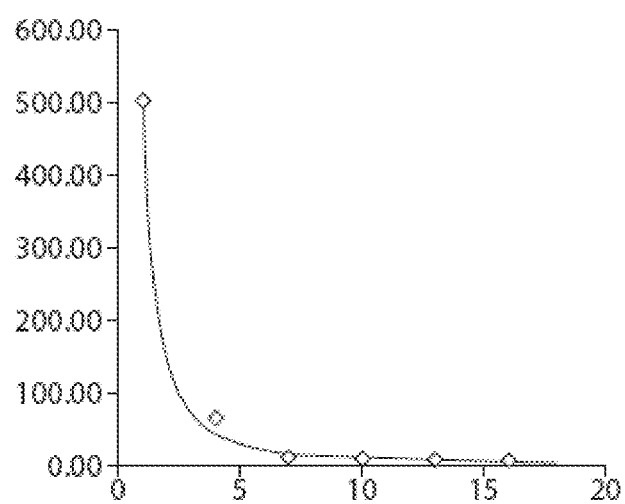
FIG. 21 depicts, in graphical form, the average concentration of CoQ10 in the plasma over time (min) based on the administration of formulation 1 which included no poloxamer.

Similarly, varying the P188 concentration for CoQ10/DMPC 4:2 ration had insignificant effects on the particle size as is seen in FIG. 20.

The following examples provide exemplary embodiments demonstrating the uses and methods related to the administration of the CoQ10 IV formulation of the colloidal dispersions of CoQ10 provided herein.

Example 11

Determination of pK of Coenzyme Q10: 39 female SCID.CB 17 mice, 4-6 weeks old, were acclimated for 3-5 days prior to study dosing. The 39 mice were placed into 13 groups of 3 each by average body weight taken prior to dosing day. On day 0, groups 1-6 were administered a single dose of the formulation as described herein without poloxamer (formulation 1). Groups 1-6 were administered 100 mg/kg by IV injection of formulation 1 and plasma and tissue (spleen, liver, pancreas, lungs and brain) samples were taken at 2 h, 4 h, 8 h, 12 h, 24 h and 36 h post dosing. On day 0, groups 7-12 were administered a single dose of the CoQ10 formulation as described herein with poloxamer (formulation 2). Groups 7-12 were administered 100 mg/kg by IV injection of formulation 2 and plasma and tissue (spleen, liver, pancreas, lungs and brain) samples were recovered at 2 h, 4 h, 8 h, 12 h, 24 h and 36 h post dosing. Group 13 received no treatment.

Figure 22:
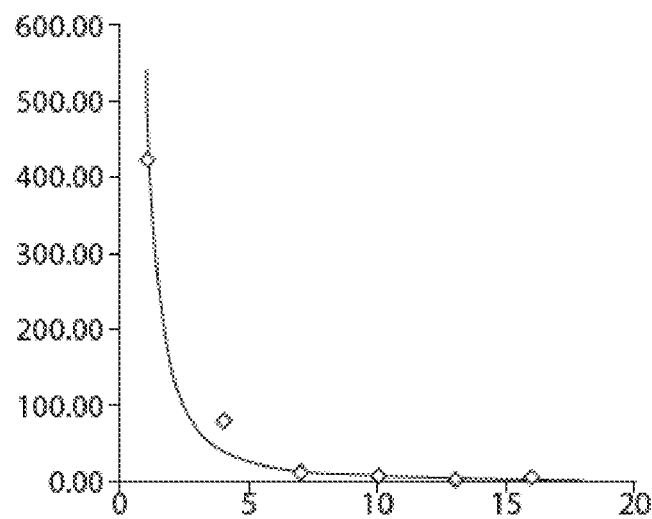
FIG. 22 depicts, in graphical form, the average concentration of CoQ10 in the plasma over time (min) based on the administration of formulation II which included poloxamer.
Figure 23:
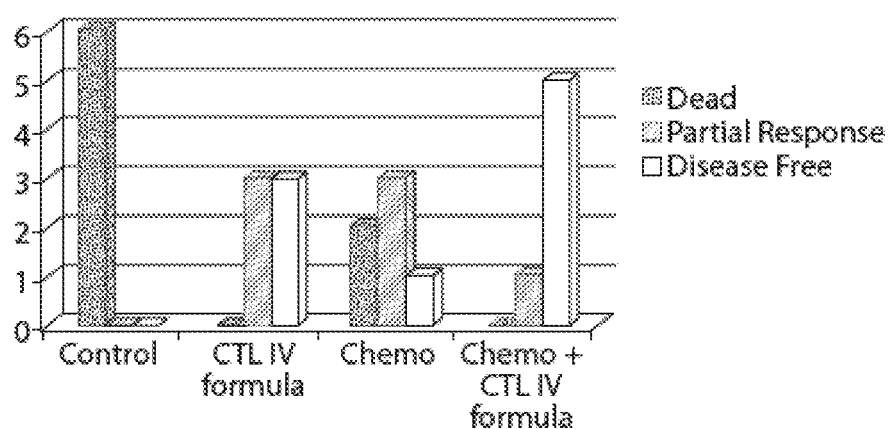
FIG. 23 depicts, in graphical form, the efficacy of the IV formulation of CoQ10 nano-particles in treating the liver clone of malignant chloroma with a 4:3:1.5 ratio of CoQ10:DMPC:poloxamer 188 in comparison to chemotherapy alone and in combination with chemotherapy.
Figure 24:
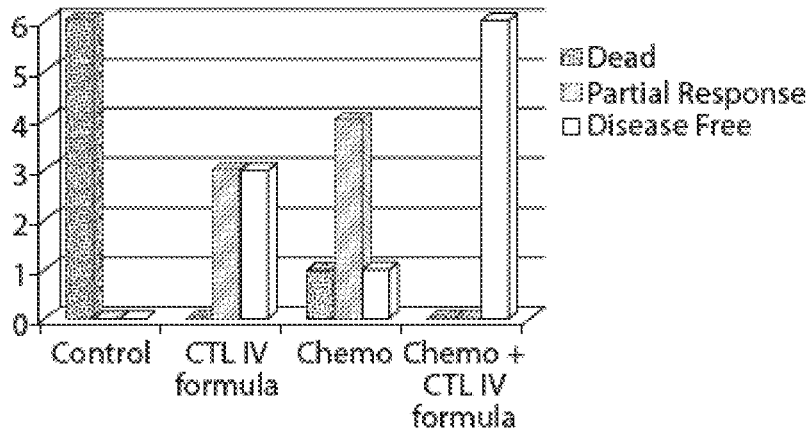
FIG. 24 depicts, in graphical form, the efficacy of the N formulation of CoQ10 nano-particles in treating the lung clone of malignant chloroma with a 4:3:1.5 ratio of CoQ10.

A biological assay was conducted to quantify the levels of CoQ10 in the mouse plasma, liver, lung, spleen, pancreas and brain tissues by using LC/MS/MS. The CoQ10 was quantified at the range of 1-600 μg/mL for mouse plasma and at the range of 0.25-100 μg/mL for mouse tissues up to 36 hours following IV administration. FIGS. 22 and 23 provide the concentration profile of the CoQ10 formulation 1 in the plasma. FIGS. 24 and 25 provide the concentration profile of the CoQ10 formulation 2 in the plasma. FIGS. 26 and 27 provide the liver concentration for formulations 1 and 2, respectively. FIGS. 28 and 29 provide the lung concentration for formulation 1 and 2, respectively. FIGS. 30 and 31 provide the spleen concentration for formulation 1 and 2, respectively. FIGS. 32 and 33 provide the pancreas concentration for formulation 1 and 2, respectively. FIGS. 34 and 35 provide the brain concentration for formulation 1 and 2, respectively.

TABLE 4

| Sample NO. | Sample ID (Formulation I) | Time (hour) | Conc. (μg/mL) | Ave. Conc. (μg/mL) |
|---|---|---|---|---|
| 1 | Plasma-G13-Predose-1356 | 0 | 0.00 | 0.00 |
| 2 | Plasma-G13-Predose-1354 | 0 | 0.00 | |
| 3 | Plasma-G13-Predose-1366 | 0 | 0.00 | |
| 4 | Plasma-F1-G1-1370-2 h | 2 | 506.58 | 503.39 |
| 5 | Plasma-F1-G1-1344-2 h | 2 | 570.76 | |
| 6 | Plasma-F1-G1-1373-2 h | 2 | 432.83 | |
| 7 | Plasma-F1-G2-1360-4 h | 4 | 25.86 | 62.70 |
| 8 | Plasma-F1-G2-1374-4 h | 4 | 129.70 | |
| 9 | Plasma-F1-G2-1376-4 h | 4 | 32.54 | |
| 10 | Plasma-F1-G3-1351-8 h | 8 | 5.50 | 7.74 |
| 11 | Plasma-F1-G3-1371-8 h | 8 | 7.14 | |
| 12 | Plasma-F1-G3-1359-8 h | 8 | 10.59 | |
| 13 | Plasma-F1-G4-1352-12 h | 12 | 10.92 | 8.21 |
| 14 | Plasma-F1-G4-1347-12 h | 12 | 8.33 | |
| 15 | Plasma-F1-G4-1377-12 h | 12 | 5.37 | |
| 16 | Plasma-F1-G5-1353-24 h | 24 | 4.27 | 5.13 |
| 17 | Plasma-F1-G5-1369-24 h | 24 | 6.14 | |
| 18 | Plasma-F1-G5-1378-24 h | 24 | 4.97 | |
| 19 | Plasma-F1-G6-1357-36 h | 36 | 5.31 | 5.12 |
| 20 | Plasma-F1-G6-1372-36 h | 36 | 5.87 | |
| 21 | Plasma-F1-G6-1367-36 h | 36 | 4.18 | |

TABLE 5

| Sample NO. | Sample ID (Formulation II) | Time (hour) | Conc. (μg/mL) | Ave. Conc. (μg/mL) |
|---|---|---|---|---|
| 1 | Plasma-G13-Predose-1356 | 0 | 0.00 | 0.00 |
| 2 | Plasma-G13-Predose-1354 | 0 | 0.00 | |
| 3 | Plasma-G13-Predose-1366 | 0 | 0.00 | |
| 4 | Plasma-F2-G7-1345-2h | 2 | 410.81 | 423.24 |
| 5 | Plasma-F2-G7-1368-2h | 2 | 406.94 | |
| 6 | Plasma-F2-G7-1375-2h | 2 | 451.98 | |
| 7 | Plasma-F2-G8-1358-4h | 4 | 88.82 | 79.01 |
| 8 | Plasma-F2-G8-1361-4h | 4 | 54.78 | |
| 9 | Plasma-F2-G8-1364-4h | 4 | 93.42 | |
| 10 | Plasma-F2-G9-1346-8h | 8 | 7.40 | 11.73 |
| 11 | Plasma-F2-G9-1350-8h | 8 | 15.80 | |
| 12 | Plasma-F2-G9-1341-8h | 8 | 11.99 | |
| 13 | Plasma-F2-G10-1348-12h | 12 | 9.32 | 6.64 |
| 14 | Plasma-F2-G10-1355-12h | 12 | 3.89 | |
| 15 | Plasma-F2-G10-1363-12h | 12 | 6.71 | |
| 16 | Plasma-F2-G11-1342-24h | 24 | 2.41 | 2.72 |
| 17 | Plasma-F2-G11-1340-24h | 24 | 2.47 | |
| 18 | Plasma-F2-G11-1365-24h | 24 | 3.28 | |
| 19 | Plasma-F2-G12-1349-36h | 36 | 1.36 | 3.67 |
| 20 | Plasma-F2-G12-1362-36h | 36 | 5.40 | |
| 21 | Plasma-F2-G12-1343-36h | 36 | 4.26 | |

TABLE 6

| Sample NO. | Sample ID (Formulation I) | Time (hour) | Conc. (μg/g tissue) | Ave. Conc. (μg/g tissue) |
|---|---|---|---|---|
| 1 | Liver-G13-Predose-1356 | 0 | 0.00 | 0.00 |
| 2 | Liver-G13-Predose-1354 | 0 | 0.00 | |
| 3 | Liver-G13-Predose-1366 | 0 | 0.00 | |
| 4 | Liver-F1-G1-1370-2h | 2 | 181.90 | 272.82 |
| 5 | Liver-F1-G1-1344-2h | 2 | 299.50 | |
| 6 | Liver-F1-G1-1373-2h | 2 | 337.05 | |
| 7 | Liver-F1-G2-1360-4h | 4 | 432.75 | 387.30 |
| 8 | Liver-F1-G2-1374-4h | 4 | 382.75 | |
| 9 | Liver-F1-G2-1376-4h | 4 | 346.40 | |
| 10 | Liver-F1-G3-1351-8h | 8 | 369.85 | 421.45 |
| 11 | Liver-F1-G3-1371-8h | 8 | 513.90 | |
| 12 | Liver-F1-G3-1359-8h | 8 | 380.60 | |
| 13 | Liver-F1-G4-1352-12h | 12 | 314.65 | 320.42 |
| 14 | Liver-F1-G4-1347-12h | 12 | 304.75 | |
| 15 | Liver-F1-G4-1377-12h | 12 | 341.85 | |
| 16 | Liver-F1-G5-1353-24h | 24 | 316.20 | 307.28 |
| 17 | Liver-F1-G5-1369-24h | 24 | 308.85 | |
| 18 | Liver-F1-G5-1378-24h | 24 | 296.80 | |
| 19 | Liver-F1-G6-1357-36h | 36 | 352.45 | 294.10 |
| 20 | Liver-F1-G6-1372-36h | 36 | 272.10 | |
| 21 | Liver-F1-G6-1367-36h | 36 | 257.75 | |

TABLE 7

| Sample NO. | Sample ID (Formulation II) | Time (hour) | Conc. (μg/g tissue) | Ave. Conc. (μg/g tissue) |
|---|---|---|---|---|
| 1 | Liver-G13-Predose-1356 | 0 | 0.00 | 0.00 |
| 2 | Liver-G13-Predose-1354 | 0 | 0.00 | |
| 3 | Liver-G13-Predose-1366 | 0 | 0.00 | |
| 4 | Liver-F2-G7-1345-2h | 2 | 214.55 | 177.90 |
| 5 | Liver-F2-G7-1368-2h | 2 | 158.30 | |
| 6 | Liver-F2-G7-1375-2h | 2 | 160.85 | |
| 7 | Liver-F2-G8-1358-4h | 4 | 245.15 | 234.52 |
| 8 | Liver-F2-G8-1361-4h | 4 | 222.30 | |
| 9 | Liver-F2-G8-1364-4h | 4 | 236.10 | |
| 10 | Liver-F2-G9-1346-8h | 8 | 243.85 | 213.22 |
| 11 | Liver-F2-G9-1350-8h | 8 | 211.55 | |
| 12 | Liver-F2-G9-1341-8h | 8 | 184.25 | |
| 13 | Liver-F2-G10-1348-12h | 12 | 195.00 | 206.22 |
| 14 | Liver-F2-G10-1355-12h | 12 | 196.90 | |
| 15 | Liver-F2-G10-1363-12h | 12 | 226.75 | |
| 16 | Liver-F2-G11-1342-24h | 24 | 244.70 | 205.17 |

TABLE 7-continued

| Sample NO. | Sample ID (Formulation II) | Time (hour) | Conc. (µg/g tissue) | Ave. Conc. (µg/g tissue) |
|---|---|---|---|---|
| 17 | Liver-F2-G11-1340-24h | 24 | 212.05 | |
| 18 | Liver-F2-G11-1365-24h | 24 | 158.75 | |
| 19 | Liver-F2-G12-1349-36h | 36 | 167.90 | 167.87 |
| 20 | Liver-F2-G12-1362-36h | 36 | 143.00 | |
| 21 | Liver-F2-G12-1343-36h | 36 | 192.70 | |

TABLE 8

| Sample NO. | Sample ID (Formulation I) | Time (hour) | Conc. (µg/g tissue) | Ave. Conc. (µg/g tissue) |
|---|---|---|---|---|
| 1 | Lung-G13-Predose-1356 | 0 | 0.00 | 0.00 |
| 2 | Lung-G13-Predose-1354 | 0 | 0.00 | |
| 3 | Lung-G13-Predose-1366 | 0 | 0.00 | |
| 4 | Lung-F1-G1-1370-2h | 2 | 139.35 | 103.68 |
| 5 | Lung-F1-G1-1344-2h | 2 | 105.80 | |
| 6 | Lung-F1-G1-1373-2h | 2 | 65.90 | |
| 7 | Lung-F1-G2-1360-4h | 4 | 22.50 | 32.55 |
| 8 | Lung-F1-G2-1374-4h | 4 | 35.35 | |
| 9 | Lung-F1-G2-1376-4h | 4 | 39.80 | |
| 10 | Lung-F1-G3-1351-8h | 8 | 30.05 | 32.47 |
| 11 | Lung-F1-G3-1371-8h | 8 | 34.65 | |
| 12 | Lung-F1-G3-1359-8h | 8 | 32.70 | |
| 13 | Lung-F1-G4-1352-12h | 12 | 12.85 | 24.80 |
| 14 | Lung-F1-G4-1347-12h | 12 | 30.05 | |
| 15 | Lung-F1-G4-1377-12h | 12 | 31.50 | |
| 16 | Lung-F1-G5-1353-24h | 24 | 19.05 | 21.30 |
| 17 | Lung-F1-G5-1369-24h | 24 | 22.20 | |
| 18 | Lung-F1-G5-1378-24h | 24 | 22.65 | |
| 19 | Lung-F1-G6-1357-36h | 36 | 54.75 | 33.08 |
| 20 | Lung-F1-G6-1372-36h | 36 | 22.75 | |
| 21 | Lung-F1-G6-1367-36h | 36 | 21.75 | |

TABLE 9

| Sample NO. | Sample ID (Formulation II) | Time (hour) | Conc. (µg/g tissue) | Ave. Conc. (µg/g tissue) |
|---|---|---|---|---|
| 1 | Lung-G13-Predose-1356 | 0 | 0.00 | 0.00 |
| 2 | Lung-G13-Predose-1354 | 0 | 0.00 | |
| 3 | Lung-G13-Predose-1366 | 0 | 0.00 | |
| 4 | Lung-F2-G7-1345-2h | 2 | 81.15 | 74.87 |
| 5 | Lung-F2-G7-1368-2h | 2 | 75.70 | |
| 6 | Lung-F2-G7-1375-2h | 2 | 67.75 | |
| 7 | Lung-F2-G8-1358-4h | 4 | 72.90 | 49.15 |
| 8 | Lung-F2-G8-1361-4h | 4 | 17.00 | |
| 9 | Lung-F2-G8-1364-4h | 4 | 57.55 | |
| 10 | Lung-F2-G9-1346-8h | 8 | 32.95 | 39.70 |
| 11 | Lung-F2-G9-1350-8h | 8 | 45.45 | |
| 12 | Lung-F2-G9-1341-8h | 8 | 40.70 | |
| 13 | Lung-F2-G10-1348-12h | 12 | 20.75 | 18.60 |
| 14 | Lung-F2-G10-1355-12h | 12 | 18.70 | |
| 15 | Lung-F2-G10-1363-12h | 12 | 16.35 | |
| 16 | Lung-F2-G11-1342-24h | 24 | 27.80 | 31.65 |
| 17 | Lung-F2-G11-1340-24h | 24 | 34.55 | |
| 18 | Lung-F2-G11-1365-24h | 24 | 32.60 | |
| 19 | Lung-F2-G12-1349-36h | 36 | 29.75 | 23.90 |
| 20 | Lung-F2-G12-1362-36h | 36 | 18.95 | |

TABLE 9-continued

| Sample NO. | Sample ID (Formulation II) | Time (hour) | Conc. (µg/g tissue) | Ave. Conc. (µg/g tissue) |
|---|---|---|---|---|
| 21 | Lung-F2-G12-1343-36h | 36 | 23.00 | |

TABLE 10

| Sample NO. | Sample ID (Formulation I) | Time (hour) | Conc. (µg/g tissue) | Ave. Conc. (µg/g tissue) |
|---|---|---|---|---|
| 1 | Spleen-G13-Predose-1356 | 0 | 0.00 | 0.00 |
| 2 | Spleen-G13-Predose-1354 | 0 | 0.00 | |
| 3 | Spleen-G13-Predose-1366 | 0 | 0.00 | |
| 4 | Spleen-F1-G1-1370-2h | 2 | 175.60 | 219.60 |
| 5 | Spleen-F1-G1-1344-2h | 2 | 298.60 | |
| 6 | Spleen-F1-G1-1373-2h | 2 | 184.60 | |
| 7 | Spleen-F1-G2-1374-4h | 4 | 411.60 | 386.97 |
| 8 | Spleen-F1-G2-1376-4h | 4 | 318.20 | |
| 9 | Spleen-F1-G2-1360-4h | 4 | 431.10 | |
| 10 | Spleen-F1-G3-1351-8h | 8 | 409.20 | 458.43 |
| 11 | Spleen-F1-G3-1371-8h | 8 | 552.70 | |
| 12 | Spleen-F1-G3-1359-8h | 8 | 413.40 | |
| 13 | Spleen-F1-G4-1352-12h | 12 | 473.40 | 424.03 |
| 14 | Spleen-F1-G4-1347-12h | 12 | 392.90 | |
| 15 | Spleen-F1-G4-1377-12h | 12 | 405.80 | |
| 16 | Spleen-F1-G5-1353-24h | 24 | 322.10 | 328.00 |
| 17 | Spleen-F1-G5-1369-24h | 24 | 363.70 | |
| 18 | Spleen-F1-G5-1378-24h | 24 | 298.20 | |
| 19 | Spleen-F1-G6-1357-36h | 36 | 227.80 | 322.83 |
| 20 | Spleen-F1-G6-1372-36h | 36 | 343.30 | |
| 21 | Spleen-F1-G6-1367-36h | 36 | 397.40 | |

TABLE 11

| Sample NO. | Sample ID (Formulation II) | Time (hour) | Conc. (µg/g tissue) | Ave. Conc. (µg/g tissue) |
|---|---|---|---|---|
| 1 | Spleen-G13-Predose-1356 | 0 | 0.00 | 0.00 |
| 2 | Spleen-G13-Predose-1354 | 0 | 0.00 | |
| 3 | Spleen-G13-Predose-1366 | 0 | 0.00 | |
| 4 | Spleen-F2-G7-1345-2h | 2 | 197.70 | 217.10 |
| 5 | Spleen-F2-G7-1368-2h | 2 | 240.90 | |
| 6 | Spleen-F2-G7-1375-2h | 2 | 212.70 | |
| 7 | Spleen-F2-G8-1358-4h | 4 | 273.60 | 254.30 |
| 8 | Spleen-F2-G8-1361-4h | 4 | 198.80 | |
| 9 | Spleen-F2-G8-1364-4h | 4 | 290.50 | |
| 10 | Spleen-F2-G9-1346-8h | 8 | 105.40 | 203.73 |
| 11 | Spleen-F2-G9-1350-8h | 8 | 362.90 | |
| 12 | Spleen-F2-G9-1341-8h | 8 | 142.90 | |
| 13 | Spleen-F2-G10-1348-12h | 12 | 131.10 | 214.00 |
| 14 | Spleen-F2-G10-1355-12h | 12 | 236.90 | |
| 15 | Spleen-F2-G10-1363-12h | 12 | 274.00 | |
| 16 | Spleen-F2-G11-1342-24h | 24 | 117.50 | 256.20 |
| 17 | Spleen-F2-G11-1340-24h | 24 | 303.10 | |
| 18 | Spleen-F2-G11-1365-24h | 24 | 348.00 | |
| 19 | Spleen-F2-G12-1349-36h | 36 | 225.00 | 209.87 |
| 20 | Spleen-F2-G12-1362-36h | 36 | 326.80 | |
| 21 | Spleen-F2-G12-1343-36h | 36 | 77.80 | |

TABLE 12

| Sample NO. | Sample ID (Formulation I) | Time (hour) | Conc. (μg/g tissue) | Ave. Conc. (μg/g tissue) |
|---|---|---|---|---|
| 1 | Pancreas-G13-Predose-1356 | 0 | 0.00 | 0.00 |
| 2 | Pancreas-G13-Predose-1354 | 0 | 0.00 | |
| 3 | Pancreas-G13-Predose-1366 | 0 | 0.00 | |
| 4 | Pancreas-F1-G1-1370-2h | 2 | 8.00 | 6.47 |
| 5 | Pancreas-F1-G1-1344-2h | 2 | 4.75 | |
| 6 | Pancreas-F1-G1-1373-2h | 2 | 6.65 | |
| 7 | Pancreas-F1-G2-1360-4h | 4 | 0.00 | 0.00 |
| 8 | Pancreas-F1-G2-1374-4h | 4 | 0.00 | |
| 9 | Pancreas-F1-G2-1376-4h | 4 | 0.00 | |
| 10 | Pancreas-F1-G3-1351-8h | 8 | 1.75 | 0.68 |
| 11 | Pancreas-F1-G3-1371-8h | 8 | 0.05 | |
| 12 | Pancreas-F1-G3-1359-8h | 8 | 0.25 | |
| 13 | Pancreas-F1-G4-1352-12h | 12 | 0.10 | 0.03 |
| 14 | Pancreas-F1-G4-1347-12h | 12 | 0.00 | |
| 15 | Pancreas-F1-G4-1377-12h | 12 | 0.00 | |
| 16 | Pancreas-F1-G5-1353-24h | 24 | 0.00 | 0.77 |
| 17 | Pancreas-F1-G5-1369-24h | 24 | 0.65 | |
| 18 | Pancreas-F1-G5-1378-24h | 24 | 1.65 | |
| 19 | Pancreas-F1-G6-1357-36h | 36 | 0.00 | 0.48 |
| 20 | Pancreas-F1-G6-1372-36h | 36 | 1.45 | |
| 21 | Pancreas-F1-G6-1367-36h | 36 | 0.00 | |

TABLE 13

| Sample NO. | Sample ID (Formulation II) | Time (hour) | Conc. (μg/g tissue) | Ave. Conc. (μg/g tissue) |
|---|---|---|---|---|
| 1 | Pancreas-G13-Predose-1356 | 0 | 0.00 | 0.00 |
| 2 | Pancreas-G13-Predose-1354 | 0 | 0.00 | |
| 3 | Pancreas-G13-Predose-1366 | 0 | 0.00 | |
| 4 | Pancreas-F2-G7-1345-2h | 2 | 6.75 | 4.78 |
| 5 | Pancreas-F2-G7-1368-2h | 2 | 3.00 | |
| 6 | Pancreas-F2-G7-1375-2h | 2 | 4.60 | |
| 7 | Pancreas-F2-G8-1358-4h | 4 | 1.25 | 2.98 |
| 8 | Pancreas-F2-G8-1361-4h | 4 | 1.75 | |
| 9 | Pancreas-F2-G8-1364-4h | 4 | 5.95 | |
| 10 | Pancreas-F2-G9-1346-8h | 8 | 0.60 | 1.45 |
| 11 | Pancreas-F2-G9-1350-8h | 8 | 3.75 | |
| 12 | Pancreas-F2-G9-1341-8h | 8 | 0.00 | |
| 13 | Pancreas-F2-G10-1348-12h | 12 | 0.00 | 0.88 |
| 14 | Pancreas-F2-G10-1355-12h | 12 | 0.00 | |
| 15 | Pancreas-F2-G10-1363-12h | 12 | 2.65 | |
| 16 | Pancreas-F2-G11-1342-24h | 24 | 7.15 | 3.43 |
| 17 | Pancreas-F2-G11-1340-24h | 24 | 3.15 | |
| 18 | Pancreas-F2-G11-1365-24h | 24 | 0.00 | |
| 19 | Pancreas-F2-G12-1349-36h | 36 | 0.00 | 0.12 |
| 20 | Pancreas-F2-G12-1362-36h | 36 | 0.35 | |
| 21 | Pancreas-F2-G12-1343-36h | 36 | 0.00 | |

TABLE 14

| Sample NO. | Sample ID (Formulation I) | Time (hour) | Ave. Conc. (μg/g tissue) |
|---|---|---|---|
| 1 | Brain-G13-Predose-1356 | 0 | 0.00 |
| 2 | Brain-G13-Predose-1354 | 0 | |
| 3 | Brain-G13-Predose-1366 | 0 | |
| 4 | Brain-F1-Group 4-12h | 12 | 1.45 |
| 5 | Brain-F1-Group 5-24h | 24 | 8.65 |
| 6 | Brain-F1-Group 6-36h | 36 | 4.45 |

TABLE 15

| Sample NO. | Sample ID (Formulation II) | Time (hour) | Ave. Conc. (μg/g tissue) |
|---|---|---|---|
| 1 | Brain-G13-Predose-1356 | 0 | 0.00 |
| 2 | Brain-G13-Predose-1354 | 0 | |
| 3 | Broin-G13-Predose-1366 | 0 | |
| 4 | Brain-F2-Group 10-12h | 12 | 8.35 |
| 5 | Brain-F2-Group 11-24h | 24 | 3.90 |
| 6 | Brain-F2-Group 12-36h | 36 | 5.40 |

The results of this study demonstrate a greater accumulation of Coenzyme Q10 in the liver and spleen for Formulation 1, which does not comprise poloxamer, as compared to Formulation 2, which comprises poloxamer. These results indicate a greater clearance of Coenzyme Q10 from the blood by the liver and spleen in the absence of poloxamer, and less clearance of Coenzyme Q10 from the blood by these organs in the presence of poloxamer, and are consistent with the role of poloxamer in the Coenzyme Q10 formulations as an opsonization reducer.

Example 12

Effect of CoQ10 IV Formulation on Liver Cancer: The ability of a Coenzyme Q10 formulation of the present invention to inhibit proliferation of liver tumor cells was examined in an animal model. Twenty-four Fischer 344 rats were injected intraperitoneally with the liver clone of a malignant chloroma Rats were then randomized into groups of 6 rats each. Group 1 served as a control, treated with 0.5 mL of phosphate buffered saline on Monday, Wednesday and Friday for three (3) weeks. Group II received a sterile nanodispersion by IP injection of 20 mg of Coenzyme Q10. This formulation contained, by weight, 4% Coenzyme Q10, 3% DMPC, and 1.5% poloxamer 188 in PBS. The formulation was administered by IP injection in a volume of 0.5 mL on Monday, Wednesday and Friday for three (3) weeks. Group III received 35 mg/kg of cyclophosphamide once. Group IV received 20 mg of the 4:3:1.5 CoQ10 formulation in 0.5 mL on Monday, Wednesday and Friday for three (3) weeks. In addition, they received 35 mg/kg of cyclophosphamide once.

All animals in the control group were dead of liver metastasis by day 20 post-transplant. In the group treated with the sterile 4:3:1.5 CoQ10 N nanodispersion formulation (Group II), 50% of rats survived and remained disease-free. The other 50% survived 38 days or more. In the group treated with chemotherapy alone (Group III), 1 rat remained disease-free while the other three rats survived up to day 34 and hence. In the group that received the 4:3:1.5 CoQ10 IV formulation and the chemotherapy (Group N), 5 of 6 rats remained disease free and one survived up to day 38.

The 4:3:1.5 CoQ10 IV formulation demonstrated a better safety profile. No side effects were observed in the animals receiving CoQ10 as evidenced by weight gain and behavior.

The 4:3:1.5 CoQ10 N formulation alone showed more significant efficacy as a single agent than chemotherapy alone. Moreover, where the 4:3:1.5 CoQ10 N formulation was used in combination with chemotherapy, the effect on survival was synergistic, yielding 83% survival. FIG. 35 depicts these results.

In conclusion, the CoQ10 formulation demonstrated improved safety over chemotherapy, significant therapeutic activity in treating liver cancer that was more effective than chemotherapy alone, and demonstrated synergistic therapeutic activity with chemotherapy in treating liver cancer.

Example 13

Efficacy of Daily Dosing of CoQ10 IV Formulation on Liver Tumors: A group (n=30/group) of seven-day-old Fischer 344 rats were injected intraperitoneally with the liver clone of a malignant chloroma. Beginning 6 hours later, the animals were dosed daily via intraperitoneal injection for 20 days as follows: untreated, saline control, vehicle control (DMPC and Poloxamer 188 in PBS), or the 4:3:1.5 CoQ10 IV formulation at 0.5, 2, 5, 10, 25 and 50 mg/kg/day. Mortality was as follows: 30/30 in the untreated and saline controls (by Day 29); 29/30 at 0.5 mg/kg/day (by Day 29); 27 or 28/30 at 2 mg/kg/day (by Day 44); 24/30 at 5 mg/kg/day (by Day 55); 21/30 at 10 mg/kg/day (by Day 46); 15/30 at 25 mg/kg/day (by Day 46); and 13/30 at 50 mg/kg/day (by Day 53). In addition to a dose-related increase in survival, the 4:3:1.5 CoQ10 IV formulation extended the day at which mortality began (i.e., approximately Day 15 for the untreated and saline controls as compared to approximately Days 25, 38, 36, 40, and 45 at 2, 5, 10, 25, and 50 mg/kg/dose, respectively) and decreased the slope of the mortality curve.

Example 14

Effect of CoQ10 IV Formulation on Lung Tumors: The ability of a Coenzyme Q10 formulation of the invention to inhibit proliferation of lung tumor cells was examined in an animal model. Twenty-four Fischer 344 rats were injected intraperitoneally with the lung clone of a malignant chloroma. The rats were then randomized into groups of 6 rats each. Group 1 served as a control, treated with 0.5 mL of phosphate buffered saline (PBS) on Monday, Wednesday and Friday for three (3) weeks. Group H received 20 mg of the 4:3:1.5 CoQ10 IV formulation, that contained in a sterile nanodispersion at a concentration of 40 mg/mL coenzyme Q10 in the 4:3:1.5 formulation. The formulation was administered by IP injection in a volume of 0.5 mL on Monday, Wednesday, and Friday for three (3) weeks. Group III received 35 mg/kg cyclophosphamide by IP injection once. Group IV received 20 mg of the 4:3:1.5 CoQ10 IV formulation, via the same formulation as that used for Group II and was injected IP in a volume of 0.5 mL on Monday, Wednesday and Friday for three (3) weeks and, in addition, received 35 mg/kg of cyclophosphamide once.

All animals in the control group were dead due to lung metastasis by day 21 post-transplant. In the group treated with the 4:3:1.5 CoQ10 IV formulation (Group II), 50% of rats survived and remained disease-free. The other 50% survived 40 days or more. In the group treated with chemotherapy alone (Group III), 1 rat remained disease-free while 4 rats survived up to day 35. One animal died within the control range and was therefore considered a non-responder. In the group that received the combination treatment of the 4:3:1.5 CoQ10 IV formulation and chemotherapy, 6 out of 6 rats remained disease free.

The 4:3:1.5 CoQ10 IV formulation demonstrated a better safety profile. No side effects were observed in the animals receiving CoQ10 as evidenced by weight gain and behavior. The 4:3:1.5 CoQ10 IV formulation alone showed significant and greater efficacy as a single agent than chemotherapy alone. Where the 4:3:1.5 CoQ10 IV formulation was used in combination with chemotherapy, the therapeutic activity was synergistic, yielding 100% survival. FIG. 36 depicts these results.

In conclusion, the 4:3:1.5 CoQ10 formulation demonstrated improved safety over chemotherapy, significant and greater therapeutic activity in treating lung cancer than chemotherapy alone, and demonstrated synergistic therapeutic activity with chemotherapy in treating lung cancer.

Example 15

Induction of Apoptosis in Cells In Vitro by CoQ10 IV Formulation: Three apoptotic assays, (1) oxygen consumption rate (OCR), (2) caspase 3 activity assay, and (3) Western Blotting analysis for Caspase 3 were used to validate the effects of the CoQ10 IV formulation on cancer cells.

For the oxygen consumption rate assay, the oxygen consumption rates in the cell lines was determined using the Seahorse apparatus. The caspase 3 activity was determined using a colorimetric method using a commercially available kit according to manufacturer's instructions. The increase in the expression of Caspase 3 as a measure of apoptosis was determined by western blotting analysis using an antibody specific for detection of Caspase 3 protein.

The effects of two CoQ10 IV formulations were examined using OCR as a readout. The first formulation (no poloxamer) included 4% CoQ10; 3% DMPC; and 93% water. The second formulation (with poloxamer) included 4% CoQ10; 3% DMPC; 1.5% Poloxamer P188; and 91.5% water. The effects of the two formulations on OCR were evaluated 6 hours after the start of the treatment against an untreated "media only" control for each cell line. A final concentration of 50 μM and of 100 μM of CoQ10 was used for both formulations.

As depicted in FIGS. 25-28, the results of this study demonstrate that highly cancerous or metastatic cell lines are particularly sensitive to 4:3:1.5 CoQ10 IV formulation treatment. Most of the cancer cell lines tested had OCR values that were sensitive to the 4:3:1.5 CoQ10 IV formulation treatment. CoQ10 IV Formulation reduced OCR in HepG2 cells (50 and 100 uM), MCF-7 cells (100 uM), PC-3 cells (50 and 100 uM), and PaCa2 cells (50 and 100 uM). The non-metastatic cell line LnCap and normal cell lines such as HDFa were not sensitive to the CoQ10 IV formulations.

Caspase 3 levels were determined in various cell lines following treatment with the same two CoQ10 N formulations as used above (the first formulation included 4% CoQ10; 3% DMPC; and 93% water, and the second formulation included 4% CoQ10; 3% DMPC; 1.5% Poloxamer P188; and 91.5% water). Specifically, PC-3, HepG2, MCF-7, HDFa and MIAPACA2 cells were treated with the CoQ10 IV formulation and harvested after 24 hours of treatment. The whole cell pellets of these cells were used for Western Blots. Sample volumes equivalent to 10 μg of protein were prepared with Lamelli Loading Dye (LDS) and water and run on a 4-12% Bis-Tris Novel NuPAGE gel on two 10 lane gels (15 μL loaded per lane) as detailed below.

For gel 1 (FIGS. 29 and 30), lane 1 contains a sample from MCF-7 cells treated with media only, lane 2 contains a sample from MCF-7 cells treated with the CoQ10 formulation without poloxamer, lane 3 contains sample from MCF-7 cells treated with the CoQ10 formulation comprising poloxamer, lane 4 contains sample from HDFa cells treated with media only, lane 5 contains sample from HDFa cells treated with the CoQ10 formulation without poloxamer, lane 6 contains sample from HDFa cells treated with the CoQ10 formulation comprising poloxamer, lane 7 contains sample from Paca2 cells treated with media only, lane 8 contains sample from Paca2 cells treated with the CoQ10 formulation without poloxamer, lane 9 contains sample from Paca2 cells treated with the CoQ10 formulation comprising poloxamer, and lane 10 contains a standard protein size marker.

For gel 2 (FIGS. 31 and 32), lane 1 contains a protein marker, lane 2 contains a sample from PC3 cells treated with media only, lane 3 contains a sample from PC3 cells treated with the CoQ10 formulation without poloxamer, lane 4 contains sample from PC3 cells treated with the CoQ10 formulation comprising poloxamer, lane 5 contains sample from HepG2 cells treated with media only, lane 6 contains sample from HepG2 cells treated with the CoQ10 formulation without poloxamer, lane 7 contains sample from HepG2 cells treated with the CoQ10 formulation comprising poloxamer, lane 8 is blank and lanes 9 and 10 both contain protein size markers.

The gels were ran for 50 minutes using 1×MOPS buffer using a NOVEX Xcell Surelock system with the voltage at 200 V. The gels were then transferred for 1 hour using a NOVEX Xcell Surelock wet transfer protocol at a voltage of 35 V. The blots were stained for 5 hours with Simply Blue Safestain from Invitrogen (LC6065).

A Western blot analysis was performed to determine the level of Caspase 3 and Beta Actin in the above samples. For the detection of caspase 3, after transfer, each blot was placed in between 2 Whatman Filter papers and dried for 15-20 minutes. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the primary antibody for Caspase 3 (Santacruz sc7272) in 5% BSA (at 1:200 dilutions) by incubation overnight at 4° C. with shaking.

After overnight incubation with primary antibody for Caspase 3, the blots were washed 3 times with TBS-T (1×-15'; 2×5' each) and probed with the secondary antibody (antimouse; 1:10,000 dilution) for 1 hour while shaking at room temperature. The blots were washed 3 times with TBS-T (1×-15'; 2×5' each), incubated with ECF reagent for 5 minutes and then each blot scanned with 5100 Fuji Laser scanner at 25 uM resolution, 16 bit, green laser, at 400V and at 500 V.

To detect actin in the samples, the Caspase 3 blots were stripped by incubating for 30 minutes with methanol, followed by two 10 minute washes with TBS-T, then 30 minutes of incubation with stripping buffer at 50° C., and followed by two washes with 100 mL or more of TBS-T for 30 minutes each. The blots were scanned in a laser scanner to confirm complete stripping. The blots were activated with methanol for 5 seconds, washed with water for 5 minutes, and TBST for 15 minutes. The blots were blocked for 1 hour with 5% blocking reagent in TBS-T at room temperature and then washed 3 times with TBS-T (1×-15'; 2×5' each) and probed with the antibody for Actin in 5% BSA (Sigma #A5316 clone AC 74) at 1:5000 dilutions) for 1 hour at room temperature with shaking.

After incubation with primary antibody for Actin, the membranes were washed 3 times with TBS-T (1×-15'; 2×5' each) and probed with the secondary antibody (antimouse; 1:10,000 dilution) for 1 hour while shaking at room temperature. The blots were washed 3 times with TBS-T (1×-15'; 2×5' each), incubated with ECF reagent for 5 minutes and then each blot scanned with 5100 Fuji Laser scanner at 25 uM resolution, 16 bit, green laser, at 400V and at 500V.

The final Western blots for gel 1 are shown in FIG. 29 (Caspase 3) and FIG. 26 (Actin), and for gel 2 are shown in FIG. 31 (Caspase 3) and FIG. 32 (Actin). The levels of Caspase 3 were quantitated, normalized to Actin and the resulting data is presented in FIGS. 33-36.

The results of this study show that an increase in normalized Caspase 3 protein levels was observed in PC3 (FIG. 33) and MiaPACA2 (FIG. 34) cells treated with the CoQ10 formulation comprising poloxamer 24 hours post treatment. The level of unnormalized Caspase 3 protein in HepG2 cells 24 hours after treatment is depicted in FIG. 35, since Actin was not obtained for these samples. The increase in the HepG2 lower band is very similar to that observed in the PACA2 (FIG. 34) and PC-3 (FIG. 33) cells with the upper band. Only the lower band was detected in the HDFa cells, and the intensity of this band decreased with CoQ10 treatment (FIG. 36), similar to the pattern seen with the upper band in HepG2 (FIG. 35). In summary, an increase in Caspase 3 protein levels was observed in at least both PACA2 and PC-3 cells, and likely also in HepG2 cells, following treatment with CoQ10, indicating induction of apoptosis in these cells. In normal cells, no induction of apoptosis was observed following exposure to the CoQ10 IV formulation.

Example 16

Effect of CoQ10 IV Formulation on Pancreatic Carcinoma Cell Line: MiaPACA2, a pancreatic cell line was employed on NSG mice. Mice were anesthetized in a sterile environment where they had been housed. Once animals reached surgical-plane anesthesia, mice were laid down, and the abdominal area was palpated. The pancreas was located behind the stomach, between the spleen, and the stomach, both of which are palpable organs. Thereafter, 10×1065 cells were injected in the pancreas by gently manipulating the animal to reach the area behind the stomach. All of these procedures were performed under sterile conditions in a biosafety cabinet, and the animals were housed under strict sterile conditions as well to avoid opportunistic infections. After injection of cells, animals were closely monitored daily. Animals were then randomized into 8 groups receiving a different dose of the CoQ10 N formulation. Group one remained untreated; group 2 received saline only; group 3 received excipient control; group 4 received 0.5 mg/kg of the 4:3:1.5 CoQ10 IV formulation as described herein; group 5 received 5 mg/kg of the 4:3:1.5 CoQ10 N formulation as described herein; group 6 received 10 mg/kg of the 4:3:1.5 CoQ10 N formulation as described herein; group 7 received 25 mg/kg of the 4:3:1.5 CoQ10 IV formulation as described herein and group 8 received 50 mg/kg of the 4:3:1.5 CoQ10 IV formulation as described herein. The formulation was administered intravenously via tail veins with dosing every other day three times per week for up to 28 days. The summary of results are depicted in the following graphs (FIGS. 49-56).

All animals in the untreated and saline treated control groups were dead by Day 21. Excipient-treated animals died by Day 36. A dose-related improvement in mortality was noted following treatment with CoQ10 N Formulation. Doses of 0.5, 5 and 10 mg/kg/dose produced complete mortality by Days 31, 41 and 56 respectively. At 25 and 50 mg/kg/dose, complete mortality was not observed with 3 and 11 animals surviving. Survival was significantly increased at 5 mg/kg/dose and above and health was improved at these doses. In addition, at 25 and 50 mg/kg/dose, 3 and 4 of the surviving animals had tumors, respectively. Co-administration of CoQ10 IV Formulation at 50 mg/kg with doxorubicin resulted in a significant improvement in survival (25 of 30 animals survived at 60 days as compared to 0 of 30 survivors in the doxorubicin group) as well as the number of animals free of tumors (25/30 with CoQ10 N Formulation).

Example 17

Combination Therapy With CoQ10 IV Formulation and Chemotherapy Adjuvant Doxorubicin, a powerful chemotherapeutic, is lethal when administered intraperitoneally, by itself, in rodents. CoQ10 IV Formulation was administered in combination with doxorubicin. As can be seen in the graphs presented in FIGS. 45 and 46, when doxorubicin is administered in combination with the 4:3:1.5 CoQ10 IV formulation, survival of rodents significantly increased over doxorubicin when administered alone.

As can be seen in FIG. 58, COQ10 IV was not only additive, but also protective against the doxorubicin toxicity. Mortality rates were highly statistically significantly low, with only a few deaths starting on day 41. Nevertheless, 25 out of 30 animals remained alive and cancer-free by day 60, with six animals exhibiting small tumors at day sixty. These findings demonstrate that the administered Coenzyme Q10 formulation exerted a potent adjuvant effect.

Example 18

Effect of CoQ10 on Breast Cancer: In another in vitro study, the effect of CoQ10 (50 and 100 μM) on various members of the Bcl-2 family (bcl-2, bcl-xl, bid, bad, bak, mcl-1, bim, and bax), p53, and caspases 4, 8, 12 in two breast cancer cell lines, MCF-7 and Sk-BR3, was evaluated. The Bcl-2 protein family has been implicated as the major contributing factor to conferral of resistance to cancer therapy. CoQ10 upregulated protein expression of pro-apoptotic members and BH3 subfamily members (bid, bad, bax, bim, and bak), significantly decreased levels of the anti-apoptotic members (bcl-xl, mcl-1, and bcl-2), and increased apoptosis (measured by activation of caspase 3, 6 and 9) restoring the apoptotic potential in breast cancer without presenting any adverse effects to normal breast tissue.

Example 19

Absorption/Pharmacokinetics of CoQ10 IV Formulation: The pharmacokinetics of the CoQ10 IV Formulation was determined after intravenous administration of 100 mg/kg of one of two CoQ10 IV Formulations (Tables 16-18). Formulation 1 did not contain any Poloxamer 188, but Formulation 2 did contain Poloxamer 188. There were 18 female mice in each formulation group, and three mice were sacrificed for sampling at 2, 4, 8, 12, 24 and 36 hr post-dose. There was no apparent difference in the plasma profiles for the two formulations. A $t_{1/2}$ value of approximately 38 hr was determined. There were no measurable plasma concentrations of CoQ10 IV Formulation in a group of three untreated mice.

The pharmacokinetic parameters for CoQ10 IV Formulation in Sprague Dawley rats were determined in the toxicokinetic evaluations for two toxicity studies. Charles River Study Number 20000711 was a rising-dose study with a subsequent 7-day treatment phase. For the toxicokinetic evaluation in the rising-dose phase (Tables-18), groups of nine male and nine female rats received 100, 250, 750 and 1,000 mg/kg CoQ10 IV Formulation as a single bolus intravenous injection. For the multiple dose phase (Table 19), groups of nine males and nine females received 250 or 500 mg/kg CoQ10 IV Formulation as bolus intravenous injections for every three days for seven days. For the rising-dose phase and on Day 7 of the multiple-dose phase, samples were collected from subgroups of three males and three females pre-dose, at 5 and 15 minutes, and at 1, 4, and 24 hr post-dose. Many of the concentrations were above 1 mg/mL for animals receiving 100, 250 or 500 mg/kg, and quite a few are above 10 mg/mL for animals receiving 750 or 1,000 mg/kg, with many of the remaining samples being above 1 mg/mL. The plasma profiles were not typical of intravenous administration. Although $C_{max}$ and $AUC_{0-t}$ generally increased with dose, there were exceptions, and there was no clear linear dose-dependency, which is expected with intravenous administration. Estimated values of $t_{1/2}$ ranged from 0.8 to 10.0 hr, and there was no apparent dependence on gender or dose.

TABLE 16

Pharmacokinetics After a Single Dose
Location in CTD m4-2-2-2
Study No. EB08-014-12a

| | Species | | |
|---|---|---|---|
| | Mouse | Mouse | Mouse |
| Gender (M/F)/Number of animals | 18 F | 18 F | 3 F |
| Feeding condition | NA | NA | NA |
| Vehicle/Formulation | Formulation 1, without poloxamer | Formulation 2, with poloxomer | No treatment |
| Method of Administration | IV | IV | — |
| Dose (mg/kg) | 100 | 100 | — |
| Sample (e.g., whole blood, plasma, serum) | Plasma | Plasma | Plasma |
| Analyte | 31510 | 31510 | 31510 |
| Assay | LC/MS/MS | LC/MS/MS | LC/MS/MS |
| PK parameters: | | | |
| $C_0$ (μg/mL) (rough estimate for $C_{max}$) | 4,035 | 2,265 | — |
| $AUC_{0-4}$ (μg · hr/mL) (rough estimate) | 5,418 | 3,503 | — |
| $C_2$ (μg/mL) | 503 | 423 | BLQ |
| $AUC_{2-36}$ (μg·hr/mL) | 880 | 815 | — |
| $t_{1/2}$ (hr) | 38.1 | no reliable value | — |

Additional Information: The first sampling time was 2 hr post-dose. The values for $C_0$ and $AUC_{0-t}$ are based on >75% back extrapolation and are considered rough estimates only. The values for $C_2$ and $AUC_{2-36}$ are based on samples taken from 2 hr to 36 hr and do not have extrapolated components.

TABLE 17

Pharmacokinetics After a Single Dose (cont'd)

| Location in CTD | m4-2-2-2 | | | | |
|---|---|---|---|---|---|
| Study No. (Report No.) | 20000711 | | | | |
| Species | Rat | Rat | Rat | Rat | Rat |
| Gender (M/F)/No. of animals | 9 M, 9 F | 9 M, 0 F | 9 M, 0 F | 9 M, 9 F | 9 M, 9 F |
| Feeding condition | Fed | Fed | Fed | Fed | Fed |
| Vehicle/Formulation | IV Formulation | IV Formulation | IV Formulation | IV Formulation | IV Formulation |
| Method of Administration | IV bolus | IV bolus | IV bolus | IV bolus | IV bolus |

TABLE 17-continued

Pharmacokinetics After a Single Dose (cont'd)

| Location in CTD | | m4-2-2-2 | | | | |
|---|---|---|---|---|---|---|
| Study No. (Report No.) | | 20000711 | | | | |
| Species | | Rat | Rat | Rat | Rat | Rat |
| Dose (mg/kg) | | 100 | 250 | 750 | 750 | 1.000 |
| Sample Type | | Plasma | Plasma | Plasma | Plasma | Plasma |
| Analyte | | 31510 | 31510 | 31510 | 31510 | 31510 |
| Assay | | LC/MS/MS | LC/MS/MS | LC/MS/MS | LC/MS/MS | LC/MS/MS |
| PK parameters: | | | | | | |
| $C_{max}$ (µg/mL) | M | 1.933 | 1.661 | 9.953 | 13.000 | 18.267 |
| | F | 1.907 | 4.130 | 10.820 | 8.479 | 15.800 |
| $T_{max}$ (hr) | M | 0.083 | 0.083 | 1 | 0.25 | 0.25 |
| | F | 0.25 | 1 | 0.083 | 0.25 | 1 |
| $AUC_{0-t}$ (µg·hr/mL) | M | 3.098 | 2.077 | 36.850 | 57.248 | 29.788 |
| | F | 3.908 | 9.747 | 79.541 | 49.860 | 83.812 |
| $t_{1/2}$ (hr) | M | 1.19 | — | 2.40 | 10.0 | 0.806 |
| | F | 0.940 | — | 2.35 | 3.90 | 2.72 |

TABLE 18

Pharmacokinetics After a Single Dose (cont'd)
Location in CTD m4-2-2-2
Study No. (Report No.) 20000713

| | | Species | |
|---|---|---|---|
| | | Dog | Dog |
| Gender (M/F)/No. of animals | | 1 M, 1 F | 2 M, 2F |
| Feeding condition | | Fed | Fed |
| Vehicle/Formulation | | IV Formulation | IV Formulation |
| Method of Administration | | IV bolus | IV bolus |
| Dose (mg/kg) | | 125 | 250 |
| Sample Type | | Plasma | Plasma |
| Analyte | | 31510 | 31510 |
| Assay | | LC/MS/MS | LC/MS/MS |
| PK parameters: | | | |
| $C_{max}$ (µg/mL) | M | 2,450 | 4,110 |
| | F | 2,380 | 4,120 |
| $T_{max}$ (hr) | M | 0.25 | 0.083 |
| | F | 0.25 | 0.25 |
| $AUC_{0-4}$ (µg·hr/mL) | M | 19,231 | 36,892 |
| | F | 6,787 | 38,992 |
| $t_{1/2}$ (hr) | M | 4.60 | 8.16 |
| | F | 2.07 | 5.94 |

TABLE 19

Pharmacokinetics After Repeated Doses (7 Days or Less)

| Location in CTD | | m4-2-2-2 | | m4-2-2-2 | |
|---|---|---|---|---|---|
| Study No. | | 20000711 | | 20000713 | |
| Species | | Rat | Rat | Dog | Dog |
| Gender (M/F)/No. of animals | | 9 M, 9 F | 9 M, 9 F | 2 M | 2 F |
| Feeding condition | | Fed | Fed | Fed | Fed |
| Vehicle/Formulation | | IV formulation | IV formulation | IV formulation | IV formulation |
| Method of Administration | | IV bolus | IV bolus | IV bolus | IV bolus |
| Dose (mg/kg) | | 250 | 500 | 125 | 125 |
| Duration (days) | | QD for 7 days | QD for 7 days | Days 1, 3, 5, 7 | Days 1, 3, 5 |
| Sample Type | | Plasma | Plasma | Plasma | Plasma |
| Assay | | LC/MS/MS | LC/MS/MS | LC/MS/MS | LC/MS/MS |
| PK parameters | | Day 7 | Day 7 | Day 1 | Day 7 | Day 1 | Day 5 |
| $C_{max}$ (µg/mL) | M | 4,703 | 6,970 | 2,225 | 2,320 | | |
| | F | 4,533 | 7,310 | | | 2,355 | 2,275 |
| $T_{max}$ (hr) | M | 1 | 1 | 0.083 | 0.25 | | |
| | F | 0.25 | 0.25 | | | 0.167 | 0.167 |
| $AUC_{0-t}$ (µg·hr/mL) | M | 11,906 | 43,955 | 13,139 | 12,726 | | |
| | F | 9,666 | 10,837 | | | 13,739 | 12,757 |
| $t_{1/2}$ (hr) | M | — | 2.53 | 3.68 | 4.24 | | |
| | F | 2.00 | — | | | 3.73 | 4.87 |

Additional Information: The dose for male dogs on Day 5 was indeterminate. All other doses are as noted.

In the second rat toxicity study, Charles River Study Number 20000328, CoQ10 was administered as short intravenous infusions at the rate of 1.0 mL/min three times a week for four weeks. For the toxicokinetic evaluation, three groups of nine male and nine females received 62.5, 125, and 250 mg/kg CoQ10 IV Formulation (Table 20). On Days 1 and 26, samples were collected from subgroups of three males and three females at 5 and 15 minutes, and at 1, 4, 24 and 48 hr post-dose. The peak systemic exposure to CoQ10 IV Formulation, as measured by $C_{max}$, and the total exposure, as measured by $AUC_{0-t}$, increased with increasing dose. The increases in $C_{max}$ were close to linear with dose, and the increases in $AUC_{0-t}$ were slightly greater than dose proportional. Between Day 1 and Day 26, $C_{max}$ and $AUC_{0-t}$ decreased. $T_{max}$ occurred at 0.083 or 0.25 hr, the first two sampling times. There may have been small dose-dependent increases in $t_{1/2}$. There was no apparent gender difference.

tered as short intravenous infusions at the rate of 5.0 mL/min three times a week for four weeks. Four groups of five male and five female dogs received vehicle, 31.25, 62.5 or 125 mg/kg CoQ10 IV Formulation (Table 20). Plasma samples were collected pre-dose, at 5, 15, and 30 minutes, and at 1, 2, 4, 8, and 24 hr post-dose on Days 1 and 26. $C_{max}$, $AUC_{0-t}$, and $AUC_{0-\infty}$ increased with dose for both sexes on both sampling days. The increases in $C_{max}$ were greater than proportional to dose on Day 1, but close to dose-proportional on Day 26. The increases in $AUC_{0-t}$ were greater than proportional to dose on both Day 1 and Day 26, however, the magnitude of the nonlinearity was less on Day 26. Between Day 1 and Day 26, there were slight or small changes in mean $C_{max}$ and $AUC_{0-t}$ for the low- and mid-dose groups indicating little change in exposure for the two lower dose groups. For the high-dose group, there decreases in both mean $C_{max}$ and $AUC_{0-t}$ between Day 1 and Day 26. With the

TABLE 20

Pharmacokinetics After Repeated Doses (4 Weeks)

| Location in CTD | | m4-2-2-2 | | | | | |
|---|---|---|---|---|---|---|---|
| Study No. | | 20000328 | | | | | |
| Species | | Rat | | Rat | | Rat | |
| Gender (M/F)/No. of animals | | 9 M, 9 F | | 9 M, 9 F | | 9 M, 9 F | |
| Feeding condition | | Fed | | Fed | | Fed | |
| Vehicle/Formulation | | IV formulation | | IV formulation | | IV formulation | |
| Method of Administration | | IV short infusion | | IV short infusion | | IV short infusion | |
| Dose (mg/kg) | | 62.5 | | 125 | | 250 | |
| Duration (days) | | 3 times weekly for 4 weeks | | 3 times weekly for 4 weeks | | 3 times weekly for 4 weeks | |
| Sample Type | | Plasma | | Plasma | | Plasma | |
| Assay | | LC/MS/MS | | LC/MS/MS | | LC/MS/MS | |
| PK parameters | | Day 1 | Day 26 | Day 1 | Day 26 | Day 1 | Day 26 |
| $C_{max}$ (µg/mL) | M | 1,663 | 1,052 | 3,197 | 2,660 | 6,397 | 4,257 |
| | F | 1,670 | 891 | 2,970 | 2,400 | 6,900 | 4,167 |
| $T_{max}$ (hr) | M | 0.083 | 0.083 | 0.083 | 0.083 | 0.083 | 0.083 |
| | F | 0.083 | 0.083 | 0.083 | 0.25 | 0.083 | 0.083 |
| $AUC_{0-t}$ (µg · hr/mL) | M | 3,004 | 1,542 | 6,866 | 5,037 | 16,550 | 8,873 |
| | F | 2,692 | 1,747 | 5,107 | 3,859 | 15,521 | 8,368 |
| $t_{1/2}$ (hr) | M | 0.806 | 0.835 | 1.19 | 1.13 | 1.96 | 1.34 |
| | F | 0.713 | 0.791 | 1.01 | 0.994 | 1.63 | 1.62 |

The pharmacokinetic parameters for CoQ10 IV Formulation in beagle dogs were determined in the toxicokinetic evaluations for two toxicity studies. Charles River Study Number 20000713 was a rising-dose study with a subsequent 5- to 7-day treatment phase. In the rising dose phase of the study Tables 16-18), one group of two male and two female dogs received 250 mg/kg CoQ10 IV Formulation as a single bolus intravenous injection. In the multiple-dose phase of the study (Table 19), one group of two male and two female dogs received 125 mg/kg CoQ10 IV Formulation on Days 1, 3 and 5 as bolus intravenous injections. For males on Day 5, the amount of CoQ10 IV Formulation was indeterminate, and the males were re-dosed on Day 7. Plasma samples were collected at 5 and 15 minutes, and at 1, 4, and 24 hr post-dose on Day 1 of the rising-dose phase and on Days 1 and 5 (females) or 7 (males) of the multiple-dosing phase. Exposure, as measured by $C_{max}$ and $AUC_{0-24}$ was approximately twice as high for 250 mg/kg as for 125 mg/kg. There was a possibly longer half-life for 250 mg/kg (5.94 to 8.16 hr) than for 125 mg/kg (2.07 to 4.87 hr). During dosing on alternate days, the parameters were similar for Day 1 and Day 7 for males and for Day 1 and Day 5 for females. There were no consistent gender differences for any of the pharmacokinetic parameters.

In the second dog toxicity study, Charles River Study Number 20000334, CoQ10 IV Formulation was adminisexception of one high-dose female with a $T_{max}$ value of 0.5 hr, all other $T_{max}$ values occurred at the first or second sampling time. For the low- and mid-dose groups on both days and high-dose animals on Day 26, the mean tin values ranged from 1.91 to 3.62 hr. For high-dose males and females on Day 1, the mean tu2 values were 3.92 and 4.14 hr, respectively. There was no apparent gender difference for any of the pharmacokinetic parameters.

A non-GLP four-week toxicity study was conducted using sub-adult male macaques (The Mannheimer Foundation Study 2010-01). Groups of four macaques received vehicle, 31.25, 62.5, or 125 mg/kg CoQ10 by intravenous injection three times weekly for four weeks. Plasma samples for toxicokinetic analysis were collected pre-dose, and at 0.25, 1, 6, 24, and 48 hr postdose on the first day of dosing. Pre-dose, but no post-dose samples were collected on Days 7, 14, 21 and 29. Preliminary results show that $C_{max}$ and $AUC_{0-t}$ increased with increasing dose. The increases for $C_{max}$ were slightly greater than directly dose-proportional. The increases for $AUC_{0-t}$ were apparently substantially greater than directly dose-proportional, but the nonlinearity may be in part a reflection of the sampling schedule. $T_{max}$ occurred at the first sampling time, 0.25 hr, except for one animal with $T_{max}$ at 1 hr. Due to lack of sampling times between 6 and 24 hr, firm conclusions could not be drawn for $t_{1/2}$.

The four-week toxicity studies in rats, dogs, and macaques showed increases in $C_{max}$ and $AUC_{0-t}$ with dose. Non-linearity was observed for some increases, but linearity was observed for others. The rat and dog studies, which included animals of both sexes, did not reveal any apparent gender difference in the pharmacokinetics.

Samples of liver, lungs, spleen, pancreas and brain were collected from mice after a single administration of 100 mg/kg CoQ10 in Formulation 1 or 2 (Tables 21-23). The samples of liver, lungs, spleen, pancreas and brain were collected from mice after a single administration of 100 mg/kg CoQ10 in Formulation 1 or 2 (Tables 21-23). The samples of liver, lungs, spleen and pancreas were collected at 2, 4, 8, 12, 24 and 36 hr post-dose. Samples of brain were collected at 12, 24 and 36 hr post-dose. Samples of all tissues were also collected from mice that were not treated. None of the samples from the untreated mice had any measurable CoQ10 concentrations. The results for the post-dose samples were similar for Formulation 1 and Formulation 2. The results for the tissues indicated that there was high uptake of CoQ10 IV Formulation by the liver and spleen, intermediate uptake by the lungs, and very little uptake by the pancreas. The very limited data for brain indicated possible brain levels similar to plasma concentrations, at least from 12 to 36 hr.

TABLE 21

Pharmacokinetics: Organ Distribution

| Location in CTD | m4-2-2-2 |
| --- | --- |
| Study No. | EB08-014-12a |
| Species: | Mouse |
| Gender (M/F)/Number of animals: | 18 F per Formulation Group |
| Feeding condition: | NA |
| Vehicle/Formulation: | Formulation 1 without poloxamer; Formulation 2 with poloxamer |
| Method of Administration: | IV |
| Dose (mg/kg): | 100 |
| Analyte: | 31510 |
| Assay: | LC/MS/MS |

| Tissue Concentrations (µg/g) | | 2 hr | 4 hr | 8 hr | 12 hr | 24 hr | 36 hr |
| --- | --- | --- | --- | --- | --- | --- | --- |
| Liver | Formulation 1 | 273 | 387 | 421 | 320 | 307 | 294 |
| | Formulation 2 | 178 | 235 | 213 | 206 | 205 | 168 |
| Spleen | Formulation 1 | 220 | 387 | 458 | 424 | 328 | 323 |
| | Formulation 2 | 217 | 254 | 204 | 214 | 256 | 210 |
| Lungs | Formulation 1 | 104 | 32.6 | 32.5 | 24.8 | 21.3 | 33.1 |
| | Formulation 2 | 74.9 | 49.2 | 39.7 | 18.6 | 31.7 | 23.9 |
| Pancreas | Formulation 1 | 6.47 | 0 | 0 | 0 | 0 | 0 |
| | Formulation 2 | 4.78 | 1.98 | 1.25 | 0.883 | 3.43 | 0 |
| Brain | Formulation 1 | — | — | — | 1.45 | 8.65 | 4.45 |
| | Formulation 2 | — | — | — | 8.35 | 3.90 | 5.40 |

Additional Information: Tissues were collected from 3 mice with no treatment, and there was no measurable 31510 in the tissues.

TABLE 22

Pharmacokinetics: Organ Distribution (cont'd)

| Location in CTD | m4-2-2-2 |
| --- | --- |
| Study No. | 20000328 |
| Species: | Rats |
| Gender (M/F)/Number of animals: | 5 M/5 F per dose group |
| Feeding condition: | Fed |
| Vehicle/Formulation: | Sterile API 31510 for Injection |
| Method of Administration: | IV three times weekly |
| Duration: | 4 Weeks |
| Analyte: | 31510 |
| Assay: | LC/MS/MS |

| Dose (mg/kg) | | 0 | 62.5 | 125 | 250 |
| --- | --- | --- | --- | --- | --- |
| Tissue Concentrations (µg/g) | | ~72 hr | ~72 hr | ~72 hr | ~72 hr |
| Liver | Males | <50 | 1,816 | 5,352 | 9,506 |
| | Females | <50 | 2,976 | 6,292 | 9,420 |
| Lungs | Males | <25 | 34.7 | 162 | 495 |
| | Females | <25 | 12.0 | 98.1 | 374 |
| Pancreas | Males | <25 | 14.4 | 20.1 | 71.2 |
| | Females | <25 | 17.0 | 19.4 | 113 |
| Brain | Males | <25 | <25 | <25 | 10.6 |
| | Females | <25 | <25 | <25 | <25 |

Note:
For mean values listed as <25 µg/g, all samples in the group were below the limit of quantitation. For other groups with one or more samples below the limit of quantitation, the BLQ values were set to 0 µg/g for calculation of the mean, resulting in some mean values below 25 µg/g.

TABLE 23

Pharmacokinetics: Organ Distribution (cont'd)

| Location in CTD | m4-2-2-2 |
| --- | --- |
| Study No. | 20000334 |
| Species: | Dogs |
| Gender (M/F)/Number of animals: | 3 M/3 F per dose group |
| Feeding condition: | Fed |
| Vehicle/Formulation: | Sterile API 31510 for Injection |
| Method of Administration: | IV three times weekly |
| Duration: | 4 Weeks |
| Analyte: | 31510 |
| Assay: | LC/MS/MS |

| Dose (mg/kg) | | 0 | 31.25 | 62.5 | 125 |
| --- | --- | --- | --- | --- | --- |
| Tissue Concentrations (µg/g) | | ~72 hr | ~72 hr | ~72 hr | ~72 hr |
| Liver | Males | 43.8 | 843 | 2,403 | 6,267 |
| | Females | <50 | 1,024 | 2,923 | 4,780 |
| Lungs | Males | <25 | <25 | 13.0 | 52.1 |
| | Females | <25 | <25 | 10.1 | 27.7 |
| Pancreas | Males | <25 | <25 | <25 | <25 |
| | Females | <25 | <25 | <25 | <25 |

TABLE 23-continued

| Pharmacokinetics: Organ Distribution (cont'd) | | | | | |
|---|---|---|---|---|---|
| Brain | Males | <25 | <25 | <25 | <25 |
| | Females | <25 | <25 | <25 | <25 |

Note:
For mean values listed as <25 or <50 μg/g, all samples in the group were below the limit of quantitation. For other groups with one or more samples below the limit of quantitation, the BLQ values were set to 0 μg/g for calculation of the mean, resulting in some mean values below 25 or 50 μg/g.

In Charles River Study Number 20000328, samples of liver, lung, pancreas, and brain were collected from rats at approximately 72 hr after the end of four weeks of three times weekly intravenous administration of 0, 62.5, 125 or 250 mg/kg/dose of CoQ10 IV Formulation (Tables 21-23). There were no measurable concentrations of CoQ10 IV Formulation in any of the tissues from the control group. At 72 hr post-dose, there were high concentrations in the liver that were approximately linearly dose-dependent. Concentrations in the lung and pancreas were lower than in the liver. Only two of the high-dose males had measurable concentrations of CoQ10 IV Formulation in the brain; all others did not have measurable concentrations. There were no apparent gender differences in the tissue concentrations.

In Charles River Study Number 20000334, samples of liver, lung, pancreas, and brain were collected from dogs at approximately 72 hr after the end of four weeks of three times weekly intravenous administration of 0, 31.25, 62.5, or 125 mg/kg/dose of CoQ10 (Tables 21-23). There were no measurable concentrations of CoQ10 IV Formulation in the lung, pancreas or brain samples from the control group. Two males in the control group had low levels of CoQ10 IV Formulation in the liver samples, indicating low levels of endogenous CoQ10 IV Formulation. At 72 hr post-dose, there were high concentrations in the liver samples from CoQ10 IV Formulation-treated dogs. The mean concentrations were approximately linearly dose-dependent. Concentrations in the lung were less than 1% of the concentrations in the liver. None of the pancreas or brain samples had measurable concentrations. There were no apparent gender differences in the tissue concentrations.

FIG. 47 shows the mean liver concentrations of CoQ10 IV Formulation versus dose for male and female rats and dogs. It shows that the dose dependencies are similar for rats and dogs, and there is no apparent gender difference for either species.

The four-week toxicity studies in rats and dogs showed increases in $C_{max}$ and $AUC_{0-t}$ with dose. Non-linearity was observed for some increases, but linearity was observed for others. The rat and dog studies, which included animals of both sexes, did not reveal any apparent gender difference in the pharmacokinetics.

The results of the tissue-distribution study in mice indicated that there was high uptake of CoQ10 IV Formulation by the liver and spleen, intermediate uptake by the lungs, and very little uptake by the pancreas. The very limited data for mouse brain indicated possible brain levels similar to plasma concentrations, at least from 12 to 36 hr. The published studies of distribution in rats and mice are in general agreement with the limited data from the study of CoQ10 IV Formulation in mice.

The necropsy samples taken 72 hr after the last dose in a four-week treatment period showed high concentrations of CoQ10 IV Formulation in the liver, lower concentrations in the lung, low (rats) or nonmeasurable (dogs) in the pancreas, and no measurable levels in the brain of either species. The dose-dependency of the mean liver concentrations was similar for rats and dogs. There was no apparent gender difference in the tissue concentrations.

Example 20

Single-Dose Toxicology Study of CoQ10 IV Formulation In Rats: In single-dose toxicity studies in rats, Sprague-Dawley rats (n=3/sex/group) received single IV injections of the CoQ10 formulation via the tail vein at 100, 250, 750 mg/kg (using a 45.9 mg/mL formulation), and 750 and 1000 mg/kg (using a 80 mg/mL formulation) (Charles River Study Number 20000711; Table 24). Animals were observed for three days post-dose. One additional group (3/sex) received the vehicle only (3% DMPC and 1.5% Poloxamer 188). An additional 9/sex/group were similarly treated and used for toxicokinetic studies. Parameters evaluated included mortality and reactions to treatment, detailed examinations, body weight, food consumption, hematology and clinical chemistry, gross pathology, and organ weights. Histopathology was conducted on a limited number of tissues (heart, kidney, liver, lung, pancreas, discolored skin samples, lymph nodes) from animals in all groups except 750 mg/kg (45.9 mg/mL). Toxicokinetics was evaluated following each dose.

TABLE 24

| | | | | Single-Dose Toxicity | | | |
|---|---|---|---|---|---|---|---|
| Species/ Strain | Method of Administration (Vehicle) | Doses (mg/kg) | Gender and No. per Group | Observed Maximum Nonlethal Dose (mg/kg) | Approx. Lethal Dose (mg/kg) | Noteworthy Findings | Study Number |
| Sprague-Dawley Rat | IV Bolus (Sponsor-supplied vehicle[0]) | 0, 100[a], 250[a], 750[b], 750[a], 1000[b] | 3M, 3F | 250 | >250-<750 | 0: None<br>100: Discoloration of lymph nodes (F)<br>250: Discoloration of lymph nodes and skin from base of tail to hindlimbs<br>750[a]: Mortality (1F); discoloration of lymph nodes and skin from base of tail to hindlimbs, yellow liver<br>750[b]: Mortality (2M, 2F); discoloration of lymph nodes and skin from base of tail to abdomen, fluid in thoracic cavity; fibrin deposition in kidney (M - FD) and lungs (M&F - FD), hepatocellular necrosis (F - FD) | 20000711 |

TABLE 24-continued

Single-Dose Toxicity

| Species/Strain | Method of Administration (Vehicle) | Doses (mg/kg) | Gender and No. per Group | Observed Maximum Nonlethal Dose (mg/kg) | Approx. Lethal Dose (mg/kg) | Noteworthy Findings | Study Number |
|---|---|---|---|---|---|---|---|
| Beagle Dog | IV Bolus (Sponsor-Supplied Vehicles) | 0 (Vehicle[d]), 0 (Poloxamer 188 in PBS), 0 (Complete Vehicle in PBSe), 125, 250 | 1 to 2M, 1 to 2 F | 125 | >125-<250 | 1000: Mortality (2F); discoloration of lymph nodes and from base of tail to abdomen, yellow liver, fluid in thoracic cavity (F); decreases in male reproduction organ weights; injection site inflammation (M&F - S), fibrin deposition in lungs (F - FD) 0 (Vehicle): Mortality (1M&1F); adverse clinical signs (red urine, dehydration); weight loss and decreased food consumption; significant decreases in red blood cell parameters and changes in cell morphology: discoloration of intestinal contents, kidneys, and carcass, abnormal bladder contents, thick bile; eosinophilic droplets in kidney, congested hepatic sinusoids with crythrophagocytosis by Kupffer cells 0 (Poloxamer 188 in PBS): None 0 (Complete Vehicle in PBS): Mortality (1M&1F); adverse clinical signs (red urine, labored respiration); weight loss and decreased food consumption; significant decreases in red blood cell parameters and changes in cell morphology; discoloration of intestinal contents, kidneys, and carcass, abnormal bladder contents, thick bile; eosinophilic droplets in kidney, congested hepatic sinusoids with crythrophagocytosis by Kupffer cells, chronic renal disease (F) 125: None 250: Mortality (2M&2F); adverse clinical signs (red urine, decreased activity); weight loss and decreased food consumption; significant decreases in red blood cell parameters and changes in cell morphology; discoloration of intestinal contents, kidneys, and carcass, abnormal bladder contents, thick bile; eosinophilic droplets in kidney, congested hepatic sinusoids with crythrophagocytosis by Kupffer cells | 20000713 |

M = Male. F = Female. IV = intravenous injection. FD = Found dead or moribund sacrificed animals. S = Surviving animals. PBS = Phosphate buffered saline.
[a]Concentration of 45.9 mg/mL administered.
[b]Concentration of 90.0 mg/mL administered.
[c]Vehicle components include dimyrstoylphosphatidylcholine (DMPC) (3% w/w) and Poloxamer 188 (1.5% w/w) in PBS.
[d]Vehicle components include dimyrstoylphosphatidylcholine (DMPC) (6% w/w) and Poloxamer 188 (3% w/w) in PBS.
[e]Complete vehicle components include dimyrstoylphatidylcholine (DMPC) (3% w/w) and Poloxamer 188 (1.5% w/w) in PBS.

Animals treated at 100 and 250 mg/kg (using a 45.9 mg/mL formulation) showed no obvious test article-related effects following single dose, and hematology data was generally unremarkable. Doses of 750 and 1000 mg/kg, using the 80 mg/mL formulation, produced mortality (two animals of each sex at 750 mg/kg and two females at 1000 mg/kg). One female given 750 mg/kg with the 45.9 mg/mL formulation also died. These animals appeared normal on the day of dosing, but were found dead or sacrificed moribund the next day.

There were no consistent effects on body weight or food consumption. Clinical chemistry data were also unremarkable.

Necropsy findings at 750 and 1000 mg/kg showed fluid in the thoracic cavity and discolored liver; discolored lymph nodes were noted at 100 and 250 mg/kg. Histopathological evaluation from animals treated at 750 and 1000 mg/kg that died revealed intrathoracic fluid, injection site lesions and discoloration of tissues. Fibrin deposition in the renal glomerulus was seen in the two males that died at 750 mg/kg but not in the two females that died at 1000 mg/kg. Fibrin deposition in the lung was seen in animals that died at both doses. Hepatic necrosis was seen in one animal that died at 750 mg/kg. Tissues were generally normal among survivors at these two doses except for vascular inflammation at the injection site. Evaluation of vehicle treated animals was generally unremarkable except for eosinophilic crystals in the kidney (one female), alveolar epithelial hyperplasia in the lung (one female) and minimal inflammation in the pancreas (one female). These changes are likely incidental.

Example 21

Single-Dose Toxicology Study of CoQ10 IV Formulation In Dogs: Beagle dogs (n=1 or 2/sex) received single doses of sterile CoQ10 nano-suspension for injection as a slow bolus IV injection at 250 and 125 mg/kg (Charles River Laboratories Study Number 20000713; Table 24). To evaluate the possible effect of the vehicle following the observed significant toxicity observed at 250 mg/kg (using vehicle containing 6% DMPC and 3% Poloxamer 188), additional groups of dogs were treated with the vehicle (6% DMPC and 3% Poloxamer), the "complete" vehicle (3% DMPC and 1.5% Poloxamer 188), or PBS/Poloxamer (a suitable formulation of DMPC in PBS could not be prepared). The initial injection rate for the 250 mg/kg dose and for the vehicle was 5.44 mL/kg based on a formulation of CoQ10 concentration of 45.9 mg/mL. The injection rate for the 125 mg/kg dose was 3.51 mL/kg based on a formulation of CoQ10 concentration of 35.6 mg/mL. Parameters evaluated included mortality and reactions to treatment, detailed examinations, body weight, food consumption, hematology and biochemistry, gross pathology, and organ weights and limited histopathology (heart, kidney, liver, lung, pancreas, discolored skin from dogs dosed with 250 mg/kg, vehicle, and the complete vehicle). Toxicokinetics was determined after each dose.

The two males and two females dosed with 250 mg/kg were moribund sacrificed on Day 2 due to significant adverse clinical signs. To evaluate the possible role of the vehicle, the vehicle was administered to another group of 1/sex. Observed responses were the same, including moribund euthanasia, as seen with the animals treated at 250 mg/kg, suggesting this dose of vehicle was responsible for some, if not all of the effects noted. This was confirmed when another male and female were dosed with the complete vehicle at the same rate of 5.44 mL/kg. Administration of PBS and Poloxamer 188 to another male and female dog produced no such effects, suggesting that the DMPC in the vehicle formulation with the higher concentration of excipients was the component causing the effects. In a fifth group of 1/sex, the drug formulation was given at 125 mg/kg using a reduced dose volume of 3.51 mL/kg. Effects were limited to emesis and soft stools, but the animals survived.

Adverse effects on body weight, food consumption, clinical pathology (hemolysis), gross pathology changes in the kidneys, gastrointestinal tract, gallbladder, and urinary bladder, and microscopic changes consistent with hemolysis in the kidneys and livers were only noted in the animals administered 250 mg/kg, the vehicle and the complete vehicle. No findings were noted in the dogs administered PBS/Poloxamer 188 or 125 mg/kg.

Toxicokinetic data showed dose proportional increases in $C_{max}$ and AUC and slightly increased half-life at 250 mg/kg/dose than at 125 mg/kg/dose.

Example 22

Repeat-Dose Toxicology Study of CoQ10 IV Formulation In Rats: In a one-week repeat dose study in rats, two groups of 5 rats/sex received 250 and 500 mg/kg every 3 days for a total of three doses (Charles River Laboratories Study Number 20000711; Table 25). Parameters evaluated included mortality and reactions to treatment, detailed examinations, body weight, and gross pathology (on animals that died). Histopathology was not conducted on these animals. Toxicokinetics was evaluated on the last day of treatment. No adverse clinical signs were seen at 250 mg/kg/dose. At 500 mg/kg/dose, four animals died or were sacrificed in a moribund condition: two males found dead on Day 2, one female euthanized moribund on Day 3 (clinical signs of hypothermia and decreased activity), and one female found dead on Day 6. Survivors at 500 mg/kg/dose showed no adverse clinical signs. Animals at both doses generally maintained (males) or gained (females) body weight through Day 4, and thereafter experienced slight weight loss. Hematological data indicated increased reticulocytes and various while blood cell types at 500 mg/kg/day. Slight polychromasia and/or anisocytosis were seen among some animals at both doses. At the end of the treatment period (three doses), increased values for ALT, AST, GGT and urea nitrogen were noted among animals receiving 500 mg/kg/dose as well as decreases in total protein, albumin and globulin. At necropsy, discolored lymph nodes, discoloration of the subcutaneous layer of the skin and pale liver as well as injection site lesions were observed. Compared to animals at 250 mg/kg/dose, decreased weights of the thymus, epididymides, prostate, seminal vesicles, ovaries and uterus were noted, as well as an increase in liver weights in females. No histopathology was performed.

Toxicokinetic data showed that, in general, plasma concentrations, $C_{max}$ and $AUC_{0-t}$ values of CoQ10 increased with increasing dose. Based on these results, 250 mg/kg/dose was selected as the high dose in the definitive study.

TABLE 25

Repeat-Dose Toxicity

| Species/ Strain | Method of Administration (Vehicle) | Duration of Dosing[a] | Doses (mg/kg/day) | Gender and No. per Group | NOAEL (mg/kg/dose) | Noteworthy Findings | Study Number |
|---|---|---|---|---|---|---|---|
| Sprague-Dawley Rat | IV Bolus (Sponsor-supplied vehicle[b]) | 7 Days | 250, 500 | 5M, 5F | <250 | 250: Weight loss; discoloration of lymph nodes and subcutaneous skin, pale liver; 500: Mortality (2M&2F); increased weight loss; decreased food consumption; hematology and clinical chemistry alterations; discoloration of lymph nodes and subcutaneous skin, pale liver, decreased thymus and reproductive organ weights, increased liver weight | 20000711 |
| Beagle Dog | IV Bolus (Sponsor-supplied vehicle[b]) | 5 or 7 Days | 125 | 2M, 2F | 125 | 125: None | 20000713 |

M = Male. F = Female. IV = Intravenous injection.
[a]Doses administered every other day for 5 or 7 days.
[b]Vehicle components include DMPC (3% w/w) and Poloxamer 188 (1.5% w/w) in PBS.

Example 23

4-Week Repeat-Dose Toxicology Study of CoQ10 IV Formulation In Rats: Four groups of young adult Sprague Dawley rats (n=10/sex/group) received the vehicle (PBS containing Poloxamer 188 and DMPC) or the test article at doses of 0, 62.5, 125 and 250 mg/kg by IV injection three times per week (Charles River Laboratories Study Number 20000328; Table 26). An additional 5 rats/sex were included in each group and were maintained after treatment for a 2-week recovery period. A single batch (#0494-02-021) of test article with a target concentration of 40 mg/mL of CoQ10 was provided for use on the study. The doses of 62.5, 125 and 250 mg/kg were achieved using dose volumes of 1.56, 3.13, and 6.25 mL/kg, respectively. The vehicle was administered at the same dose volume as the high-dose group. Additionally, three groups of 9 animals/sex served as toxicokinetic (TK) animals and received the test article in the same manner as the main study groups. Parameters evaluated included cageside observations, clinical observations, body weight, food consumption, ophthalmology, clinical pathology evaluations (hematology, coagulation tests, clinical chemistry, and urinalysis), gross pathology, and organ weights. Histopathology was conducted on all tissues in control and high-dose groups from animals sacrificed at the end of the treatment period, and on bone marrow, kidney, liver, mandibular and mesenteric lymph nodes and spleen from animals in the low and middle dose groups. Examination of animals from the recovery sacrifice was limited to those tissues showing gross lesions, and included liver and lymph nodes. Blood samples for determination of the plasma concentrations of the test article were collected from cohorts of three TK animals per sex per dose group at 5, 15 and 60 minutes and at 4, 24 and 48 hours after dosing on Days 1 and 28 (after the last dose).

TABLE 26

Repeat-Dose Toxicity
Report Title: A 4-Week Toxicity Study of 31510
Administered by Intravenous (Bolus) Injection to
Rats with a 2-Week Recovery Period Species/Strain: Sprague-Dawley Rat  Duration of Dosing: 4 Weeks  Study No.: 2000328
Initial Age: Approximately 8 Weeks  Duration Postdose: 2 Weeks  Location in CTD: m4-2-3-2
Date of First Dose: 14 Apr. 2010  Method of Administration:  GLP Compliance: Yes
Intravenous (bolus) injection
Vehicle/Formulation:
DMPC and Poloxamer 188 in PBS Special Features: Dosing occurred three times per week (Monday, Wednesday, Friday).
A single concentration of material was supplied (40 mg/mL): doses wore achieved by varying the dose volume.
Severely Toxic Dose to 10% of animals (STD10): 62.5 mg/kg/dose

| | Dose (mg/kg) | | | | | | | |
|---|---|---|---|---|---|---|---|---|
| | 0 | | 62.5 | | 125 | | 250 | |
| Number of Animals | M: 15 | F: 15 | M: 15 | F: 15 | M: 15 | F: 15 | M: 15 | F: 15 |
| Toxicokinetics: | | | | | | | | |
| $AUC_{0-t}$ (µg · hr/mL) | | | | | | | | |
| Day 1 | NA | NA | 3004 | 2692 | 6866 | 5107 | 16550 | 15521 |
| Day 26 | NA | NA | 1953 | 1747 | 5037 | 3859 | 8873 | 8368 |
| Noteworthy Findings | | | | | | | | |
| Died or Sacrificed Moribund | 0 | 0 | 0 | 0 | 0 | 0 | 0 | 0 |
| Body Weight ($\%^a$) (g) | 404 | 258 | −0.5 | −1.7 | −8.7* | −5.5 | −17.6* | −8.9* |
| Food Consumption ($\%^a$) (g/animal/day) | 31 | 25 | +2.5 | −4.0 | −9.2* | −12.5* | −16.4* | −18.3* |
| Clinical Observations | — | — | — | — | — | — | — | — |
| Ophthalmology | — | — | — | — | — | — | — | — |
| Hematology | | | | | | | | |
| Erythrocytes ($10^6$/cmm) | 6.47 | 5.99 | 8.14* | 7.77* | 7.59* | 6.90* | 6.23 | 6.12 |
| Hemoglobin (g/dL) | 14.3 | 13.7 | 15.1* | 14.7* | 14.3 | 13.5 | 12.9* | 13.2 |
| Hematocrit (%) | 43.2 | 40.7 | 44.3 | 42.4* | 41.6* | 39.1* | 40.4* | 39.2* |
| Leukocytes ($10^3$/cmm) | 12.71 | 9.32 | 8.56* | 8.33 | 11.03 | 9.49 | 15.55* | 13.15* |
| Lymphocytes ($10^3$/cmm) | 10.88 | 7.85 | 7.02* | 6.79 | 8.70* | 7.35 | 12.58 | 10.50* |
| Neutrophils ($10^3$/cmm) | 1.39 | 1.06 | 1.06 | 1.06 | 1.71 | 1.64 | 2.13* | 1.97* |
| Eosinophils ($10^3$/cmm) | 0.05 | 0.08 | 0.09* | 0.09 | 0.08 | 0.08 | 0.14* | 0.10 |
| Coagulation | | | | | | | | |
| APPT (seconds) | 17.5 | 15.8 | 17.6 | 15.1 | 15.9* | 14.4* | 14.7* | 14.5* |
| Clinical Chemistry | | | | | | | | |
| AST (IU/L) | 79 | 99 | 74 | 67* | 83 | 76* | 113* | 88 |
| ALT (IU/L) | 21 | 21 | 22 | 19 | 25 | 20 | 35* | 22 |
| GGT (IU/L) | 0.00 | 0.32 | 0.00 | 0.42 | 0.09 | 0.53 | 0.16 | 0.25 |
| Cholesterol (g/dL) | 37 | 56 | 45 | 51 | 45 | 52 | 65* | 69* |

TABLE 26-continued

Repeat-Dose Toxicity
Report Title: A 4-Week Toxicity Study of 31510
Administered by Intravenous (Bolus) Injection to
Rats with a 2-Week Recovery Period

| | M: 10 | F: 10 | M: 10 | F: 10 | M: 10 | F: 10 | M: 10 | F: 10 |
|---|---|---|---|---|---|---|---|---|
| Urinalysis | — | — | — | — | — | — | — | — |
| Number Examined | M: 10 | F: 10 | M: 10 | F: 10 | M: 10 | F: 10 | M: 10 | F: 10 |
| Gross Pathology | | | | | | | | |
| Pale Adrenal | 0 | 0 | 0 | 0 | 0 | 0 | 4 | 2 |
| Pale Liver | 1 | 0 | 9 | 7 | 9 | 10 | 10 | 10 |
| Pale Lymph Nodes | 0 | 0 | 0 | 1 | 4 | 0 | 8 | 7 |
| Enlarged Pancreatic Lymph Nodes | 0 | 0 | 0 | 0 | 1 | 1 | 5 | 1 |
| Pale Ovaries | NA | 0 | NA | 0 | NA | 1 | NA | 9 |
| Pale Pituitary | 0 | 0 | 0 | 0 | 0 | 0 | 3 | 0 |
| Pale SQ Skin | 0 | 0 | 1 | 0 | 1 | 3 | 0 | 4 |
| Organ Weights | | | | | | | | |
| Liver ($\%^b$) (g) | 10.91 | 7.54 | −5.5 | −6.1 | −7.2 | −0.6 | +11.0 | +14.5* |
| Spleen ($\%^b$) (g) | 1.95 | 1.17 | −57.3* | −48.2* | −23.4 | −11.2 | +65.9 | +51.0* |
| Histopathology Adrenal Gland | | | | | | | | |
| Vacuolation | 1 | 0 | NE | NE | NE | NE | 10 | 10 |
| Minimal | 1 | 0 | | | | | 0 | 0 |
| Mild | 0 | 0 | | | | | 5 | 3 |
| Moderate | 0 | 0 | | | | | 5 | 7 |
| Bone Marrow, Sternum | | | | | | | | |
| Hyperplasia | 0 | 0 | 0 | 0 | 2 | 0 | 4 | 0 |
| Minimal | 0 | 0 | 0 | 0 | 2 | 0 | 0 | 0 |
| Mild | 0 | 0 | 0 | 0 | 0 | 0 | 4 | 0 |
| Injection Site | | | | | | | | |
| Mononuclear Cell Infiltration | 2 | 5 | NE | NE | 1 | NE | 10 | 10 |
| Minimal | 1 | 4 | | | 0 | | 0 | 0 |
| Mild | 1 | 1 | | | 0 | | 0 | 1 |
| Moderate | 0 | 0 | | | 0 | | 9 | 7 |
| Marked | 0 | 0 | | | 1 | | 1 | 2 |
| Liver | | | | | | | | |
| Focal Necrosis | 0 | 0 | 0 | 1 | 0 | 0 | 0 | 0 |
| Minimal | 0 | 0 | 0 | 1 | 0 | 0 | 0 | 0 |
| Histiocytic Infiltration | 0 | 0 | 2 | 7 | 6 | 9 | 10 | 9 |
| Minimal | 0 | 0 | 1 | 7 | 3 | 1 | 1 | 4 |
| Mild | 0 | 0 | 1 | 0 | 3 | 7 | 7 | 5 |
| Moderate | 0 | 0 | 0 | 0 | 0 | 1 | 2 | 0 |
| Vacuolation | 1 | 0 | 2 | 7 | 8 | 10 | 10 | 10 |
| Minimal | 1 | 0 | 2 | 7 | 4 | 6 | 0 | 0 |
| Mild | 0 | 0 | 0 | 0 | 4 | 4 | 10 | 10 |
| Lymph Node, Man. | | | | | | | | |
| Histiocytic Infiltration | 0 | 0 | 6 | 4 | 7 | 3 | 9 | 9 |
| Minimal | 0 | 0 | 4 | 4 | 3 | 2 | 0 | 7 |
| Mild | 0 | 0 | 1 | 0 | 4 | 0 | 3 | 1 |
| Moderate | 0 | 0 | 1 | 0 | 0 | 1 | 6 | 1 |
| Lymph Node, Mes. | | | | | | | | |
| Histiocytic Infiltration | 0 | 1 | 9 | 9 | 10 | 10 | 9 | 9 |
| Minimal | 0 | 1 | 5 | 7 | 4 | 5 | 1 | 5 |
| Mild | 0 | 0 | 4 | 2 | 6 | 5 | 7 | 4 |
| Moderate | 0 | 0 | 0 | 0 | 0 | 0 | 1 | 0 |
| Ovary | | | | | | | | |
| Histiocytic Infiltration | NA | 0 | NA | 0 | NA | 10 | NA | 10 |
| Minimal | | 0 | | 0 | | 10 | | 0 |
| Mild | | 0 | | 0 | | 0 | | 6 |
| Moderate | | 0 | | 0 | | 0 | | 4 |
| Skin, Dermis | | | | | | | | |
| Histiocytic Infiltration | 0 | 0 | 0 | 0 | 1 | 2 | 0 | 2 |
| Mild | 0 | 0 | 0 | 0 | 0 | 1 | 0 | 0 |
| Moderate | 0 | 0 | 0 | 0 | 0 | 1 | 0 | 2 |
| Marked | 0 | 0 | 0 | 0 | 1 | 0 | 0 | 0 |
| Skin, SQ | | | | | | | | |
| Histiocytic Infiltration | 0 | 0 | 0 | 0 | 0 | 2 | 0 | 0 |
| Mild | 0 | 0 | 0 | 0 | 0 | 2 | 0 | 0 |

TABLE 26-continued

Repeat-Dose Toxicity
Report Title: A 4-Week Toxicity Study of 31510
Administered by Intravenous (Bolus) Injection to
Rats with a 2-Week Recovery Period

| Spleen | | | | | | | | |
|---|---|---|---|---|---|---|---|---|
| Histiocytic Infiltration | 0 | 0 | 1 | 4 | 8 | 9 | 10 | 10 |
| Mild | 0 | 0 | 0 | 4 | 5 | 4 | 0 | 1 |
| Moderate | 0 | 0 | 1 | 0 | 3 | 3 | 9 | 7 |
| Marked | 0 | 0 | 0 | 0 | 0 | 1 | 1 | 2 |
| Post-Dose Evaluations | | | | | | | | |
| Number of Animals | M: 5 | F: 5 | M: 5 | F: 5 | M: 5 | F: 5 | M: 5 | F: 5 |
| Body Weight (%$^a$) (g) | 449 | 280 | +7.4 | −0.9 | −2.2 | −3.9 | −15.0* | −12.6 |
| Food Consumption (%$^a$) (g/animal/day) | 35 | 28 | +5.8 | −7.9 | +1.2 | −10.5 | −14.1 | +0.7 |
| Coagulation | | | | | | | | |
| APPT (seconds) | 17.8 | 15.6 | 16.7 | 14.4 | 15.9* | 15.4 | 15.3* | 14.7 |
| Clinical Chemistry | | | | | | | | |
| AST (IU/L) | 78 | 71 | 79 | 83 | 94 | 68 | 213* | 153* |
| ALT (IU/L) | 22 | 20 | 20 | 19 | 27 | 21 | 96* | 63* |
| GGT (IU/L) | 0.00 | 0.14 | 0.00 | 0.12 | 0.00 | 0.63* | 0.42 | 0.58* |
| Cholesterol (g/dL) | 36 | 47 | 49 | 45 | 47 | 52 | 50 | 60 |
| Gross Pathology | | | | | | | | |
| Pale Liver | 0 | 0 | 2 | 3 | 5 | 5 | 5 | 5 |
| Pale Iliac Lymph Node | 0 | 0 | 2 | 2 | 2 | 3 | 3 | 4 |
| Pale Pancreatic Lymph Node | 0 | 0 | 1 | 1 | 2 | 2 | 3 | 3 |
| Pale Ovaries | NA | 0 | NA | 0 | NA | 0 | NA | 4 |
| Enlarged Spleen | 0 | 0 | 0 | 0 | 1 | 0 | 4 | 2 |
| Organ Weights | | | | | | | | |
| Liver (%$^b$) (g) | 11.54 | 7.58 | +5.0 | +4.6 | −2.5 | +3.5 | +7.6 | +19.6 |
| Spleen (%$^b$) (g) | 1.15 | 0.76 | −22.2 | +0.5 | +5.9 | −3.4 | +38.7* | +82.7* |
| Histopathology | | | | | | | | |
| Adrenal Gland | | | | | | | | |
| Vacuolation | 0 | 0 | 5 | 3 | 5 | 5 | 4 | 5 |
| Minimal | 0 | 0 | 2 | 3 | 0 | 0 | 0 | 0 |
| Mild | 0 | 0 | 3 | 0 | 2 | 4 | 2 | 0 |
| Moderate | 0 | 0 | 0 | 0 | 3 | 1 | 2 | 4 |
| Marked | 0 | 0 | 0 | 0 | 0 | 0 | 0 | 1 |
| Liver | | | | | | | | |
| Focal Necrosis | 0 | 0 | 0 | 0 | 3 | 0 | 2 | 1 |
| Minimal | 0 | 0 | 0 | 0 | 2 | 0 | 0 | 0 |
| Mild | 0 | 0 | 0 | 0 | 1 | 0 | 1 | 1 |
| Liver | | | | | | | | |
| Multifocal Necrosis | 0 | 0 | 0 | 0 | 0 | 1 | 1 | 1 |
| Mild | 0 | 0 | 0 | 0 | 0 | 1 | 1 | 0 |
| Moderate | 0 | 0 | 0 | 0 | 0 | 0 | 0 | 1 |
| Histiocytic Infiltration | 0 | 0 | 1 | 5 | 5 | 5 | 5 | 5 |
| Minimal | 0 | 0 | 1 | 3 | 4 | 2 | 1 | 0 |
| Mild | 0 | 0 | 0 | 2 | 1 | 3 | 4 | 1 |
| Moderate | 0 | 0 | 0 | 0 | 0 | 0 | 0 | 4 |
| Vacuolation | 0 | 0 | 5 | 5 | 5 | 5 | 5 | 5 |
| Minimal | 0 | 0 | 4 | 2 | 1 | 0 | 0 | 0 |
| Mild | 0 | 0 | 1 | 2 | 4 | 4 | 0 | 0 |
| Moderate | 0 | 0 | 0 | 1 | 0 | 1 | 5 | 5 |
| Lymph Node, Man. | | | | | | | | |
| Histiocytic Infiltration | 0 | 0 | 4 | 2 | 5 | 1 | 5 | 5 |
| Minimal | 0 | 0 | 4 | 2 | 3 | 2 | 2 | 1 |
| Mild | 0 | 0 | 0 | 0 | 2 | 0 | 1 | 3 |
| Moderate | 0 | 0 | 0 | 0 | 0 | 0 | 2 | 1 |
| Lymph Node, Mes. | | | | | | | | |
| Histiocytic Infiltration | 0 | 0 | 5 | 4 | 5 | 5 | 5 | 5 |
| Minimal | 0 | 0 | 4 | 4 | 3 | 4 | 0 | 0 |
| Mild | 0 | 0 | 1 | 0 | 1 | 1 | 5 | 5 |

TABLE 26-continued

Repeat-Dose Toxicity
Report Title: A 4-Week Toxicity Study of 31510
Administered by Intravenous (Bolus) Injection to
Rats with a 2-Week Recovery Period

| Ovary | | | | | | | | |
|---|---|---|---|---|---|---|---|---|
| Histiocytic Infiltration | NA | 0 | NA | 4 | NA | 5 | NA | 5 |
| Minimal | | 0 | | 4 | | 3 | | 0 |
| Mild | | 0 | | 0 | | 2 | | 4 |
| Moderate | | 0 | | 0 | | 0 | | 1 |
| Spleen | | | | | | | | |
| Histiocytic Infiltration | 0 | 0 | 2 | 3 | 3 | 2 | 5 | 5 |
| Minimal | 0 | 0 | 2 | 2 | 2 | 2 | 0 | 1 |
| Mild | 0 | 0 | 0 | 1 | 1 | 0 | 3 | 4 |
| Moderate | 0 | 0 | 0 | 0 | 0 | 0 | 1 | 0 |
| Marked | 0 | 0 | 0 | 0 | 0 | 0 | 1 | 0 |

— No noteworthy findings. NA = Not applicable. NE = Not examined. ?SQ = Subcutaneous. Man = Mandibular. Mes. = Mesenteric.
*p < 0.05 (Anova/Dunnett or Kruskal-Wallis/Dunn's Test).
[a]At end of dosing or recovery period. For controls, group means are shown. For the treated groups, group mean percent differences from controls are shown.
[b]Both absolute and relative weights differed from controls in the direction indicated. Number indicates percent difference for the absolute organ weights.

All animals survived to terminal euthanasia. No adverse test article-related effects on clinical observations, ophthalmology, hematology, or urinalysis parameters were observed. Decreased body weight gains and food consumption were observed for animals treated at the high dose and to a lesser extent at the middle dose. Some recovery was seen at the end of the non-treatment period.

Evaluation of hematological data revealed a slight but inconsistent decrease in red cell parameters that was primarily limited to the high dose males. Reticulocytes were not meaningfully affected. Activated partial thromboplastin time was somewhat longer among the high dose animals that tended to persist through the recovery period. Elevation in total white cell counts, also reflected in increases in neutrophils, eosinophils or lymphocytes were see at the highest dose only. Clinical chemistry data revealed increased values for AST, ALT, GGT and cholesterol for the high dose males at the end of the treatment period and were more pronounced at the end of the recovery period. For females, the increases were seen only at the end of the recovery period.

At necropsy (terminal and recovery), test article-related gross changes included pale discoloration of the liver and pale discoloration/enlargement of multiple lymph nodes at 62.5 mg/kg/dose and above, enlargement of the spleen at 125 mg/kg/dose and above, and pale adrenals, pale ovaries, and subcutaneous skin discoloration at 250 mg/kg/dose. Spleen and liver weights were increased at 250 mg/kg/dose at the terminal and recovery necropsies.

Test article-related histopathological findings at the scheduled termination on Day 29 included mild to moderate cytoplasmic vacuolation of the adrenal cortex (250 mg/kg/dose), minimal to mild erythrocytic hyperplasia in the bone marrow of the sternum of males (≥125 mg/kg/dose), mild to marked mononuclear cell infiltration of the injection site (250 mg/kg/dose), minimal to mild hepatocellular cytoplasmic vacuolation 62.5 mg/kg/dose), minimal to moderate histiocytic cell infiltration of the liver 62.5 mg/kg/dose), minimal to moderate histiocytic cell infiltration of multiple lymph nodes (≥62.5 mg/kg/dose), mild to moderate histiocytic cell infiltration of ovary in females (250 mg/kg/dose females), mild to moderate histiocytic cell infiltration of the dermis and/or subcutis in females (≥125 mg/kg/dose), and minimal to moderate histiocytic cell infiltration of the spleen in males (≥125 mg/kg/dose) and in females (≥62.5 mg/kg/dose). In the recovery animals, similar test article-related lesions were noted as were observed in the main study animals; the severity of these changes followed a dose-response. Findings included: minimal to marked vacuolation of the adrenal gland cortex at ≥62.5 mg/kg/dose (males and females), minimal to moderate focal or mutifocal hepatic necrosis at ≥125 mg/kg/dose (males and females), minimal to moderate histiocytic infiltration and vacuolation of the liver at ≥62.5 mg/kg/dose (males and females), minimal to moderate histiocytic infiltration of the lymph nodes at ≥62.5 mg/kg/dose (males and females), minimal to marked histiocytic infiltration of the spleen at ≥62.5 mg/kg/dose (males and females), and minimal to moderate histiocytic infiltration of the ovaries ≥62.5 mg/kg/dose (females). In several organs/tissues, the severity of the changes seen in the recovery animals, particularly at 125 and 250 mg/kg/dose, were more pronounced than at the terminal necropsy including the adrenal gland, liver, and additional lymph nodes (iliac, renal, pancreatic, cervical, popliteal, mediastinal, and/or brachial).

Toxicokinetic analyses revealed that Cmax and AUC increased in a dose proportional or greater than dose-proportional manner. Values on Day 26 were substantially lower relative to Day 1. There were no notable gender differences. A tabular presentation of pertinent data is shown below (Table 27).

TABLE 27

| | Dose (mg/kg/dose) | | | | | |
|---|---|---|---|---|---|---|
| | 62.5 | | 125 | | 250 | |
| Parameter | M | F | M | F | M | F |
| | Day 1 | | | | | |
| $C_{max}$ (ug/mL) | 1,663 | 1,670 | 3,197 | 2,970 | 6,397 | 6,900 |
| $AUC_{0-24}$ (ug · hr/mL) | 3,004 | 2,692 | 6,866 | 5,107 | 16,550 | 15,521 |

TABLE 27-continued

| | Dose (mg/kg/dose) | | | | | |
|---|---|---|---|---|---|---|
| | 62.5 | | 125 | | 250 | |
| Parameter | M | F | M | F | M | F |
| $T_{max}$ (hr) | 0.083 | 0.083 | 0.083 | 0.083 | 0.083 | 0.083 |
| $T_{1/2}$ (h) | 0.806 | 0.713 | 1.19 | 1.01 | 1.96 | 1.63 |
| Day 26 | | | | | | |
| $C_{max}$ (ug/mL) | 1,052 | 891 | 2,660 | 2,400 | 4,257 | 4,167 |
| $AUC_{0-24}$ (ug · hr/mL) | 1,542 | 1,747 | 5,037 | 3,859 | 8,873 | 8,368 |
| $T_{max}$ (hr) | 0.083 | 0.083 | 0.083 | 0.250 | 0.083 | 0.033 |
| $T_{1/2}$ (h) | 0.835 | 0.791 | 1.13 | 0.994 | 1.34 | 1.62 |

Based on these data, the STD10 was determined to be 62.5 mg/kg/dose.

In a one-week toxicity study in dogs, one group of 2 dogs/sex received 125 mg/kg every 3 days for a total of three doses (Charles River Laboratories Study Number 20000713; Table 25). Parameters evaluated included mortality and reactions to treatment, detailed examinations, body weight, food consumption, cardiology parameters, hematology and clinical chemistry parameters, organ weights and gross pathology. Histopathology was not conducted on these animals. Toxicokinetics was evaluated on the last day of treatment.

No adverse effects were seen at the 125 mg/kg/dose level for any of the parameters evaluated except for a slight reduction in red cell mass and morphology at the end of the treatment period.

Toxicokinetic data showed that plasma concentrations, and mean values for $C_{max}$, $AUC_{0-24}$, and $AUC_{0-\infty}$, of CoQ10 IV Formulation were comparable between the first and the third dose administered.

Based on these results, 125 mg/kg/dose was selected as the high dose in the definitive dog study.

In a 4-week repeat-dose study in dogs, four groups of beagle dogs (n=3/sex/group) received the vehicle or drug product containing CoQ10 N Formulation at doses of 31.25, 62.5 and 125 mg/kg by IV injection daily for four weeks (Charles River Laboratories Study Number 20000334; Table 28). An additional two dogs/sex were included in each group and maintained for a 2-week recovery after treatment. A single test article concentration of 40 mg/mL was provided for use on the study. The doses of 31.25, 62.5 and 125 mg/kg were achieved using dose volumes of 0.78, 1.56 and 3.13 mL/kg, respectively. Parameters evaluated included cageside observations, clinical observations, body weight, food consumption, ophthalmoscopy, electrocardiography, clinical pathology, gross pathology, organ weights, and histopathology. Blood samples for determination of the plasma concentrations of CoQ10 IV Formulation were collected pre-dose and at 5, 15, 30 and 60 minutes and at 2, 4, 8 and 24 hours post-dose on Days 1 and 26.

TABLE 28

Repeat-Dose Toxicity
Report Title: A 4-Week Toxicity Study of 31510
Administered by Intravenous (Bolus) Injection to
Dogs with a 2-Week Recovery Period

| | | |
|---|---|---|
| Species/Strain: Beagle Dog | Duration of Dosing: 4 Weeks | Study No.: 20000334 |
| Initial Age: Approximately 6 to 7 Months | Duration Postdose: 2 Weeks | Location in CTD: m4-2-3-2 |
| Date of First Dose: 12 Apr. 2010 | Method of Administration: Intravenous (bolus) Injection Vehicle/Formulation: DMPC and Poloxamer 188 in PBS | GLP Compliance: Yes |

Special Features: Dosing occurred three times per week (Monday, Wednesday, Friday).
A single concentration of material was supplied (40 mg/mL): doses were achieved by varying the dose volume.
Highest Non-Severely Toxic Dose (HNSTD): 62.5 mg/kg/dose

| | Dose (mg/kg) | | | | | | | |
|---|---|---|---|---|---|---|---|---|
| | 0 | | 31.25 | | 62.5 | | 125 | |
| Number of Animals | M: 5 | F: 5 | M: 5 | F: 5 | M: 5 | F: 5 | M: 5 | F: 5 |
| Toxicokinetics: $AUC_{0-t}$ (µg · hr/mL) | | | | | | | | |
| Day 1 | NA | NA | 1129 | 1216 | 3354 | 2922 | 12790 | 12522 |
| Day 26 | NA | NA | 1038 | 1207 | 2719 | 2735 | 7151 | 7370 |
| Noteworthy Findings | | | | | | | | |
| Died or Sacrificed Moribund | 0 | 0 | 0 | 0 | 0 | 0 | 0 | 1[c] |
| Body Weight (%[a]) (kg) Food Consumption (%[a]) | 7.700 | 6.633 | +3.3 | +4.7 | 0.0 | +4.2 | +1.2 | −1.0 |

TABLE 28-continued

Repeat-Dose Toxicity
Report Title: A 4-Week Toxicity Study of 31510
Administered by Intravenous (Bolus) Injection to
Dogs with a 2-Week Recovery Period

| | | | | | | | | |
|---|---|---|---|---|---|---|---|---|
| Clinical Observations | — | — | — | — | — | — | — | — |
| Ophthalmoscopy | — | — | — | — | — | — | — | — |
| Electrocardiography | — | — | — | — | — | — | — | — |
| Hematology | | | | | | | | |
| Reticulocytes (109/L) | 185.8 | 201.2 | 48.7* | 36.7* | 68.0* | 52.0* | 190.6 | 160.69 |
| Clinical Chemistry | — | — | — | — | — | — | — | — |
| Urinalysis | — | — | — | — | — | — | — | — |
| Number Examined | M: 3 | F: 3 | M: 3 | F: 3 | M: 3 | F: 3 | M: 3 | F: 3 |
| Gross Pathology | — | — | — | — | — | — | — | — |
| Pale Liver | 0 | 0 | 0 | 0 | 3 | 3 | 3 | 3 |
| Organ Weights | — | — | — | — | — | — | — | — |
| Histopathology | | | | | | | | |
| Liver | | | | | | | | |
| Glycogen Accum. | 3 | 3 | 3 | 2 | 3 | 3 | 3 | 3 |
| Minimal | 2 | 1 | 2 | 2 | 0 | 2 | 0 | 2 |
| Mild | 1 | 2 | 1 | 0 | 3 | 1 | 3 | 1 |
| Post-Dose Evaluations | | | | | | | | |
| Number of Animals | M:2 | F:2 | +4.7 | +10.9 | −1.4 | +5.1 | +7.9 | −1.0 |
| Body Weight (%$^a$) (kg) | 8.521 | 7.636 | +4.7 | +10.9 | −1.4 | +5.1 | +7.9 | −1.0 |
| Hematology | | | | | | | | |
| Reticulocytes (109/L) | 149.3 | 86.0 | 71.6 | 63.4 | 85.4 | 50.8 | 131.1 | 53.6 |
| Gross Pathology | | | | | | | | |
| Pale Liver | 0 | 0 | 0 | 0 | 1 | 1 | 2 | 2 |
| Histopathology | | | | | | | | |
| Liver | | | | | | | | |
| Glycogen Accum. | 0 | 0 | 0 | 0 | 1 | 1 | 2 | 2 |
| Mild | 0 | 0 | 0 | 0 | 1 | 0 | 1 | 1 |
| Moderate | 0 | 0 | 0 | 0 | 0 | 1 | 1 | 1 |

— No noteworthy findings. NA = Not applicable.
*$p < 0.05$ (Anova/Dunnett or Kruskal-Wallis/Dunn's Test). Accum. = Accumulation.
$^a$At end of dosing or recovery period. For controls, group means are shown. For the treated groups, group mean percent differences from controls are shown.
$^b$Both absolute and relative weights differed from controls in the direction indicated. Number indicates percent difference for the absolute organ weights.
$^c$Female moribund sacrificed on Day 36 (during Week 2 of recovery).

All animals survived to the end of the treatment phase. One high dose female dog (125 mg/kg/day) was sacrificed in a moribumd condition during the second week of the recovery phase. Premortem signs included decreased food consumption, body weight loss, elevations in liver enzymes, and a pale appearing liver at necropsy, but a definitive cause of death was not determined following histopathological evaluation of tissues in this animal.

Among all other animals, no adverse test article-related findings were observed in clinical observations, body weights, food consumption, ophthalmic and electrocardiographic evaluations, clinical pathology, macroscopic, and organ weight parameters. Increases in reticulocyte counts were noted for the vehicle and high dose treated animals at the end of the treatment period, which persisted only in the males at the end of the recovery period. An association with the formulation vehicle cannot be ruled out. At necropsy, macroscopic observations were limited to a pale appearance to the liver at the middle and high dose groups, which was also noted at the recovery necropsy. At histopathology, no morphological alterations were seen in any tissue except the liver. Hepatocellular glycogen deposition was identified in all groups, including the vehicle treated group. No adverse changes were noted in the liver of these animals. Following the recovery period, these microscopic changes were limited to the middle and high dose animals.

Toxicokinetic evaluations revealed that exposure increased with increasing dose, with increases in $C_{max}$ and AUC tending to be greater than dose proportional. There were no remarkable gender differences and, in most cases, exposure parameters were similar on Days 1 and 26 except for decreased values for the high dose animals at Day 26. A tabular summary of pertinent parameters is shown below (Table 29).

TABLE 29

| | Dose (mg/kg/dose) | | | | | |
|---|---|---|---|---|---|---|
| | 31.25 | | 62.5 | | 125 | |
| Parameter | M | F | M | F | M | F |
| Day 1 | | | | | | |
| $C_{max}$ (ug/mL) | 534 | 518 | 1,114 | 1,074 | 2,930 | 701 |
| $AUC_{0-24}$ (ug · hr/mL) | 1,129 | 1,216 | 3,354 | 2,922 | 12,760 | 2,796 |

TABLE 29-continued

|  | Dose (mg/kg/dose) | | | | | |
|---|---|---|---|---|---|---|
|  | 31.25 | | 62.5 | | 125 | |
| Parameter | M | F | M | F | M | F |
| $T_{max}$ (hr) | 0.15 | 0.083 | 0.116 | 0.116 | 0.150 | 1.3 |
| $T_{1/2}$ (hr) | 2.74 | 2.97 | 3.62 | 2.83 | 3.92 | 4.14 |
| Day 26 | | | | | | |
| $C_{max}$ (ug/mL) | 518 | 555 | 1,282 | 1,324 | 2,322 | 2,322 |
| $AUC_{0-24}$ (ug · hr/mL) | 1,038 | 1,207 | 2,719 | 2,735 | 7,151 | 7,320 |
| $T_{max}$ (hr) | 0.083 | 0.082 | 0.183 | 0.116 | 0.150 | 0.200 |
| $T_{1/2}$ (hr) | 2.42 | 2.59 | 3.38 | 1.91 | 2.61 | 2.54 |

Based on data from this 4-week repeat dose toxicity study, the HNSTD was determined to be 62.5 mg/kg/dose.

IX. RELATED REFERENCES

All publications and patent documents cited in this application are incorporated by reference in pertinent part for all purposes to the same extent as if each individual publication or patent document were so individually denoted. By their citation of various references in this document, Applicants do not admit any particular reference is "prior art" to their disclosure. It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims and their equivalents.

All figures are offered by way of illustration, not by way of limitation. While specific examples have been provided, the descriptions are illustrative and not restrictive. Any one or more of the features of the previously described embodiments can be combined in any manner with one or more features of any other embodiments in the present disclosure. Furthermore, many variations of the present disclosure will become apparent to those skilled in the art upon review of this disclosure.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A therapeutic formulation suitable for intravenous administration to a subject comprising:
   an aqueous solution;
   coenzyme Q10;
   dimyristoylphosphatidyl choline; and
   poloxamer 188;
   wherein the coenzyme Q10 is dispersed into a colloidal nano-dispersion of particles having a mean size of less than 50 nm; wherein the coenzyme Q10 is present in said formulation in an amount of 4 wt %; wherein the dimyristoylphosphatidyl choline is present in said formulation in an amount of 3 wt %; and wherein the poloxamer 188 is present in said formulation in an amount selected from the group consisting of: 0.5 wt %, 1.0 wt % and 1.5 wt %.

2. The formulation of claim 1, wherein the colloidal nano-dispersion is a suspension or an emulsion.

3. The formulation of claim 1, wherein the coenzyme Q10 of the colloidal nano-dispersion is in a crystalline form.

4. The formulation of claim 1, wherein the coenzyme Q10 of the colloidal nano-dispersion is in a super-cooled melt form.

5. The formulation of claim 1, wherein the formulation has a wt % of the coenzyme Q10, dimyristoylphosphatidyl choline and poloxamer 188 of 4%, 3% and 1.5%, respectively.

6. The formulation of claim 1, wherein the mean size of the nano-dispersion particles is between 35-nm and 40-nm.

7. The formulation of claim 1, wherein the mean size of the nano-dispersion particles is less than 45-nm.

8. A therapeutic formulation suitable for intravenous administration to a subject comprising:
   an aqueous solution;
   coenzyme Q10 dispersed to form a colloidal nano-dispersion of particles;
   dimyristoylphosphatidyl choline; and
   poloxamer 188;
   wherein the coenzyme Q10 is dispersed into liposomes having a mean size of less than 50 nm; wherein the coenzyme Q10 is present in said formulation in an amount of 4 wt %; wherein the dimyristoylphosphatidyl choline is present in said formulation in an amount of 3 wt %, and wherein the poloxamer 188 is present in said formulation in an amount selected from the group consisting of: 0.5 wt %, 1.0 wt % and 1.5 wt %.

9. The formulation of claim 8, wherein the liposomes are bi-layered multilamellar liposomes having an aqueous space between the bi-layers and a lipophilic space within the bi-layers.

10. The formulation of claim 9, wherein the coenzyme Q10 is entrapped within the lipophilic space of the bi-layers.

11. The formulation of claim 9, wherein the multilamellar liposome further includes a hydrophilic agent entrapped in the aqueous space between the bi-layers.

12. The formulation of claim 8, wherein the colloidal nano-dispersion is a suspension or an emulsion.

13. The formulation of claim 8, wherein the coenzyme Q10 of the colloidal nano-dispersion is in a crystalline form.

14. The formulation of claim 8, wherein the coenzyme Q10 of the colloidal nano-dispersion is in a super-cooled melt form.

15. A therapeutic formulation suitable for intravenous administration to a subject comprising:
   an aqueous solution;
   coenzyme Q10;
   dimyristoylphosphatidyl choline; and
   poloxamer 188;

wherein the coenzyme Q10 is dispersed into a colloidal nano-dispersion of particles having a mean size of less than 50 nm, wherein the coenzyme Q10 is present in said formulation in an amount of 4 wt %; wherein the dimyristoylphosphatidyl choline is present in said formulation in an amount of 3 wt %; and wherein the ratio of the coenzyme Q10, the dimyristoylphosphatidyl choline and the poloxamer 188 is 4:3:0.5-1.5, respectively.

16. A method of preparing the therapeutic formulation of claim 1, wherein the method comprises dispersing the coenzyme Q10 by high pressure homogenization by:
adding the coenzyme Q10 to a 65° C. bath of water and mixing to form a hydrophobic active agent/water mixture;
adding dimyristoylphosphatidyl choline to the coenzyme Q10/water mixture and mixing at 65° C. to form a coenzyme Q10/water/dimyristoylphosphatidyl choline mixture;
adding poloxamer 188 to form a coenzyme Q10/water/dimyristoylphosphatidyl choline reducer mixture;
pre-heating a homogenizer to 65° C.; and
processing by mixing the coenzyme Q10/water/dimyristoylphosphatidyl choline/reducer mixture in the homogenizer at 65° C. such that a coenzyme Q10 colloidal nano-dispersion having a mean particle size of less than 50 nm is formed, and wherein the dimyristoylphosphatidyl choline is present in said formulation in an amount of 3 wt %.

17. A therapeutic formulation of claim 1, prepared by the method of claim 16.

18. The method of claim 16, wherein the coenzyme Q10 of the colloidal nano-dispersion is in the form of a super-cooled melt.

19. The method of claim 16, wherein the formulation has a wt % of the coenzyme Q10, DMPC and poloxamer 188 of 4%, 3% and 1.5%, respectively.

20. The method of claim 16, wherein a coenzyme Q10 colloidal nano-dispersion having a mean particle size of between 35-nm and 40-nm is formed.

21. The method of claim 16, wherein a coenzyme Q10 colloidal nano-dispersion having a mean particle size of less than 45-nm is formed.

22. The method of claim 16, further comprising the step of lyophilizing the colloidal nano-dispersion to crystallize the coenzyme Q10 colloidal nano-dispersion particles.

23. The method of claim 22, further comprising the step of adding a lyoprotectant.

24. The method of claim 23, wherein the lyoprotectant is a nutritive sugar selected from the group consisting of lactose, mannose, maltose, galactose, fructose, sorbose, raffinose, neuraminic acid, glucosamine, galactosamine, N-methylglucosamine, mannitol, sorbitol, arginine, glycine and sucrose.

25. The formulation of claim 15, wherein the colloidal nano-dispersion is a suspension or an emulsion.

26. The formulation of claim 15, wherein the coenzyme Q10 of the colloidal nano-dispersion is in a crystalline form.

27. The formulation of claim 15, wherein the coenzyme Q10 of the colloidal nano-dispersion is in a super-cooled melt form.

28. The formulation of claim 15, wherein the formulation has a wt % of the coenzyme Q10, dimyristoylphosphatidyl choline and poloxamer 188 of 4%, 3% and 1.5%, respectively.

29. The formulation of claim 15, wherein the mean size of the nano-dispersion particles is between 35-nm and 40-nm.

30. The formulation of claim 15, wherein the mean size of the nano-dispersion particles is less than 45-nm.

* * * * *